United States Patent
Hoang

(10) Patent No.: US 9,649,366 B2
(45) Date of Patent: *May 16, 2017

(54) MANUFACTURING AND PURIFICATION PROCESSES OF COMPLEX PROTEIN FOUND IN FRACTION IV TO MAKE A SEPARATED APO, TRANSFERRIN, AND ALPHA 1 ANTITRYPSIN (A1AT) OR A COMBINED TRANSFERRIN/APO/HUMAN ALBUMIN/A1AT AND ALL NEW FOUND PROTEINS

(71) Applicant: Kieu Hoang, Agoura Hills, CA (US)

(72) Inventor: Kieu Hoang, Agoura Hills, CA (US)

( * ) Notice: Subject to any disclaimer, the term of this patent is extended or adjusted under 35 U.S.C. 154(b) by 116 days.

This patent is subject to a terminal disclaimer.

(21) Appl. No.: 14/056,363

(22) Filed: Oct. 17, 2013

(65) Prior Publication Data

US 2014/0142284 A1 May 22, 2014

Related U.S. Application Data

(60) Division of application No. 13/114,951, filed on May 24, 2011, now abandoned, which is a continuation-in-part of application No. 13/108,970, filed on May 16, 2011, now abandoned, which is a continuation-in-part of application No. 13/064,070, filed on Mar. 4, 2011, now abandoned, which is a continuation-in-part of application No. 11/990,203, filed on Jul. 15, 2008, now abandoned, said application No. 13/114,951 is a continuation-in-part of application No. 12/457,796, filed on Jun. 22, 2009, now Pat. No. 8,013,122, which is a continuation-in-part of application No. PCT/US2007/020258, filed on Sep. 19, 2007.

(60) Provisional application No. 61/457,380, filed on Mar. 14, 2011, provisional application No. 61/452,860, filed on Mar. 15, 2011, provisional application No. 61/472,930, filed on Apr. 7, 2011.

(51) Int. Cl.

| A61K 38/00 | (2006.01) |
|---|---|
| A61K 38/57 | (2006.01) |
| A61K 38/17 | (2006.01) |
| A61K 38/38 | (2006.01) |
| A61K 38/40 | (2006.01) |
| A61K 38/36 | (2006.01) |
| A61K 38/37 | (2006.01) |
| A61K 38/39 | (2006.01) |
| A61K 38/48 | (2006.01) |
| C07K 14/775 | (2006.01) |

(52) U.S. Cl.
CPC .......... *A61K 38/57* (2013.01); *A61K 38/1709* (2013.01); *A61K 38/363* (2013.01); *A61K 38/37* (2013.01); *A61K 38/38* (2013.01); *A61K 38/39* (2013.01); *A61K 38/40* (2013.01); *A61K 38/4833* (2013.01); *A61K 38/4866* (2013.01); *C07K 14/775* (2013.01)

(58) Field of Classification Search
None
See application file for complete search history.

(56) References Cited

U.S. PATENT DOCUMENTS

| 4,533,496 A | 8/1985 | Lewis, Jr. et al. |
|---|---|---|
| 5,290,684 A | 3/1994 | Kelly |
| 2006/0134783 A1 | 6/2006 | Fong et al. |
| 2006/0247195 A1 | 11/2006 | Ray |
| 2007/0299251 A1 | 12/2007 | Lihme |
| 2010/0178272 A1 | 7/2010 | Hartmann et al. |
| 2011/0020308 A1 | 1/2011 | Schendel |
| 2012/0022239 A1 | 1/2012 | Van Alstine et al. |

OTHER PUBLICATIONS

Tu et al. (JBC, vol. 268, No. 31, p. 23098-23105, 1993).*
Green et al. (J. Clin. Invest., vol. 65, Apr. 1980, pp. 911-919).*
Lundquist et al. (J. of Biomaterials & Nanobiotech., 2011, vol. 2, pp. 258-266).*
Brace et al. (J. of Lipid Research, vol. 51, 2010, pp. 3770-3376).*
Baldini et al, "Correspondence between salivary proteomic pattern and clinical course in primary Sjogren syndrome and non-Hodgkin's lymphoma: a case report," Journal of Translational Medicine, vol. 9, No. 188, Nov. 2, 2011.
International Search Report in application No. PCT/US2013/024087, completed by officer Blaine R. Copenheaver Jun. 28, 2013.

* cited by examiner

*Primary Examiner* — Hope Robinson
(74) *Attorney, Agent, or Firm* — Merek, Blackmon & Voorhees, LLC

(57) ABSTRACT

Manufacturing and purification processes of complex protein found in Fraction IV to make a separated Apo, Transferrin, and Alpha-1 Antitrypsin (A1AT) or a combined Transferrin/Apo/Human Albumin/A1AT and all new found proteins. A complex of all proteins found currently in plasma, cryoprecipitate, Fraction III and many newly found proteins now being identified or any substances which are known proteins or unknown proteins which contain healthy cells and the combination of any of these known or unknown proteins which contain any one of these healthy cells: neutrophil, lymphocyte, eosinophil, basophil, and macrophage, and their potential applications for treating a wide variety of diseases and other physical conditions and disorders, and for maintaining health.

20 Claims, 55 Drawing Sheets

Colon cancer cell HCT 116 AFOD 2%

20110221

Colon cancer cell HCT 116 AFOD 10%

20110221

Breast cancer cell MCF AFOD 0%

Breast cancer cell MCF AFOD 2%

Breast cancer cell MCF AFOD 10%

Liver cancer cell HepG2 AFOD 0%

Liver cancer cell HepG2 AFOD 2%

Liver cancer cell HepG2 AFOD 10%

Pancreas cancer cell PAC-1 AFOD 0%

Pancreas cancer cell PAC-1 AFOD 2%

Pancreas cancer cell PAC-1 AFOD 10%

12

19

MANUFACTURING AND PURIFICATION PROCESSES OF COMPLEX PROTEIN FOUND IN FRACTION IV TO MAKE A SEPARATED APO, TRANSFERRIN, AND ALPHA 1 ANTITRYPSIN (A1AT) OR A COMBINED TRANSFERRIN/APO/HUMAN ALBUMIN/A1AT AND ALL NEW FOUND PROTEINS

CROSS REFERENCE TO RELATED APPLICATIONS

The present application is a division of prior application Ser. No. 13/114,951, filed on May 24, 2011, which is hereby incorporated herein by reference in its entirety and which is a continuation-in-part of prior application Ser. No. 13/108,970, filed May 16, 2011, which is hereby incorporated herein by reference in its entirety and which is a continuation-in-part of prior abandoned application Ser. No. 13/064,070, filed Mar. 4, 2011, which is hereby incorporated herein by reference in its entirety and which is a continuation-in-part of prior abandoned application Ser. No. 11/990,203, filed Jul. 15, 2008, which is hereby incorporated herein by reference in its entirety. Abandoned application Ser. No. 13/114,951 is a continuation-in-part of prior application Ser. No. 12/457,796, filed Jun. 22, 2009, and resulting in U.S. Pat. No. 8,013,122, which is hereby incorporated herein by reference in its entirety and which is a continuation-in-part of prior application No. PCT/US 2007/020258, filed Sep. 19, 2007. The benefit under 35 USC 120 is hereby claimed of the filing dates of provisional application No. 61/457,380, filed on Mar. 14, 2011 and provisional application No. 61/457,380, filed on Mar. 14, 2011 and provisional application No. 61/452,860, filed on Mar. 15, 2011 and provisional application No. 61/472,930, filed on Apr. 7, 2011, all of which are hereby incorporated herein by reference in their entireties.

A Complex of all proteins found currently in Plasma, Cryoprecipitate, Fraction III and newly found many proteins being identified, Prothrombin Complex Concentrate (ProthoRAAS®), Albumin (AlbuRAAS®), Factor VIII (HemoRAAS®), Fibrinogen (FibroRAAS®), High concentrate Fibrinogen (FibrinGluRAAS®), Thrombin (ThrombiRAAS®), Thrombin for Fibrin sealant (FibrinGluRAAS), AT-III Protein, Protein C, Protein S, Protein M, Protein G, Alpha 1 Antitrypsin (A1AT), HDL ApoA1, ApoA2, ApoA4, Semenogelin-1, Haptoglobin, Vimentin, Nesprin-2 Interferon Alpha1/13, HP Protein, Vitamin B Binding, Alpha-Fetoprotein, Cask Protein, Amyloid precursor, Neurexins, Syndecans, Protein rankl, and from other antibodies, Immuno globulins (GammaRAAS®), Hepatitis B Immune Globulin (Hepa RAAS®) Hepatitis A Antibodies, Cytomegalovirus Antibody, Anti-D Antibody, Zarizella Zoster Antibody, RSV Antibodies, SARS Antibody, H1N1 Antibodies, H1N5 Antibodies, West Nile Virus Antibody, or all antibodies in human or monoclonals, white blood cells, red blood cells, platelets, chylomicron, electrolyses, albumin, globulins, peptides, tissues, placenta, catalase, All Factors, Cryoprecipitate, 5 Fractions I, II, III, IV, V of Human Blood and Plasma, Monoclonal antibodies, Recombinant DNA proteins, Transgenic proteins, particles, or any substances which are known proteins or unknown proteins which contain GOOD HEALTHY CELLS and the combination of any of these Known or unknown proteins which contain any one of these GOOD HEALTHY cells Neutrophil, Lymphocyte, Eosinophil, Basophil, and MACROPHAGE and Their potential applications for:

Schizophrenia, cholesterol, depression, AIDS, all enveloped viruses (Hepatitis A, B, C, D, E, G, SARS, H1N5, H1N1 non enveloped viruses), clean plaque, fat on liver, heart attack, stroke, life span, control of obesity, control of blood pressure, hypertension, paralysis due to the stroke. All solid tumor cancers: AIDS related cancers, anal cancer, appendix cancer, bile duct, bladder, osteosarcoma, brain, breast, cervical, colon, esophagus, eye, gall bladder, gastric, other gastrointestinal, intestines, head neck, heart, liver, hypopharyngeal, kidney, laryngeal, lip oral cavity, lung, mouth, nasal, parasal, ovarian, pancreas, parathyroid, penile, prostate, rectal, renal cell carcinoma, salivary, skin, spleen, throat, testicular, urethral, vaginal. Leukemia, (Acute myeloid leukemia (M0-M7), lymphoma, marrow malignancy, acute lymphoid leukemia (small, middle, large) MDS, myeloid dysfunction syndrome and anemia.

Sepsis, hyper inflammatory diseases, acute pancreatitis, acute respiratory distress syndrome, ischemia reperfusion injury, hepatic cirrhosis, renal failure and anti-oxidant. Alzheimer disease, autism, Parkinsons, diabetes. Chemotherapy, radiotherapy and cytokine therapy toxicity, TNF and stop activation of histone and endotoxin. Autoimmune diseases. Rheumatoid arthritis, tuberculosis, malarias. Lupus sclerosis in brain, A1AT deficiency, emphysema, lung cancer, asthma, Prion (mad cow), anthrax and all bacteria, food poisoning, Factor VII deficiency and surgery. Hemophilia A, Hemophilia B, VWB eventually will increase coagulation, all other unknown viruses, bacteria infections, healthy cells replacement to maintain youthfulness. Alpha 1 Antitrypsin (A1AT), C1 esterase inhibitor and all inhibitors/deficiencies in human body.

DESCRIPTION OF INVENTION AND ITS PURPOSES

Mankind have been suffering for hundreds of years for all kind of diseases, cancers, Alzheimer, diabetic, Parkinson, Autism and specially the agonies that we have to go through with AIDS, Hepatitis B, and Hepatitis C and new kinds of Virus infections and epidemic Incidence which feared and affected the economy of the world like SARS in China, Taiwan, Hong Kong, Vietnam, Singapore, Canada in 2003, with outbreak of bird flu (H1N5) 2004 in Europe, Vietnam, Thailand and most recently in 2010 in Mexico with the outbreak of (H1N1) which caused the country to shut down for weeks and badly affected its economy.

On the other hand, Most of countries in the World not only face with problematic economies but also with The increased Healthcare cost for each country. Such a health care system spends a lot of money for Healthcare which drags down economy.

Such an invention of these products will help save a lot of money for any country in Healthcare.

However the patients that benefit from these discoveries must understand their social responsibilities as they will live longer with very healthy conditions without Alzheimer, any kind of diseases, cancers, heart attack, stroke, and their prevention.

The definition of death is when the heart stops beating. AFODRAAS 1-85, AFCC 1-85 and ProthoRAAS® will clean up all plaque in our bodies to help the blood flow through all part of our bodies including the heart. AFODRAAS 1-85 (also referred to herein as "AFODRAAS 1", "AFODRAAS" and "AFOD") contains various combinations of apolipoproteins ApoA1, ApoA2, ApoA4, Apo-B48, ApoB100, ApoCI, ApoCII, ApoCIII, Apo-D, Apo-E, Apo-H, and Apo(a), all of which contain Good Healthy cells, as well as Alpha 1 Antitrypsin (A1AT), which is known also to contain Good Healthy Cells, Transferrin, which contains Good Healthy Cells, and Human Albumin, another Good Healthy cell Protein, together with a group of at least 20 unidentified discovered proteins which are being identified and characterized with the assistance of Academy of Science of China, the group containing Good Healthy cells. Each combination will be applied to a certain number of diseases, including solid and Blood cancers.

AFCC 1-85 (also referred to herein as "AFCCRAAS 1-85", "AFCCRAAS 1", "AFCCRAAS" and "AFCC") contains various combinations of Prothrombin Complex Concentrate including all 13 Factors found in Fraction III, Alpha 1 Antitrypsin (A1AT), Transferrin, Human Albumin, and Anti thrombin III, all of which contain Good healthy cell proteins. The combinations of AFCC 1-85 can also contain Transferrin, which contains Good Healthy Cells, and Human Albumin, another Good Healthy cell Protein, together with a group of at least 20 unidentified discovered proteins which are being identified and characterized with the assistance of Academy of Science of China, the group containing Good Healthy cells. Each combination will be applied to a certain number of diseases, including solid and Blood cancers.

The definition of death belongs to the beating of the heart, but if the LIVER will not manufacture, moderate, regulate and distribute Good Blood cells to the heart, the heart will not function.

So in this discovery of invention: The liver has become the most important organ of the body as the liver produces antibodies and proteins which are used to cure diseases and viruses as well as bacterial infection. The liver is the largest organ in the body weighting approximately 1.4 kg. It is located on the right side of belly. Right under the chest bone. It has two pieces. The right piece is larger and consists of 3 smaller pieces together. The left piece is smaller, right on top of stomach adjacent to the throat. The structure of the liver consists of from 50,000 to 100,000 small pieces with portal Vein in the middle. From the portal vein, hundreds of liver cells mix with pile system and very tiny blood vessels. With approximately 300 billion of cells (Approximately 30% of a trillion of cells in our body). It has the ability to restore and maintain its function in case for any reason it has lost 90% of the liver. None of other organ which has only 10% can function in our body. If 100% of the liver has been damaged due to the diseases a person can only live with a piece of liver transplant. The liver receives blood through portal vein and arterial vein. Every minute all these blood vessel has transferred to liver approximately 1.5 liter of blood. Blood in arterial vein contain plenty of oxygen as for blood in portal vein transport all waste from digestion. Liver is considered as a sophisticated chemical manufacturer/moderator/regulator/distributor with hundreds of Different important tasks:

1. Liver is the warehouse to receive glucose from small intestine store as glycogen. After each meal, when the blood pressure increases, insulin from pancreas will help the liver to transform glucose into glycogen. In a few hours later when the blood pressure decreases, the liver again to transform glycogen into glucose then send glucose to the blood then distribute to other organs or components which need glucose. Diabetic people cannot receive insulin produced by pancreas due to the accumulation of glucose from foods in the liver.

2. Beside the above task, liver also transform glucose and fat into protein and it also transform protein and fat into glucose.

3. The liver produces approximately 0.5-0.9 liter of pile every day. Pile is a liquid with the yellow-blue color, It is bitter with its most important structure is pile salt which is necessary for the digestion of Fat in the foods.

4. Liver can eliminate some toxicity like alcohol and a few drugs like acetaminophen.

5. The liver produces urea, a waste from the protein and eliminate through kidney.

6. The liver destroys all damaged or old red cells as well as destroys all bacteria in the foods in the intestine.

7. The liver contains vitamins, A, B, D, E and K

8. Liver creates the protein in the blood like albumin, globulin and coagulation.

Fat on the Liver:

When learning about the fat on the liver, people usually feel surprised and scared and question how could one survives with fAT on the liver. In reality, liver like other organs of our body, everywhere we have fat.

Fat is a creative element of cells. Whenever fat in the liver exceeds around 5% of the liver, attack and occupy all healthy cells then there will be a problem. At this time, liver will have a fatty yellow color, the liver becomes bigger and heavier than normal.

Cut a piece of the liver without disease, through microscope, we see the blood full of in space between the liver cells.

Tissue factor cells surrounding blood vessels will take away toxicity, bacteria, fat to transform blood cleaner. Liver is like a filter. If now in liver cells and the space between the liver cells, are full of fat, then the filtration and other functions of the liver will decrease and lead one to bad consequence.

All fat majorities of them belong to triglycerides.

In our pre animal clinical study using lab scale product of AFODRAAS (1-85) A total of 14 rabbits out of 60 died during the 10 weeks of High Fat Diet Feed due to stomach and fat accumulation on the liver.

Macrophage (in Greek language BIG EATERS from makros "Large"+phagein "eat") are white blood cells produced by the differentiation of monocytes in tissues. Human macrophages are about 21 micrometers in diameter. Monocytes and macrophages are phagocytes. Macrophages function in both non specific defense (innate immunity) as well as initiate defense mechanisms (adaptive immunity). Their role is to phagocytose (engulf and then digest) cellular debris and pathogens. MACROPHAGE are important and good healthy cells play a very important role in the body's defense system such as liver by engulfing and then digesting bacteria and other foreign particles.

Complement in the liver is a group of protein that play a part in the immune system's defenses against infection.

Due to their role in phagocytosis, macrophages are involved in many diseases of the immune system. Like HIV infection, macrophages play a role in Human Immunodeficiency Virus (HIV) infection. Like T cells, macrophages can be infected with HIV, and even become a reservoir of ongoing virus replication throughout the body. Due to the lack of healthy cells in the body; the infected cells have gone through the system in the liver and the bad cells eat the bad cells again. That is why viruses replicate. Our study NAT testing of a positive by NAT of HIV 1,2 has shown the reduction of IU/ML after three days of introducing our AFODRAAS 1 and AFCCRAAS 1 into the HIV 1,2 positive plasma.

HEART DISEASE: Macrophages are the predominant cells involved in creating the progressive plaque lesions of atherosclerosis. That is why lowering Triglycerides, VLDL, LDL, and increasing HDL will not remove the plaque lesions by foreign substances like chemicals that do not contain a healthy macrophage cell or some other healthy cells which have not been discovered as we have seen a lot more of proteins found in Fraction III of plasma under investigation. In our study of 52 rabbits has proven this.

TUBERCULOSIS: Once engulfed by a macrophage the causative agent of tuberculosis, *Mycobacterium tuberculosis* avoids cellular defenses and uses the cell to replicate.

CANCERS: Macrophages are believed to help cancer cells proliferate as well. They are attracted to oxygen-starved (hypoxic) tumor cells and promote chronic inflammation. Inflammatory compounds such Tumor necrosis factor (TNF) released by the macrophage activates the gene switch nuclear factor -kappa B.NF-kB then enters the nucleus of a tumor cell and turns on production of proteins that stop apoptosis and promote cell proliferation and inflammation.

For all 8 Different cancer cells line, we have tested; all cancer cells have been eaten up to some degree at 2% protein and completely at 10% protein.

INVENTION

All of the following invented method of manufacturing and purification, the final product of which should contain one of the following good cells: neutrophil, lymphocyte, eosinophil, basophil and macrophage
1. Manufacturing and purification of complex of protein found in Fraction IV to make
   A separated (HDL) ApoA1'
   Transferrin,
   Alpha 1 Antitrypsin (A1AT).
2. A combined Apo/Transferrin/Human Albumin/A1AT,
3. A combined Apo Transferrin/Human Albumin, Immunoglobulin
4. A combined Apo/AT1A/Human Albumin/Immunoglobulin
5. A manufacturing and purification of Prothrombin complex concentrated from Fibrinogen
   That contains A1AT, Apo, Fibrinogen, Human Albumin, and Immunoglobulin.
6. Manufacturing and purification of Thrombin complex concentrated from Fraction III (ProthoRAAS®)
   Containing Factor II, VII, IX, X, Transferrin, Human Albumin, ATA1 and Apo.
7. Manufacturing and purification of complex of protein found in Fraction III (Combined) consisting all 13 factors, PCC, Thrombin, AT-III, A1AT, HDL, and other NEW proteins (under study) found in this Fraction III.
8. Combination of one of the above method of manufacturing and purification of the existing line of products 1. Human Albumin (AlbuRAAS®) Intravenous Immunoglobulin. 2.GammaRAAS®. Factor VIII (3 HemoRAAS®) 4. Prothrombin Complex Concentrate (ProthoRAAS®) 5. Fibrinogen (FibroRAAS®) 6. High Concentrate Fibrinogen (FibrinGluRAAS®) 7. Thrombin (ThrombiRAAS). 8. Thrombin for Fibrin Sealant (FibrinGluRAAS®), Hepatitis B Immunoglobulin (Hepa B RAAS).

Any of the single protein or combined protein of the above that contains any of one of good cells namely neutrophil, lymphocyte, eosinophil, basophil and macrophage and it is possible That new cells may be found as we have found a lot more of Protein in the Fraction III of plasma under investigation.

Through in vitro and in vivo studies have proven their potential abilities to kill (or eat up) all cancer cells, bacteria, enveloped viruses eat up all High fat (Triglyceride) build up in plaque. The above healthy tissue factor cells surrounding the blood vessels in the protein will take away, toxicity bacteria, fat to transform blood cleaner then go through the filtration of the liver from where The bad fat will go through kidney to eliminate liquid waste as urea which comes out of our body as urine.

Urine has been used to make urokinase for the treatment of stroke.

In addition, urea fertilizer has been used for years in order to kill all worms, insecticides, buds in the soil to fertilize the soil for growing rice, vegetables, and fruits. When I was 5 years old in a poor country side village in Vietnam I wondered why my grandmother asked me to urinate in a jar then later my grandmother used my urine and others as well to mix with water and fertilized the soil to grow vegetables and fruits.

In the study of 52 Rabbits, we have seen Weight losses of studied rabbits with the control group with 10.00% weight reduction for treated group 1 and 14.52% for treated group 2. Both groups were fed with High fat Diet. So the control of obesity is possible. Total Triglyceride is −3.07%, Total Cholesterol −30.07% and −37.05% VLDL-C −44.42% and −41.87% LDL-C −21.59% and −33.96% HDL 92.36% and 54.15% TC/HDL-C −55.55% and −40.48%. Potential applications for all cardiovascular diseases.

Fat build up in plaque area have been decreased 38.43% and 29.05% to compare with control group, −27.36-20.69 potential applications for stroke, heart attack, paralysis due to stroke, blood pressure, hypertension.

Liver index of the study did not show any changes after AFODRAAS 1 treatment proves that the potential protein will not cause any damage to the liver it is easy to understand that as this protein is from Mother Nature, human plasma, not from a foreign substance, chemicals that usually react and damage the liver.

As any one guess there are 10 billion antibodies and at least 1 trillion cells in a human body, so far circa three hundred antibodies have been discovered and how many proteins have been discovered from human plasma?

Back to 1975 until now, we have discovered Hepatitis B Virus (HBV) in 1975, HIV (Human Immunodeficiency virus in 1983, Hepatitis C Antibody virus (HCV) in 1990, Creutzfeldt-Jakob Disease prion (CJD), Variant Creutzfeldt-Jakob disease prion (v-CJD) in 2000. Severe Acute Respiratory Syndrome corona virus (SARS-CoV) in 2004, West Nile Virus (WNV) in 2005, Bird Flu virus (H1N5) in 2005, Influenza A virus subtype H1N1 in 2010

Since 1975 when Hepatitis B Surface Antigen by RIA was introduced by Abbott Laboratories even utilizing test kit to test for the unit of plasma for the presence of Hepatitis B surface antigen, blood products were still contaminated with Hepatitis B virus in the products of Fibrinogen, Factor VIII, and Factor IX as the Test method is not sensitive enough. It is proven in our table for the number of Units of plasma have been tested by ELISA false positive, but we have to use as it a quick testing method to eliminate the potential donors.

For HIV virus, It was not discovered until 1984 and the method of effective virus inactivation by S/D discovered by New York Blood center in mid-1985, Almost all hemophiliacs have been contaminated with HIV 1 virus.

With regard to Hepatitis C Virus (HCV) was discovered in 1990 and the Enzyme linked Assay for the detection of Hepatitis C Antibody was introduced thereafter However, the contamination of Hepatitis C in immunoglobulin too place in Brazil.

With regard to Hepatitis A, a non enveloped virus which cannot be killed by Solvent Detergent method Contaminated in Factor VIII in many countries in Europe.

From 2000 on with more effective measures taken in the inactivation of non enveloped and enveloped virus including prion has improved significantly and with the assistance of NAT testing's of pool of plasma used for the production of plasma derived medicinal products.

However in 2010, immunoglobulin of one company in Europe has caused heart attack and stroke to the patients due to their processes to optimize yield which carries other fraction like Fraction III which contains Thrombin to cause Thrombosis in patients. Otherwise, today plasma derived medicinal products are much safer than before the year of 2000.

HBV (Hepatitis B virus) 1975
HIV (Human immunodeficiency virus (1983)
HCV (Hepatitis C virus) 1990
CJD (Creutzfeldt-Jakob Disease prion)
v-CJD (Variant Creutzfeldt-Jakob Disease prion) 2000
SARS-CoV (Severe Acute Respiratory Syndrome corona virus) 2004
WNV (West Nile virus) 2005
H1N5 (Bird Flu virus)
Influenza A virus subtype H1N1 2010

For Viruses: In NAT testing of samples of HIV Positive Plasma mixed with different dosages of AFODRAAS1 and AFCCRAAS 1 by NAT testing show a tremendously decrease in IU/ML. Potential killing HIV 1,2 virus and other enveloped and non enveloped viruses as well.

We have made improvement in preventing the contamination of viruses into plasma derived medicinal products, however the contamination of Human Albumin in 1996 in The United States with bacteria.

Bacteria contamination will not spare any products. We thought when we came up with rDNA Factor VIII, the contamination of viruses not possible, however in 2003, the contamination of RDNA Factor VIII by one company in the United States of America has caused a severe shortage of rDNA Factor VIII in the world in 2003 and 2004.
Bacteria Contamination in Flu Vaccine in England 2004
In 2010, bacteria contamination in drugs in the United States of America
In 2010, contamination of eggs (substrate for vaccine production) with *Salmonella enteritidis*.
Recombinant DNA products like rDNA Factor VIII in 2003
Vaccine in 2004 (England)
Contamination of eggs (substrate for vaccine production) with *Salmonella enteritidis* (2010)
For Bacteria:

For both AFODRAAS 1 and AFCC RAAS1 have killed some kind of lethal Bacteria like *Staphylococcus aureus* that are resistant to our current antibiotic arsenal MRSA (Methicillin-Resistant *Staphylococcus Aureus*) which currently kill approximately 20,000 people a year in the US according to Forbes Feb. 14, 2011. Potential indications for all bacteria and sepsis which kill about 200,000 people a year in US out of 700,000 people having sepsis with large dosages.

The contamination of bacteria should not happen in the first place; however any drugs combined with AFODRAAS1-85 and AFCCRAAS1-85 with large dosage will prevent bacterial contamination.

For solid tumor cancers and blood (liquid) Cancers: A total of 8 different cells for Colon cancer cell Hct-116, Colon cancer line LS174T, Breast Cancer cell MCF-7, Liver cancer cell HepG2, Pancreas Cancer cell PAC-1 Gastric Cancer cell 7901, Gastric Cancer cell AGS, and Gastric cancer line with 2000 cell each type were used to test with 2% of protein which killed certain number of cancers cells big number or smaller number depending type of cells but at 10% protein All above cancer cells are killed. Potential applications for all solid tumor cancers and blood (liquid) cancers.

All of diseases, cancers, inhibitors, immune deficiencies are caused by bad cells which turn into the bacteria, viruses, prions.

Now with this invention, we can conclude due to the lack of healthy cells which are in the blood going through liver for manufacturing, moderating, regulating, and distributing to the other organs and other parts of our body, such as brain (due to the lack of these healthy cells, people having Alzheimer/Autism/Parkinson)

For diabetic due to accumulation of glucose (which is also fat) with these healthy cells can eat up all fat and send good blood cells to kidney to help produce insulin.

For Hemophiliac A, B and VWD: one of the liver function is to produce coagulant, however these Hemophiliac lack healthy cells for the liver to produce coagulant.

All protein from good healthy cells which is also produced by liver can prevent the production of endotoxin (Transferrin), cytokine, toxicity, TNF and prevent the activation of histones.

All protein or antibodies from healthy cells which is also produced by the Liver can prevent all of deficiencies in our bodies.

All good health cells from protein or antibodies can be used with other drugs currently in the market or in the future to prevent side effects damaging the liver, kidney or any other organs of the body along with heart attack like in the case of Viagra, and work much better with drugs to lower triglycerides like Arvostatin and Lipitor for decreasing LDL. These are well known drugs not to mention, it will work well with other thousands of drugs available in the market today and any future developed drugs

BACKGROUND

The liver is the only organ which produces proteins and antibodies, both of which play a very important roles in the defense of people against diseases, viruses, bacteria infections. This discovery reveals any protein that contains a healthy cell will properly can be used against any diseases, viruses, bacteria, deficiencies, inhibitors, prion in our body and thus from now on mankind will be protected Against all kinds of diseases, cancers, epidemics, viruses, bacteria and possibly blind, deaf, mute people may benefit.

The cells of the blood can be divided into: white blood cells, red blood cells and platelets.

Red blood cells, or erythrocytes are the most common type of blood cell and our principal means of delivering oxygen to the body tissues through the circulatory system (arteries). Red blood cells take up oxygen in the lungs and release it while circulating through the body's capillary vessels (the smallest structures that conduct blood), where they take up carbon dioxide, which is a waste product of metabolism, and take it to the lungs, to be discarded through the respiration. These cells are rich in hemoglobin, which is a molecule that contains iron and that can bind oxygen (and is responsible for the blood's red color).

The red blood cells develop in the bone marrow and circulate for about 100-120 days in the body before their components are recycled by macrophages.

Red blood cells do not participate in the immune system.

Platelets are cell fragments (that is, cells that do not have a nucleus, 2-3 μm in diameter, which are derived from fragmentation of precursor cells known as "megakaryocytes". The average lifespan of a platelet is normally just 5 to 9 days. Platelets play a fundamental role in hemostasis with the formation of clots, but they do not participate in the immune system.

White blood cells, or leucocytes, are cells of the immune system involved in defending the body against both infectious disease and foreign materials. There are five different and diverse types of leukocytes exist, but they are all produced and derived from a multi potent cell in the bone marrow, known as a hematopoietic stem cell. Leukocytes are found throughout the body, not only in the blood and the lymphatic system.

The number of white blood cells in the blood is often an indicator of disease. There are normally between 5,000 to 10,000 white blood cells per mL. An increase in the number of leukocytes over the upper limits s called leukocytosis, and a decrease below the lower limit is called leukopenia.

Origin

Chylomicrons are a type of lipoprotein produced in absorptive cells of small intestines, specifically, the epithelial cells within the villi of the duodenum.

Stages

There are three stages in the chylomicron's "life cycle":
Nascent chylomicron
Mature chylomicron
Chylomicron remnant Nascent Chylomicrons Chylomicrons are created by the absorptive cells of the small intestine, known as enterocytes. They are relatively large, having a diameter of 75 to 1,200 nm. These nascent chylomicrons are released by exocytosis from enterocytes into lacteals, lymphatic vessels originating in the villi of the small intestine, and are then secreted into the bloodstream at the thoracic duct's connection with the left subclavian vein.

Nascent chylomicrons are primarily composed of triglycerides (85%) and contain some cholesterol and cholesteryl esters. The main apolipoprotein component is apolipoprotein B-48 (APOB48).

| Type of cell | % | Main targets | Lifetime |
|---|---|---|---|
| Neutrophil | 54-62 | Bacteria and fungi | 6 hs to a few days |
| Lymphocyte | 25-33 | B Lymphocytes (releases antibodies and assist "activation" of T lymphocytes) T Lymphocytes: Helper (activate and regulate T and B lymphocytes) Cytotoxic T lymphocytes CD8+ (virus-infected and tumor cells) Gamma-delta T lymphocytes (suppressor T lymphocytes) Returns the functioning of the immune system back to normal operation after infection and prevents autoimmunity Natural killer T lymphocytes (virus-infected and tumor cells) | Weeks to years |
| Eosinophil | 1-6 | Larger parasites Modulate allergic inflammatory responses | 8-12 days |
| Basophil | <1 | Release mediators (histamine) in inflammatory response | Hours to days |
| Monocyte | 2-10 | Monocytes migrate from the bloodstream to other tissues and differentiate into tissue resident macrophages or dendritic cells | Hours to days |
| Macrophage | No* | Phagocytosis (engulfment and digestion) of cellular debris and pathogens, and stimulation of lymphocytes and other immune cells that respond to the pathogen. | activated: days immature: months to years |

Another important support role in transporting protein is Chylomicrons (Mainly Triglycerides which is considered very BAD according to a lot of publications and it may lead to Heart attack and Stroke. However, without triglycerides FATS and cholesterol cannot Move within the water-based solution of the Blood stream.

Chylomicrons are large lipoprotein particles that consist of triglycerides (85-92%), phospholipids (6-12%), cholesterol (1-3%) and proteins (1-2%) [1]. They transport dietary lipids from the intestines to other locations in the body. Chylomicrons are one of the five major groups of lipoproteins (chylomicrons, VLDL, IDL, LDL, HDL) that enable fats and cholesterol to move within the water-based solution of the bloodstream.

Function: Chylomicrons transport exogenous lipids to liver, adipose, cardiac, and skeletal muscle tissue, where their triglyceride components are unloaded by the activity of lipoprotein lipase. As a consequence, chylomicron remnants are left over and are taken up by the liver.

Mature Chylomicron

While circulating in lymph and blood, chylomicrons exchange components with high-density lipoproteins (HDL). The HDL donates apolipoprotein C-II (APOC2) and lipoprotein E (APOE) to the nascent chylomicron and thus converts it to a mature chylomicron (often referred to simply as "chylomicron"). APOC2 is the cofactor for lipoprotein lipase (LPL) activity.

Chylomicron Remnant

Once triglyceride stores are distributed, the chylomicron returns APOC2 to the HDL (but keeps APOE), and, thus, becomes a chylomicron remnant, now only 30-50 nm. APOB48 and APOE are important to identify the chylomicron remnant in the liver for endocytosis and breakdown.

References 1.^ M Mahmood Hussain: "Review Article: A proposed model for the assembly of chylomicrons"; Arterosclerosis; Vol. 148; 2000; pages 1-15;

INVENTIONS: Several Manufacturing processes of a protein that contain one of the Healthy GOOD CELLS as described. Few of them are described here and the rest as we can separate Protein by Protein by different process, it can be combined from one protein with others to contain one of these Health Good Cells.

The present invention relates to a method of introduction of a healthy good human cells to eat up bad damaged or cells, comprising administering an effective amount of a healthy good protein containing transferin, alpha 1-antitrypsin, apolipoprotein A and human albumin.

By the present invention, damage to healthy human cells can be reduced by administering an effective amount of a healthy good protein containing ApoA1/2/4 and/or transferrin and/or alpha 1 antitrypsin and/or C1 esterase inhibitors and other inhibitors.

The present invention also involves a method of introduction of healthy goodies human cells to eat up bad damaged cells to reduce damage to healthy human cells, comprising administering an effective amount of a healthy good protein containing Factor II, Factor VII, Factor IX and Factor X in Prothrombin Complex Concentrate (ProthoRAAS®). The damage to healthy human cells can be reduced by administering an effective amount of a protein containing any one or more of: human albumin (AlbuRAAS®), immunoglobulin (GammaRAAS®), fibrinogen (FibroRAAS®), Factor VIII (HemoRAAS®), high concentrate fibrinogen (FibrinGluRAAS®), thrombin (ThrombiRAAS®), Hepatitis B and Immune Globulin (HBIG) (HepaRAAS®).

The present invention further involves a method of reducing damage to healthy human cells, comprising administering an effective amount of a healthy good protein containing one or more of: Anti thrombin III (AT-III), protein C, fibronectin, protein S, and protein M. An effective amount of two or more of the proteins described herein for use with the present invention can be used. The proteins include all currently known proteins and proteins yet to be discovered in Fraction III of plasma.

The method of the present invention further involves reducing damage to healthy human cells by administering an effective amount of any of: a macrophage, a neutrophil, a basophil, a lymphocyte and an eosinophil in white blood cells, red blood cells, platelets, chylomicrons, electrolyses, and peptides in humans or in animals or in chemicals or in substances from any source of materials obtaining by clone expressing to obtain the cells for further purification by rDNA, monoclonal, transgenic, or by any other methodology.

The more healthy good proteins that are used in effective amounts in a combination of proteins means that the combination will be more potent and effective than a single healthy good protein in the treatment of diseases and viruses or bacterial infections. The method of reducing damage to healthy human cells according to the present invention comprises any good healthy protein of, for example, AFOD RAAS 1-85 and AFCC RAAS 1-85 can be combined with any currently available and future developed drugs to enhance the efficacy, while reducing toxicity and the side effects caused by chemical drugs.

The method according to the present invention also involves introducing healthy goodies human cells to eat up bad damaged cells, the method comprising administering an effective amount of a protein containing at least one of the following apolipoproteins: ApoA1, ApoA2, ApoA4, Apo-B48, ApoB100, ApoCI, ApoCII, ApoCIII, Apo-D, Apo-E, Apo-H, and Apo(a), all of which contain good healthy cells. The protein further contains at least one of the following: alpha 1 antitrypsin (A1AT), transferrin, and human albumin, all of which contain good healthy cells.

BRIEF DESCRIPTIONS OF THE DRAWING FIGURES

Figure 33:
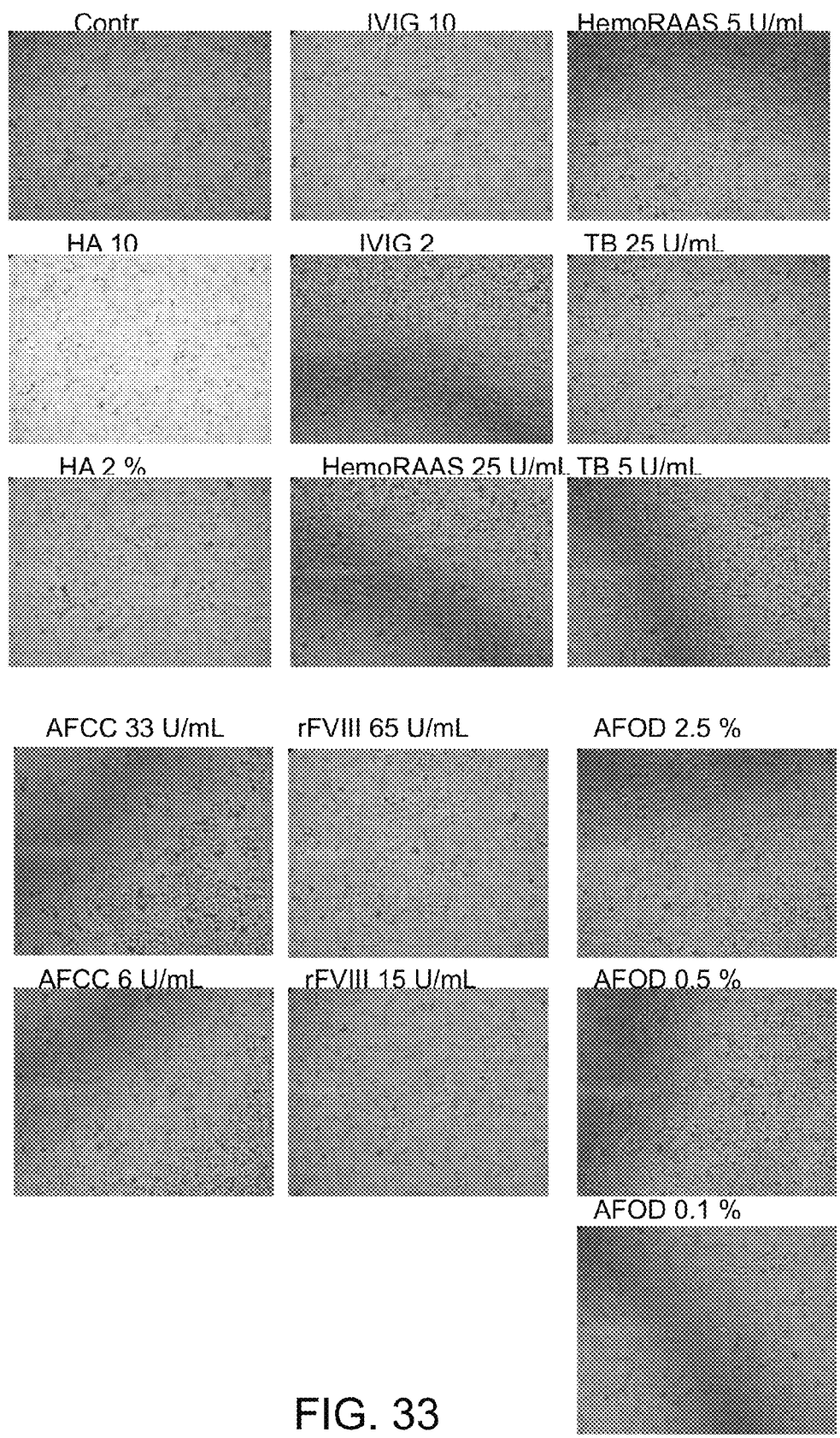
Figure 34:
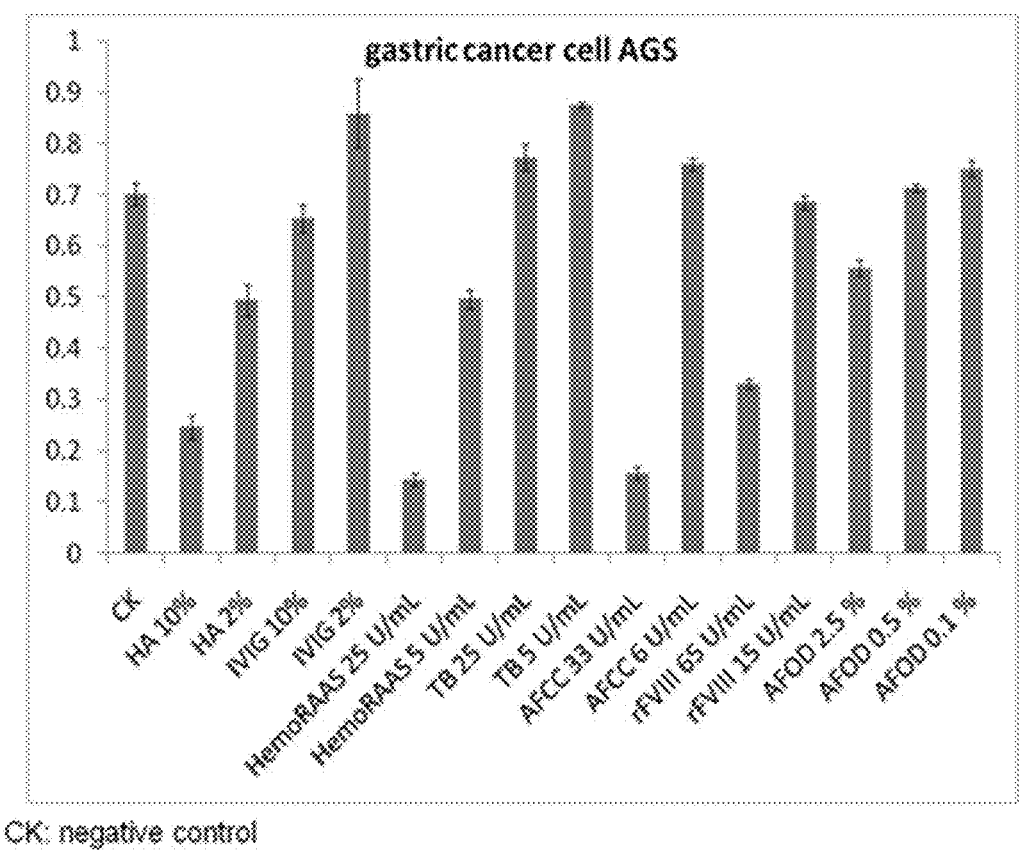
Figure 35:
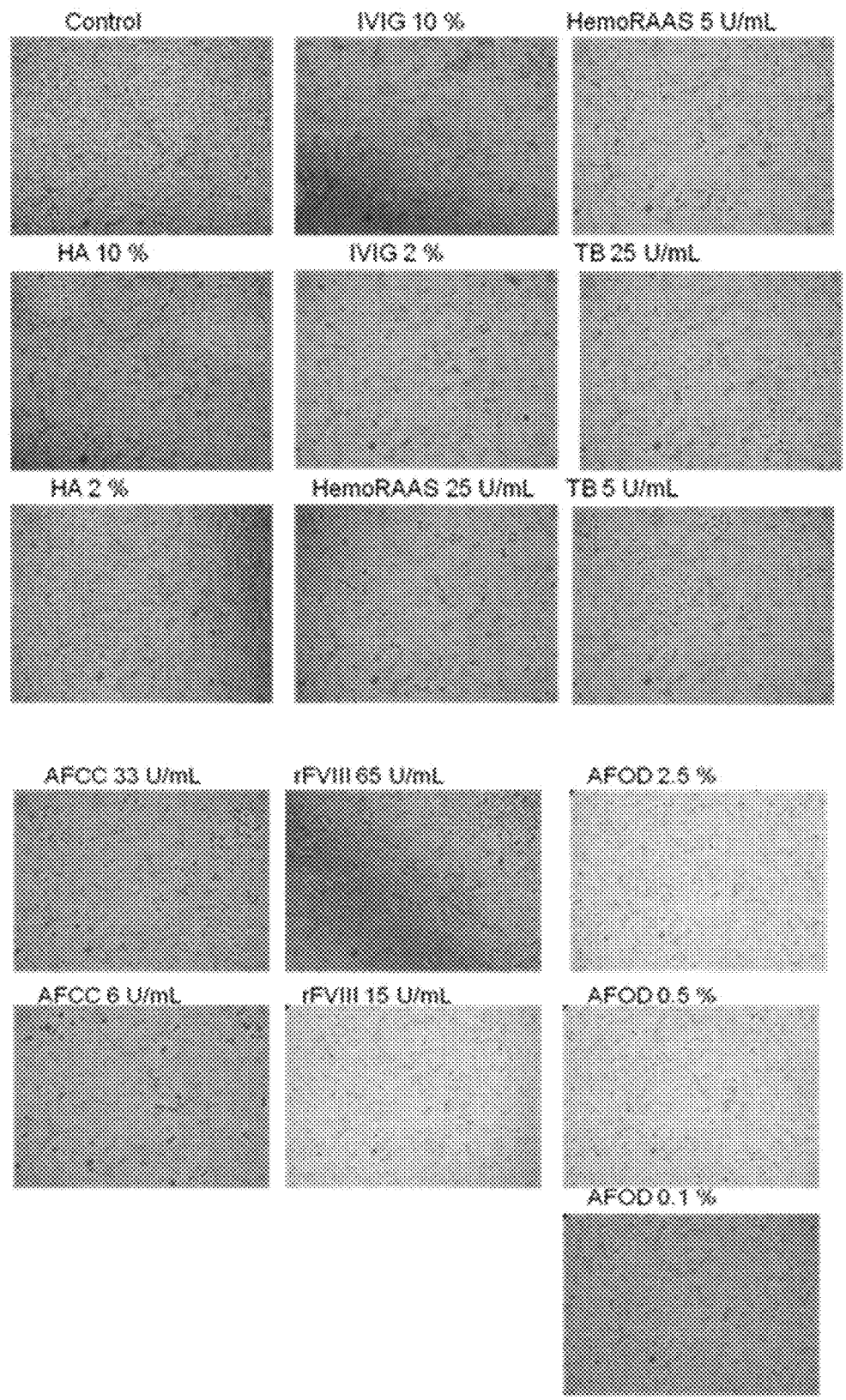
Figure 36:
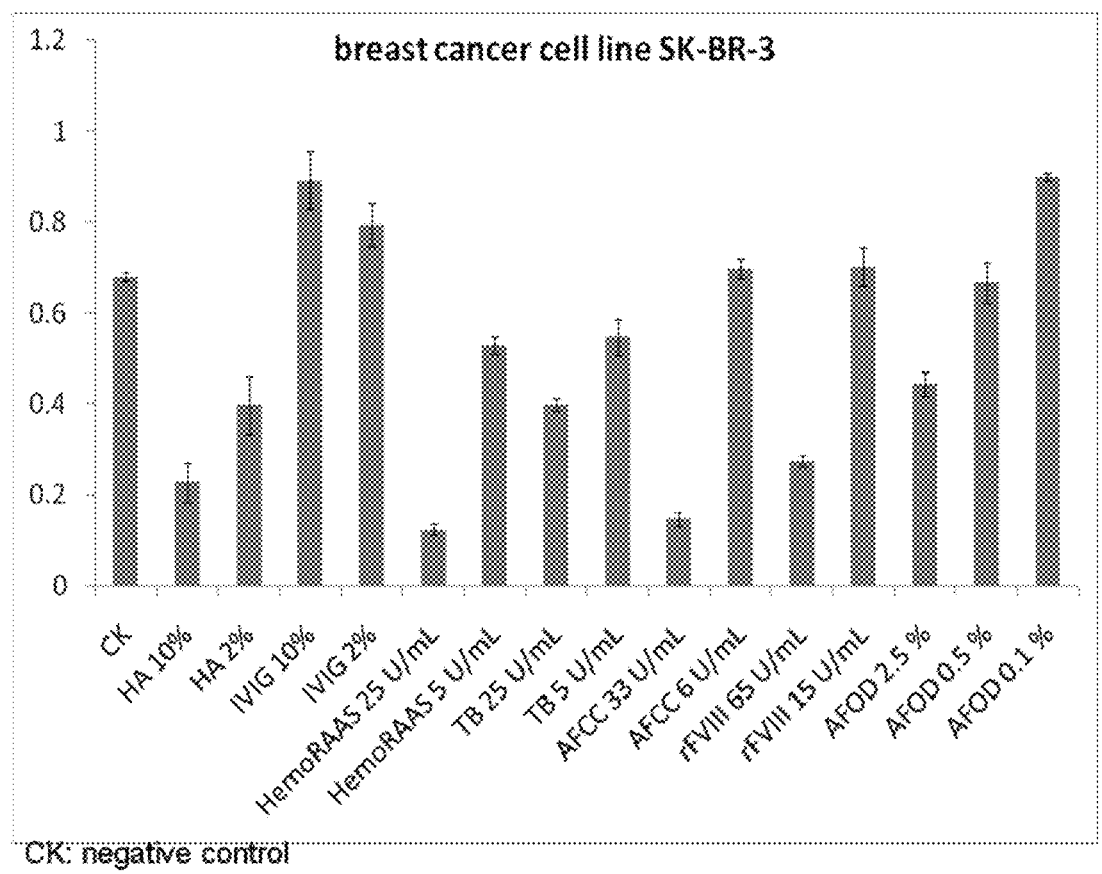
Figure 37:
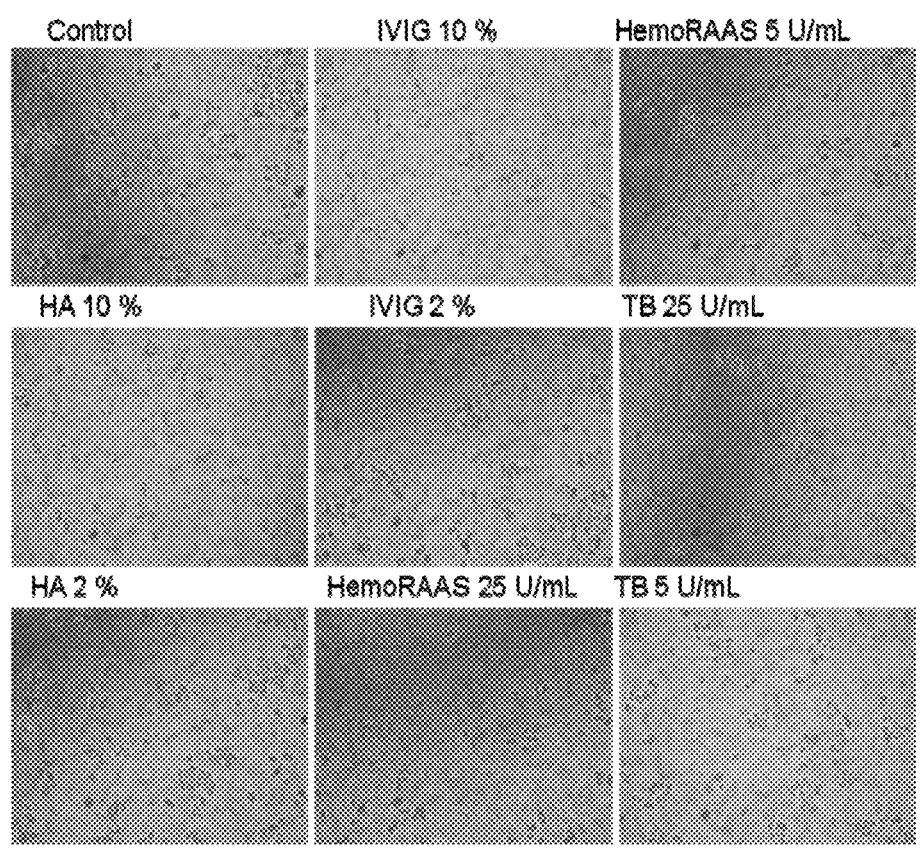
Figure 38:
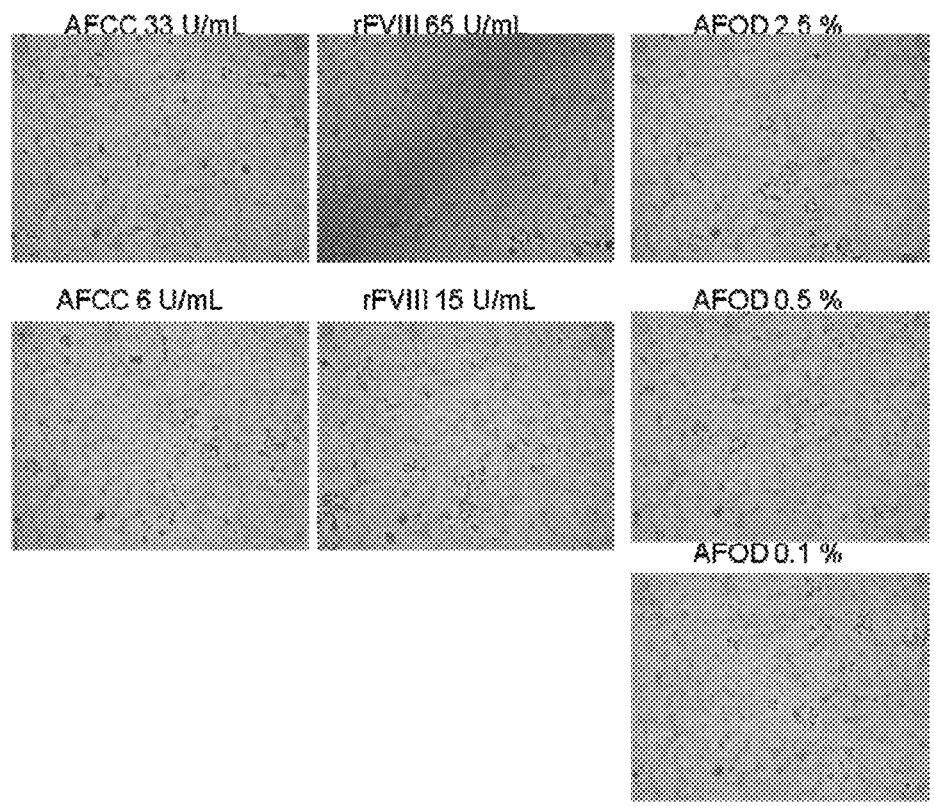
Figure 39:
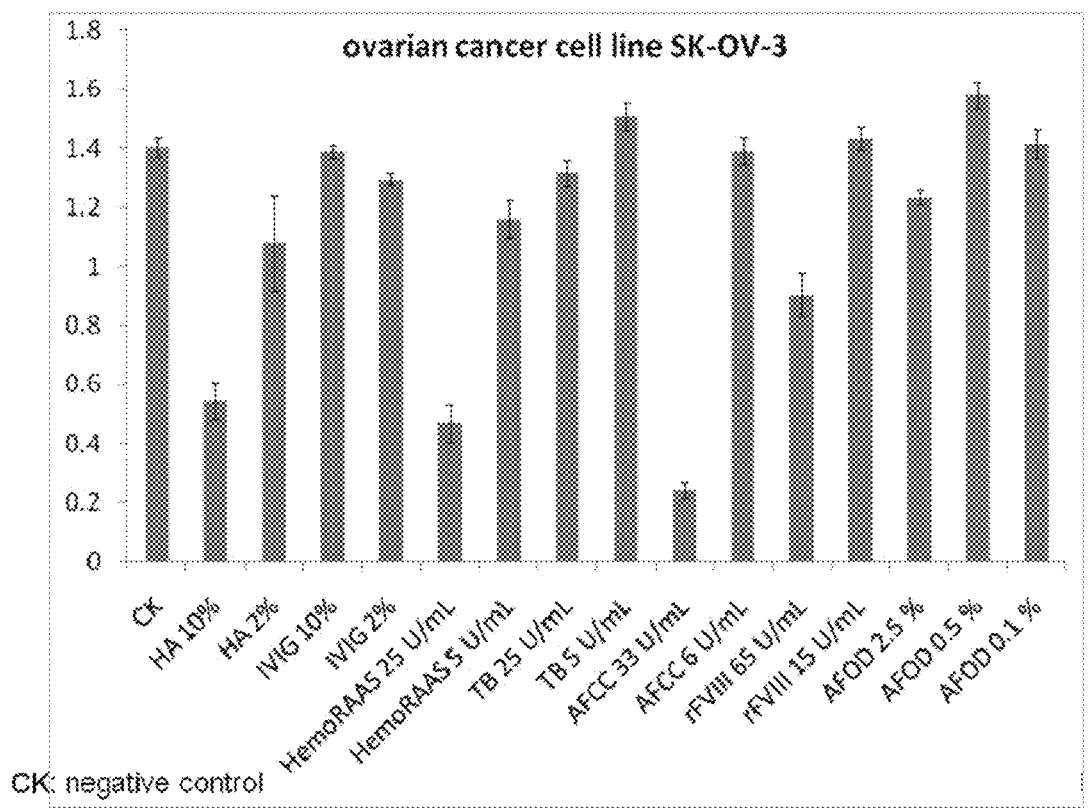
Figure 40:
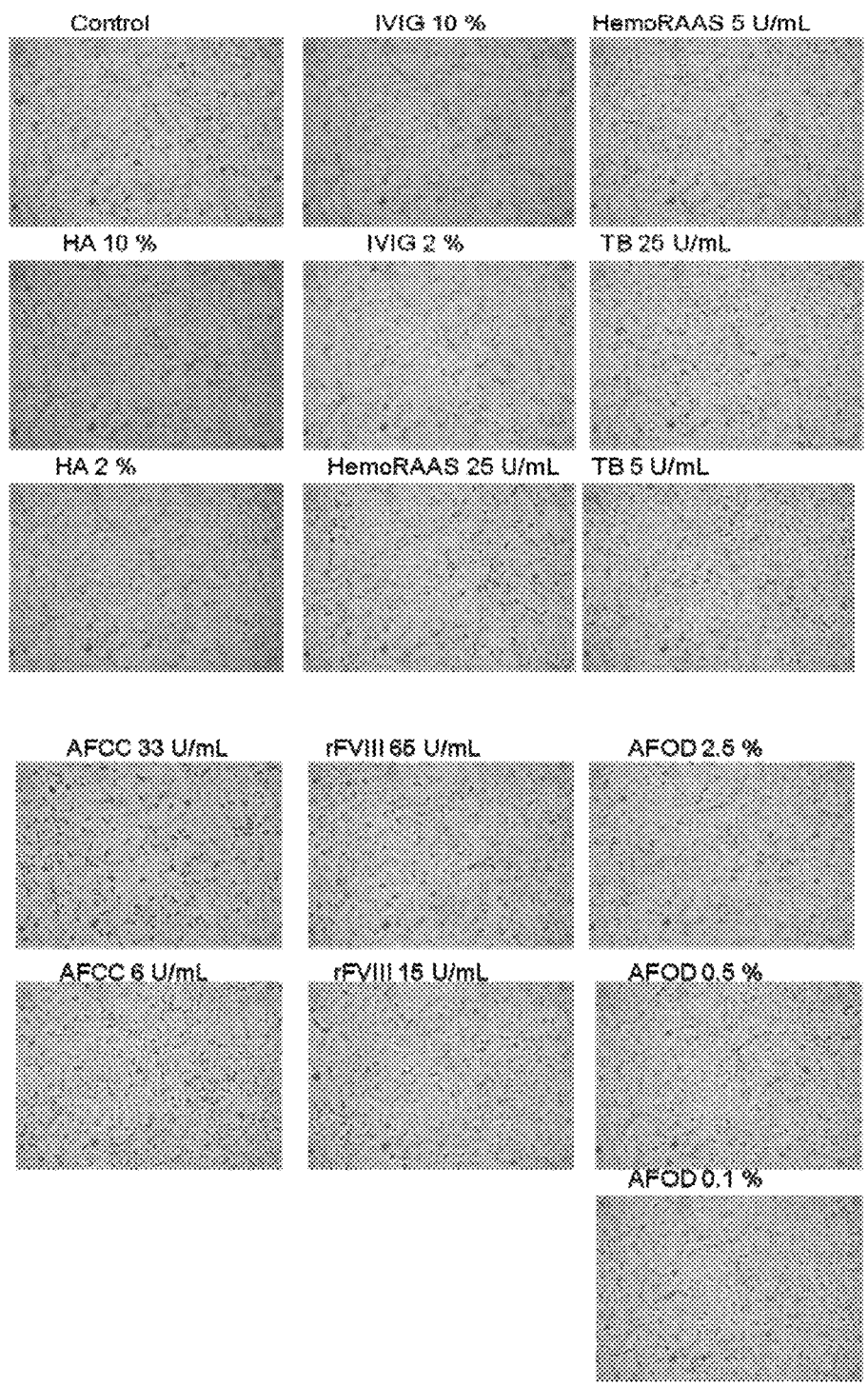
Figure 41:
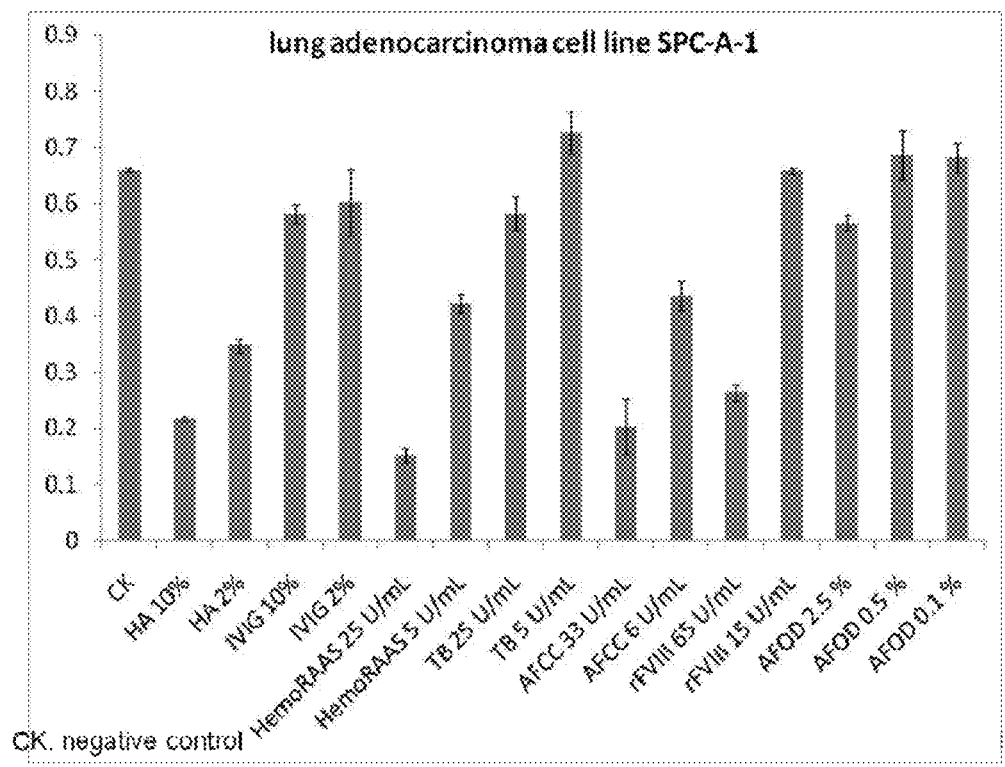
Figure 42:
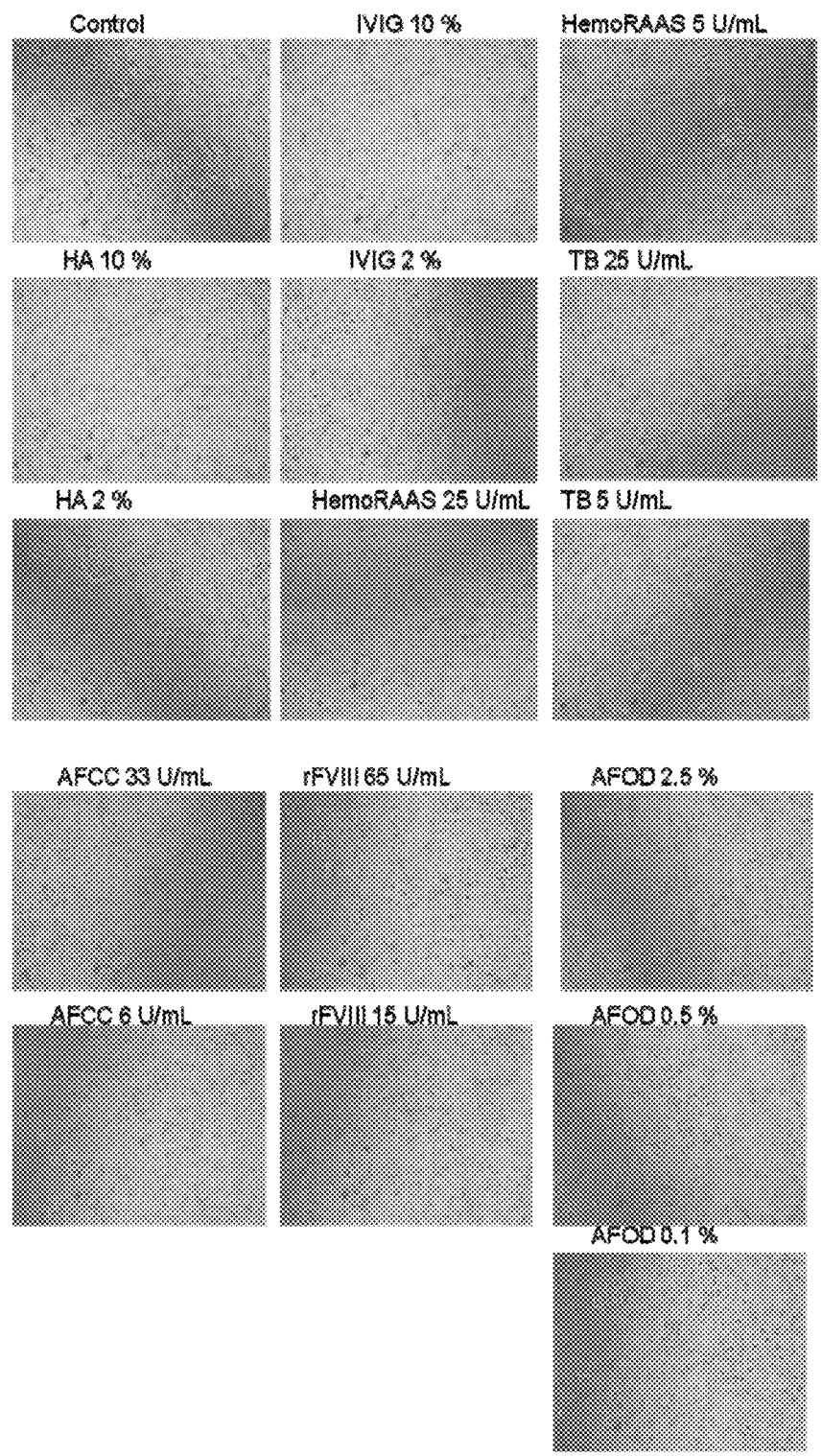
Figure 43:
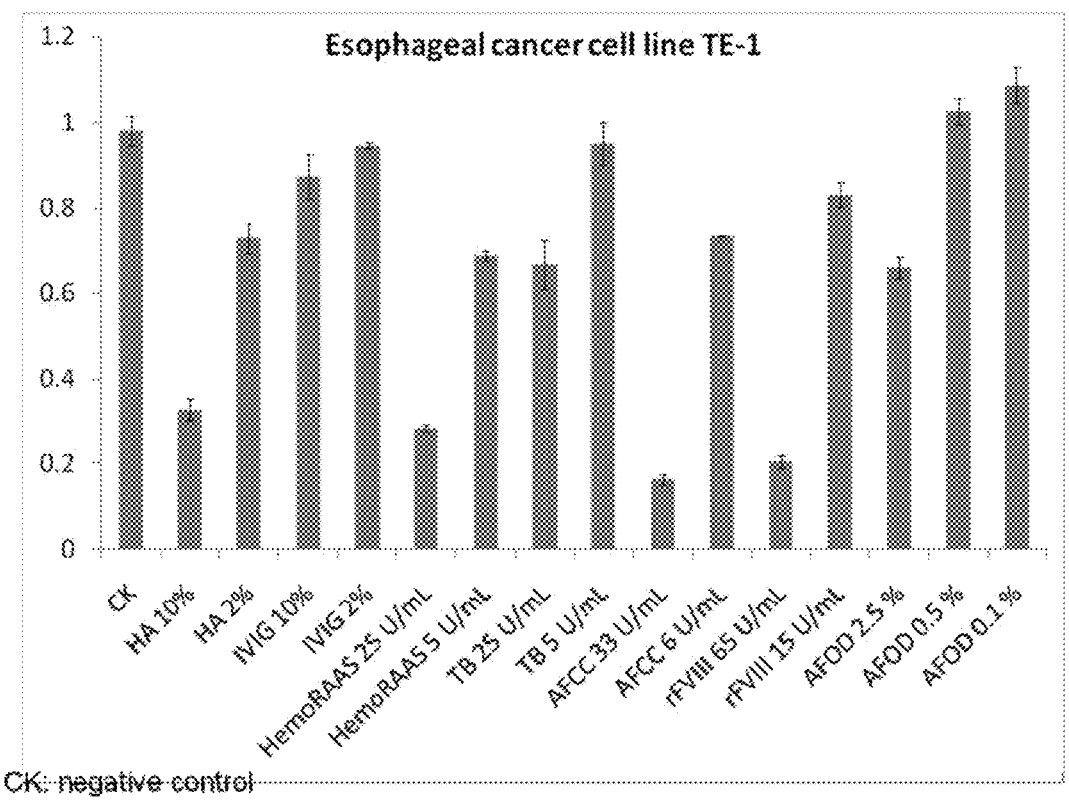
Figure 44:
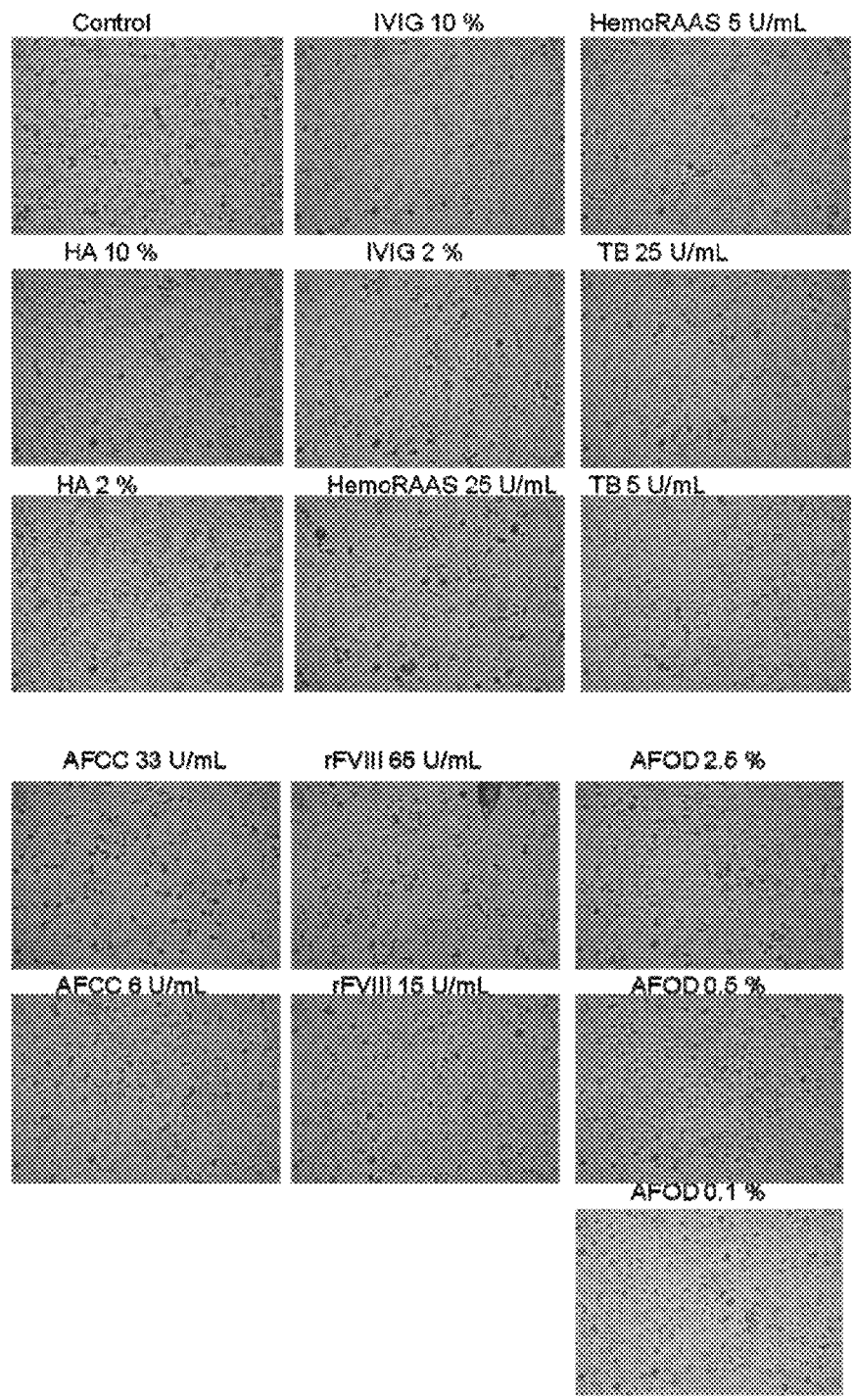
Figure 45:
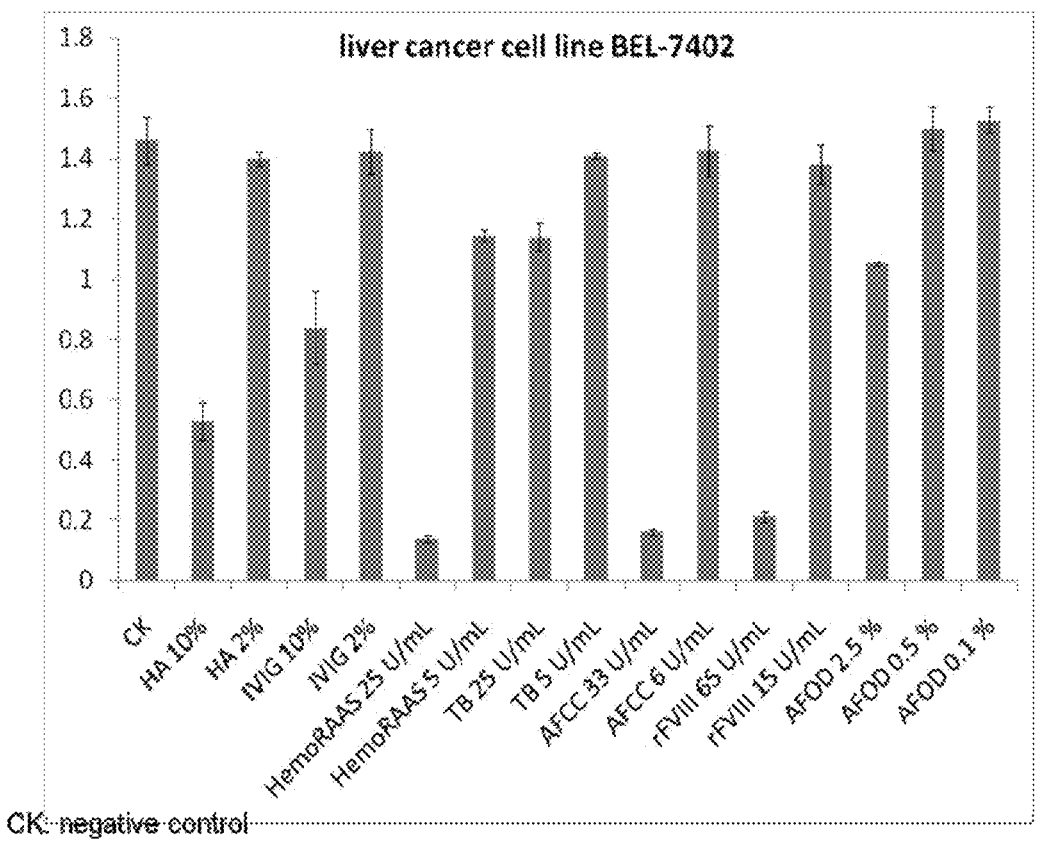
Figure 46:
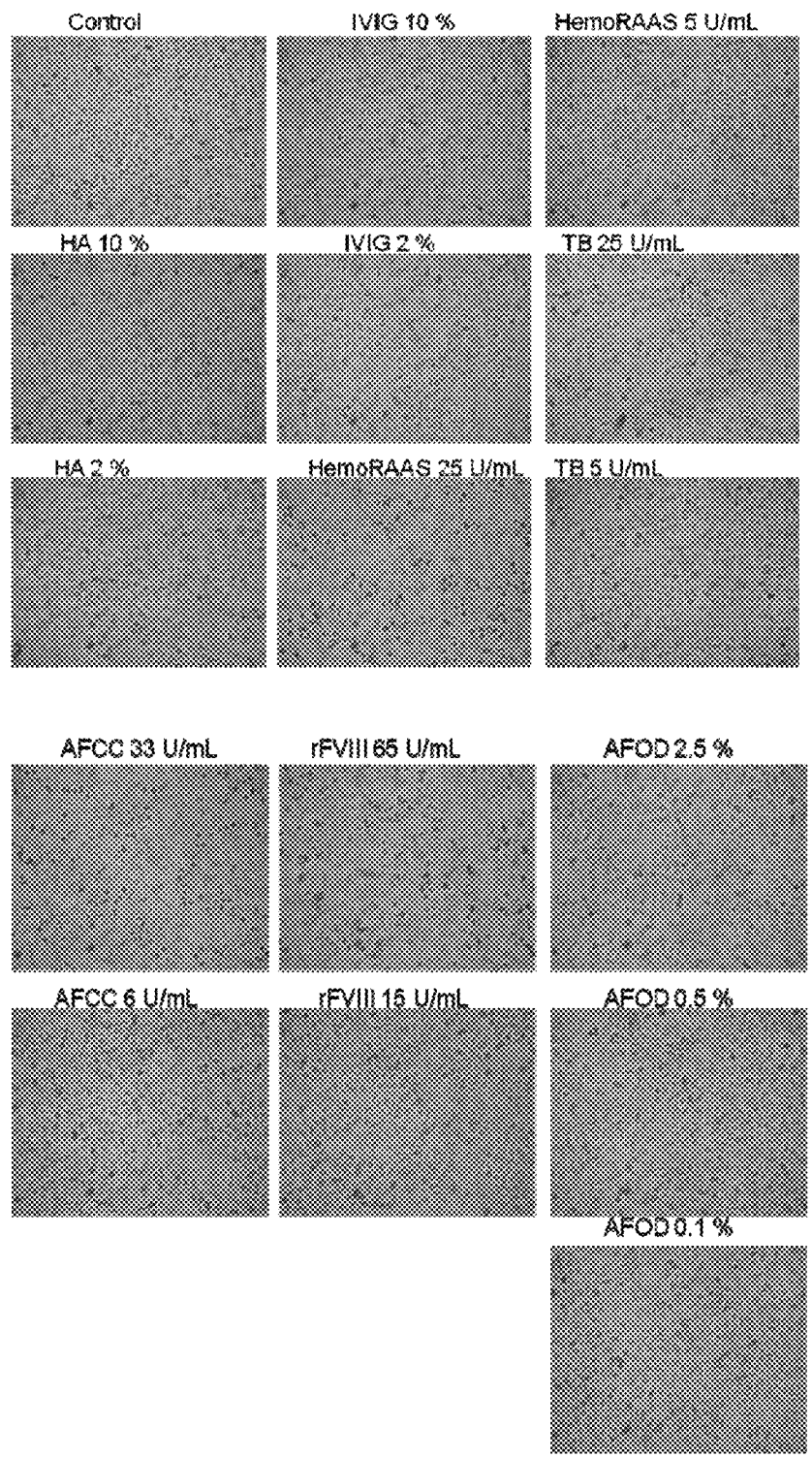
Figure 47:
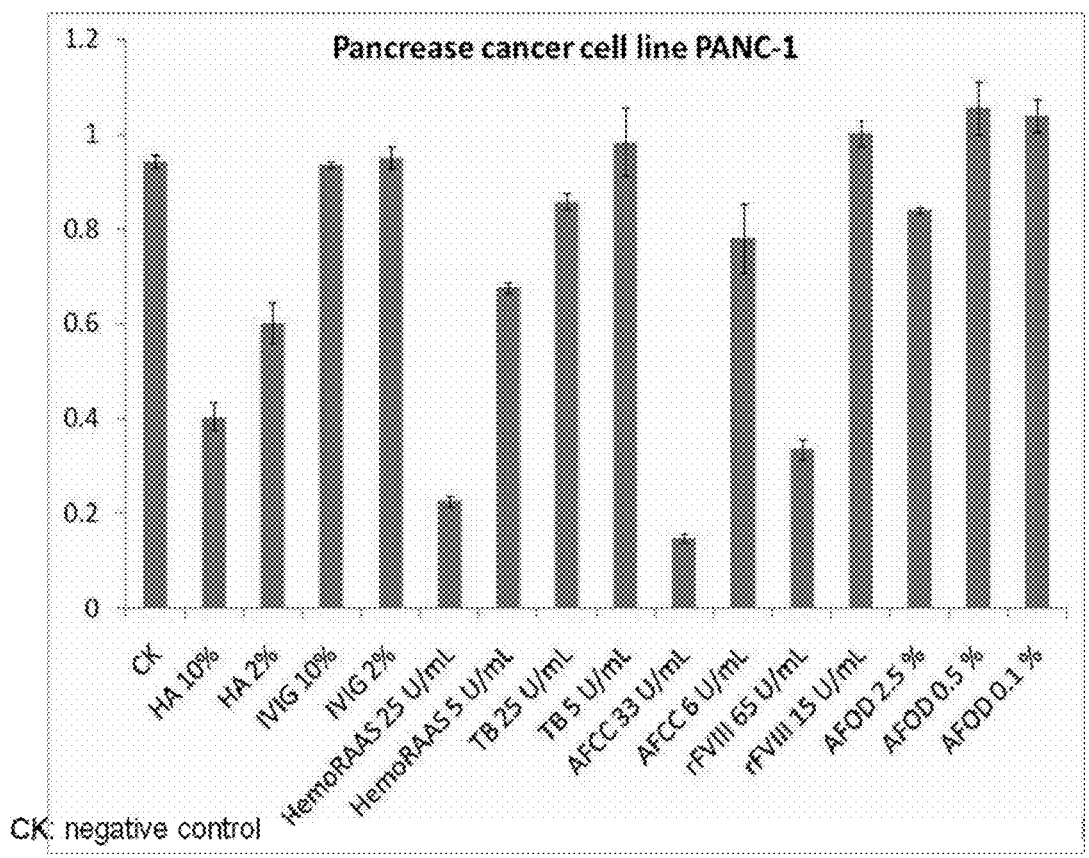
Figure 48:
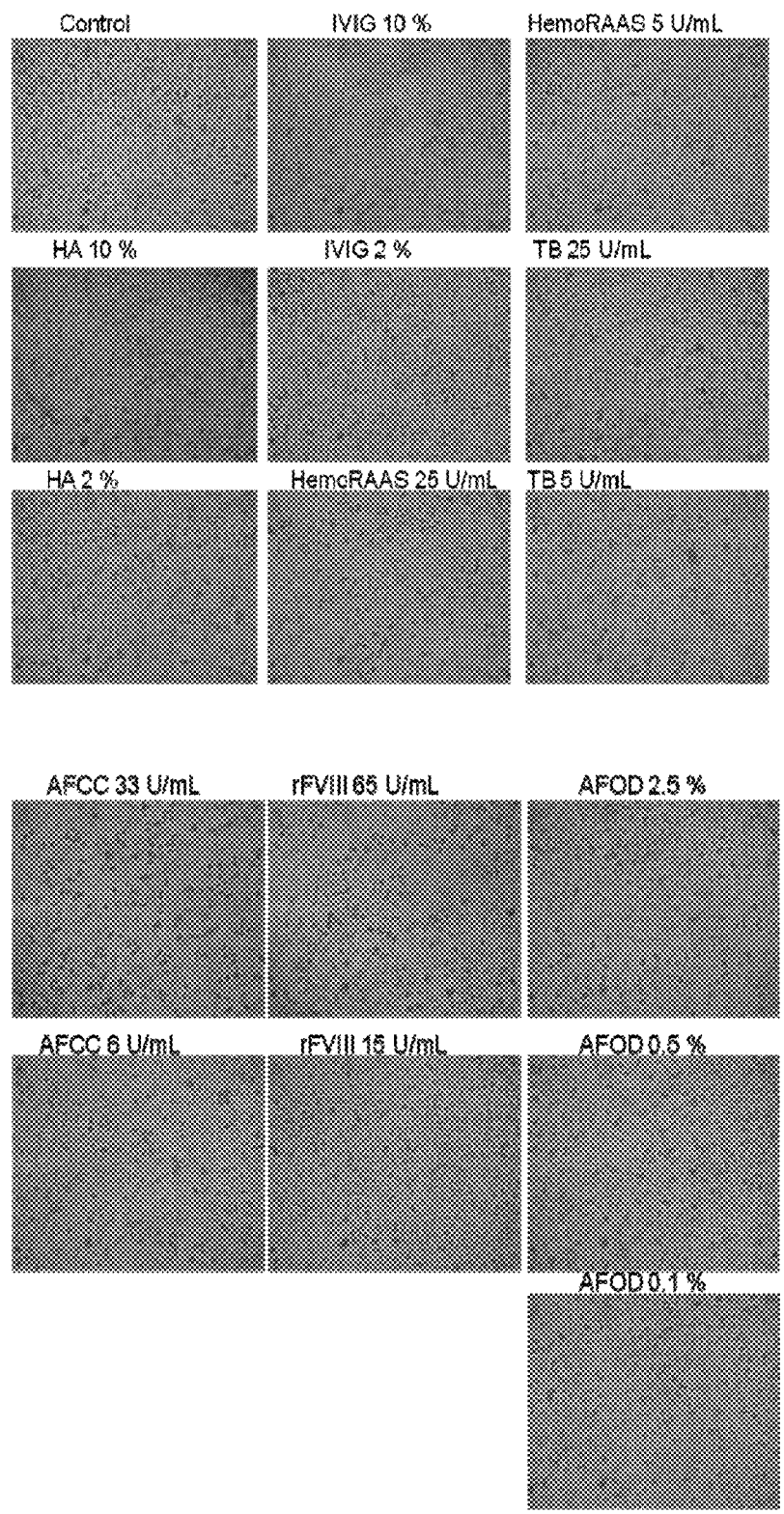
Figure 49:
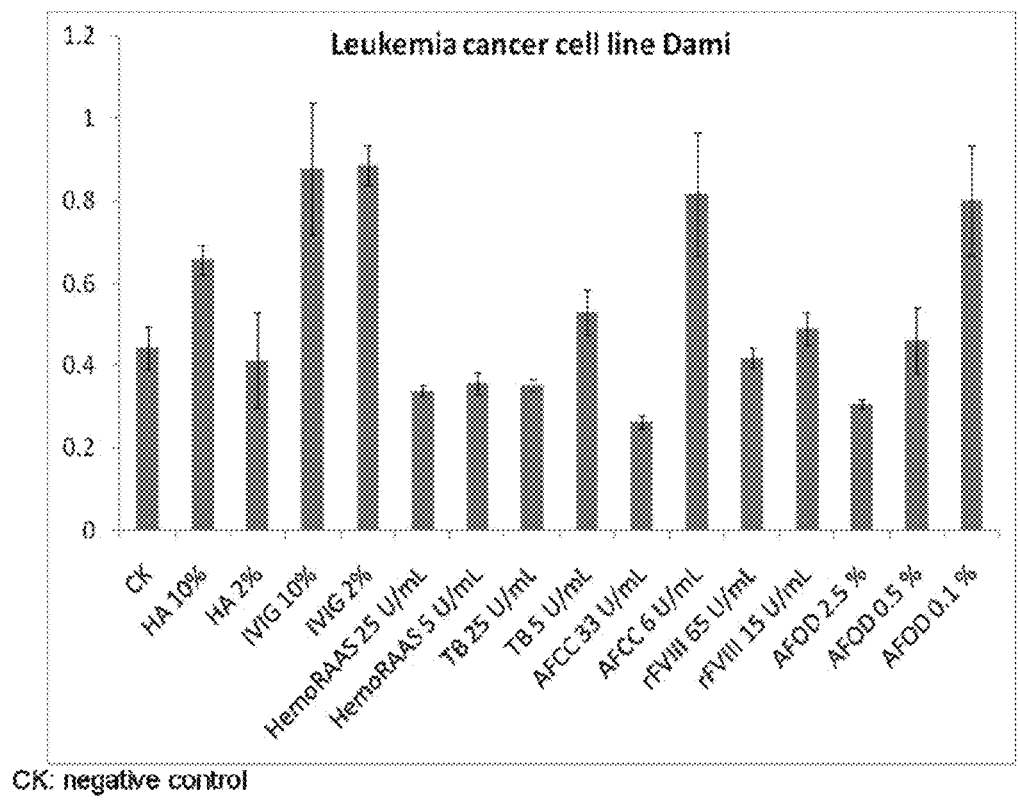
Figure 50:
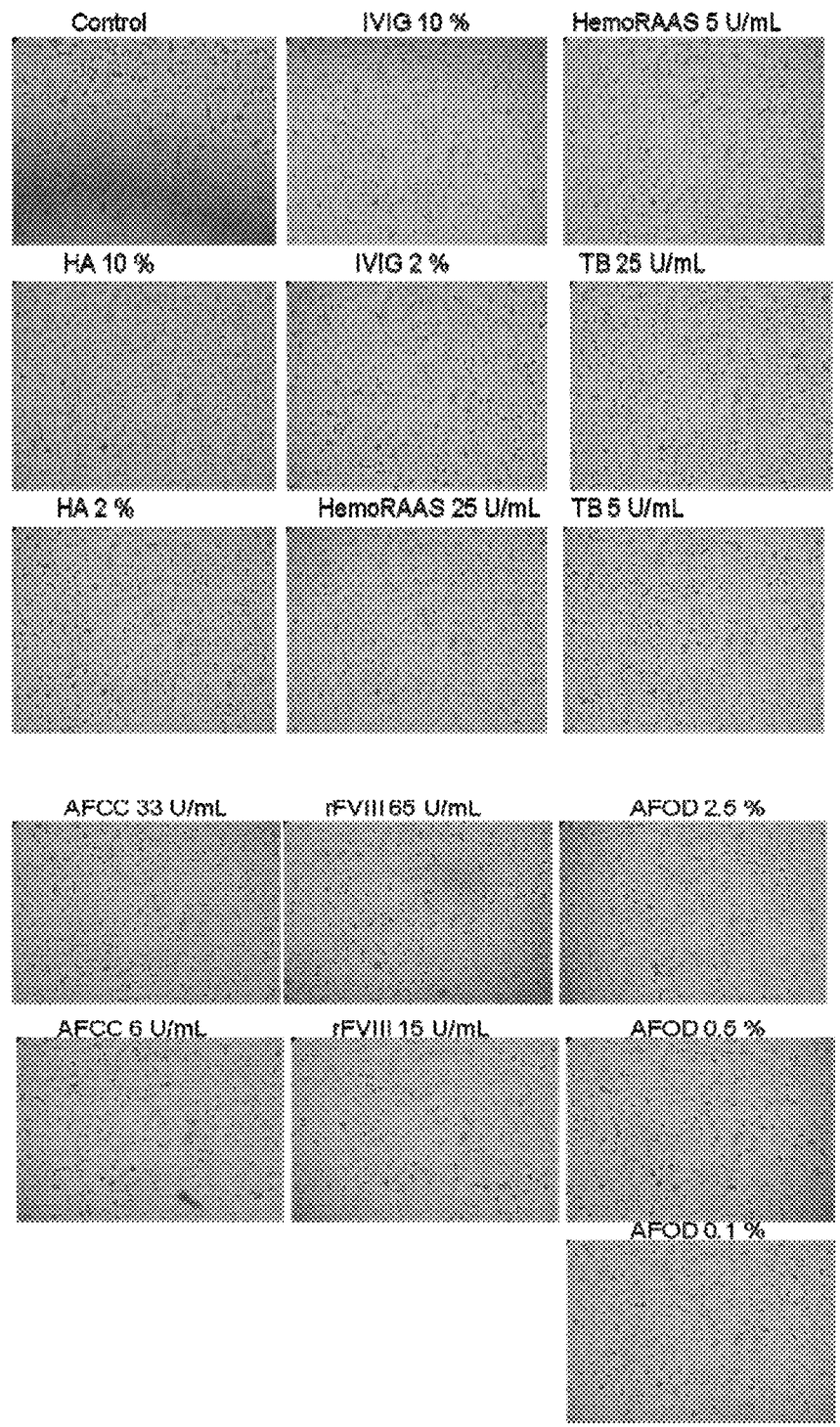
Figure 51:
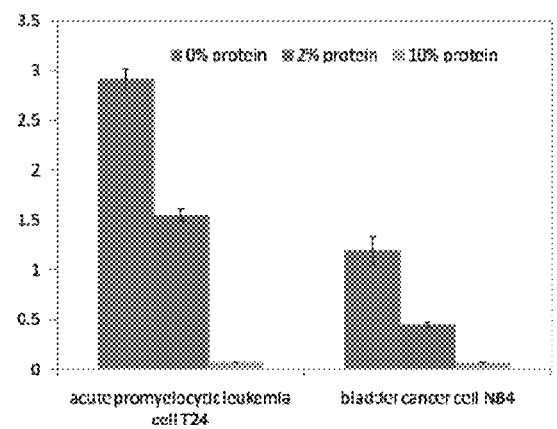

FIG. 33 contains 16 photographs taken on Day 3 after treatment, showing the proliferation of Cervical Cancer line Hela in the presence of 16 different solutions (listed on each photo). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 34 is a graph showing cell proliferation during a 3-day in vitro study of Gastric cancer cell AGS in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 35 contains 16 photographs taken on Day 3 after treatment, showing the proliferation of Gastric Cancer Cell AGS in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 36 is a graph showing cell proliferation during a 3-day in vitro study of Breast Cancer Cell Line SK-BR-3 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 37 contains 9 photos taken on Day 3 after treatment, showing the proliferation of Breast Cancer Cell Line SK-BR-3 in the presence of different solutions (listed on each photograph). The solutions are CK, HA 10%, HA 2%, IVIG 10%, IVIG 2%, HemoRAAS 25 U/mL, HemoRAAS 5 U/mL, TB 25 U/mL, and TB 5 U/mL;

FIG. 38 contains 7 photographs taken on Day 3 after treatment, showing the proliferation of Breast Cancer Cell Line SK-BR-3 in the presence of different solutions (listed on each photograph). The solutions are AFCC 33 U/mL, AFCC 6 U/mL, rFVIII 65 U/mL, rFVIII 15 U/mL, AFOD 2.5%, AFOD 0.5%. and AFOD 0.1%;

FIG. 39 is a graph showing cell proliferation during a 3-day in vitro study of Ovarian Cancer Cell Line SK-OV-3 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 40 contains 16 photographs taken on Day 3 after treatment, showing the proliferation of Ovarian Cancer Cell SK-OV-3 in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 41 is a graph showing cell proliferation during a 3-day in vitro study of Lung Adenocarcinoma Cell Line SPC-A-1 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 42 contains 16 photographs taken on Day 3 after treatment, showing the proliferation of Lung Adenocarcinoma Cell Line SPC-A-1 in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 43 is a graph showing cell proliferation during a 3-day in vitro study of Espohageal Cancer Cell Line TE-1 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 44 contains 16 photographs taken on Day 3 after treatment, showing the proliferation of Espohageal Cancer Cell Line TE-1 in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 45 is a graph showing cell proliferation during a 3-day in vitro study of Liver Cancer Cell Line BEL-7402 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 46 contains 16 photographs taken on Day 3 after treatment, showing the proliferation of Liver Cancer Cell Line BEL-7402 in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 47 is a graph showing cell proliferation during a 3-day in vitro study of Pancreas Cancer Cell Line PANC-1 in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 48 contains 16 photographs taken on Day 3 after treatment, showing the proliferation of Pancreas Cancer Cell Line PANC-1 in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 49 is a graph showing cell proliferation during a 3-day in vitro study of Leukemia Cancer Cell Line Dami in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 50 contains 16 photographs taken on Day 3 after treatment, showing the proliferation of Leukemia Cancer Cell Line Dami in the presence of 16 different solutions (listed on each photograph). The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%;

FIG. 51 is a graph showing the summary data for the proliferation of Leukemia Cells (Acute Promyelocytic Leukemia Cell T24) in the presence of 0% protein, 2% protein, and 10% protein of AFOD, and Bladder Cancer cells (Bladder Cancer Cell NB4) in the presence of 0% protein, 2% protein, and 10% protein of AFOD during the 3-day trial period.

Figure 52:
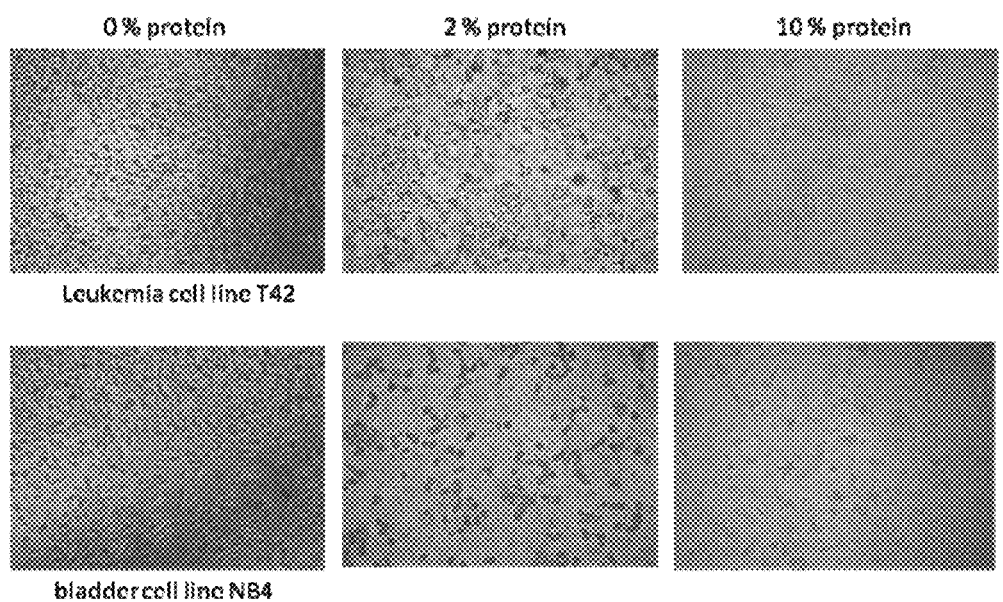

FIG. 52 shows 6 pictures taken after the trial which show the proliferation of Leukemia Cells (Acute Promyelocytic Leukemia Cell T24) in the presence of 0% protein, 2% protein, and 10% protein of AFOD, and Bladder Cancer cells (Bladder Cancer Cell NB4) in the presence of 0% protein, 2% protein, and 10% protein of AFOD during the 3-day trial period.

Figures 53, 54:
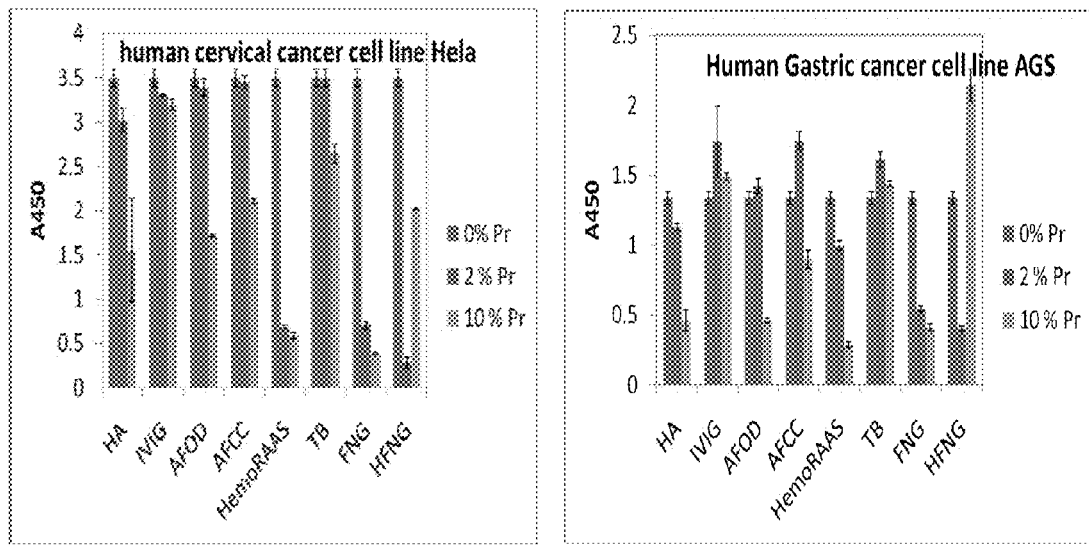

FIG. 53 is a graph showing the summary data for the proliferation of Cervical Cancer Cells (Human Cervical Cancer Cell Line Hela) in the presence of a variety of solutions, listed on the x-axis, at 0%, 2%, and 10% concentrations of protein, respectively.

FIG. 54 is a graph showing the summary data for the proliferation of Gastric Cancer Cells (Human Gastric Cancer Cell Line AGS) in the presence of a variety of solutions, listed on the x-axis, at 0%, 2%, and 10% concentrations of protein, respectively.

Figures 55, 56:
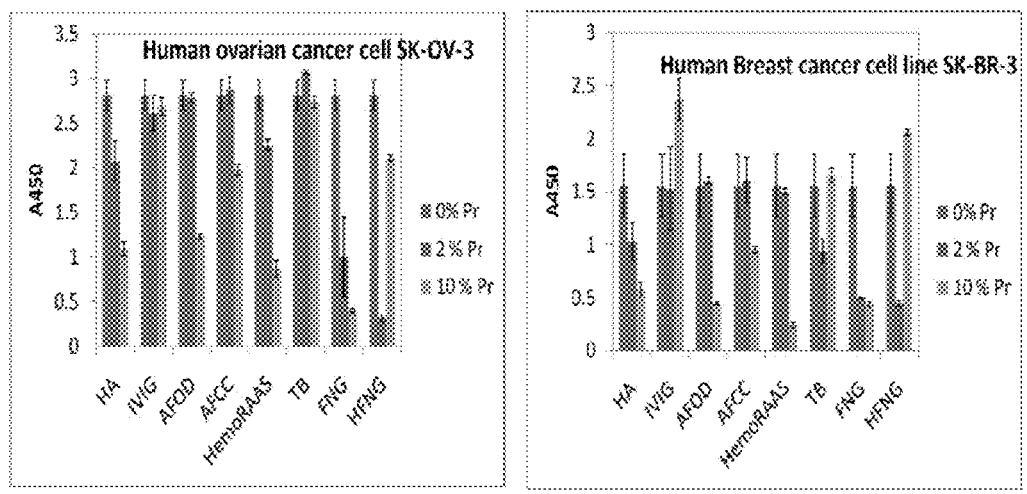

FIG. 55 is a graph showing the summary data for the proliferation of Ovarian Cancer Cells (Human Ovarian Cancer Cell SK-OV-3) in the presence of a variety of solutions, listed on the x-axis, at 0%, 2%, and 10% concentrations of protein, respectively.

FIG. 56 is a graph showing the summary data for the proliferation of Breast Cancer Cells (Human Breast Cancer Cell Line SK-BR-3) in the presence of a variety of solutions, listed on the x-axis, at 0%, 2%, and 10% concentrations of protein, respectively.

Figures 57, 58:
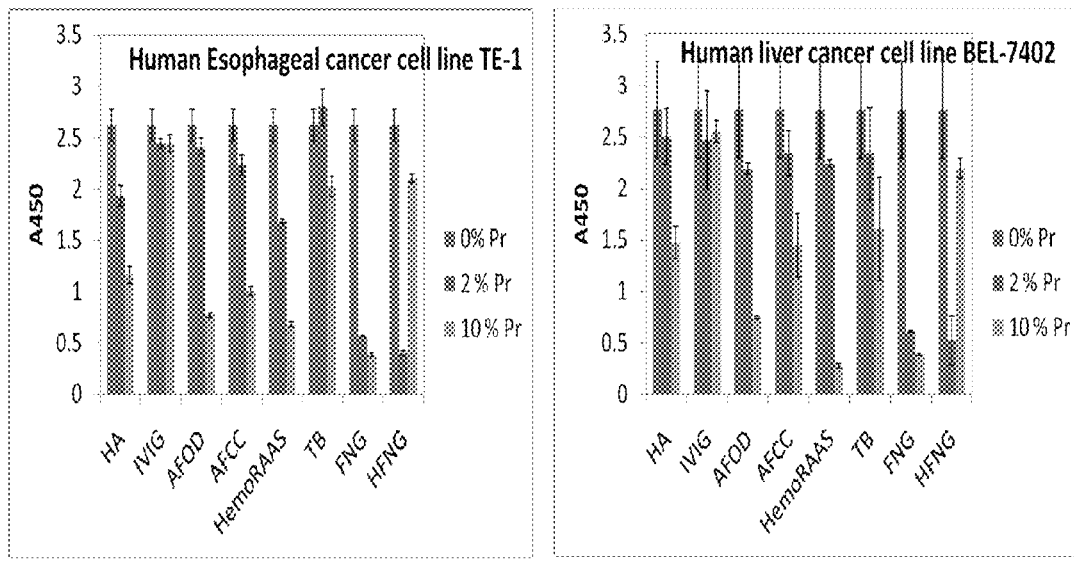

FIG. 57 is a graph showing the summary data for the proliferation of Esophageal Cancer Cells (Human Esophageal Cancer Cell Line TE-1) in the presence of a variety of solutions, listed on the x-axis, at 0%, 2%, and 10% concentrations of protein, respectively.

FIG. 58 is a graph showing the summary data for the proliferation of Liver Cancer Cells (Human Liver Cancer Cell Line BEL-7402) in the presence of a variety of solutions, listed on the x-axis, at 0%, 2%, and 10% concentrations of protein, respectively.

Figures 59, 60:
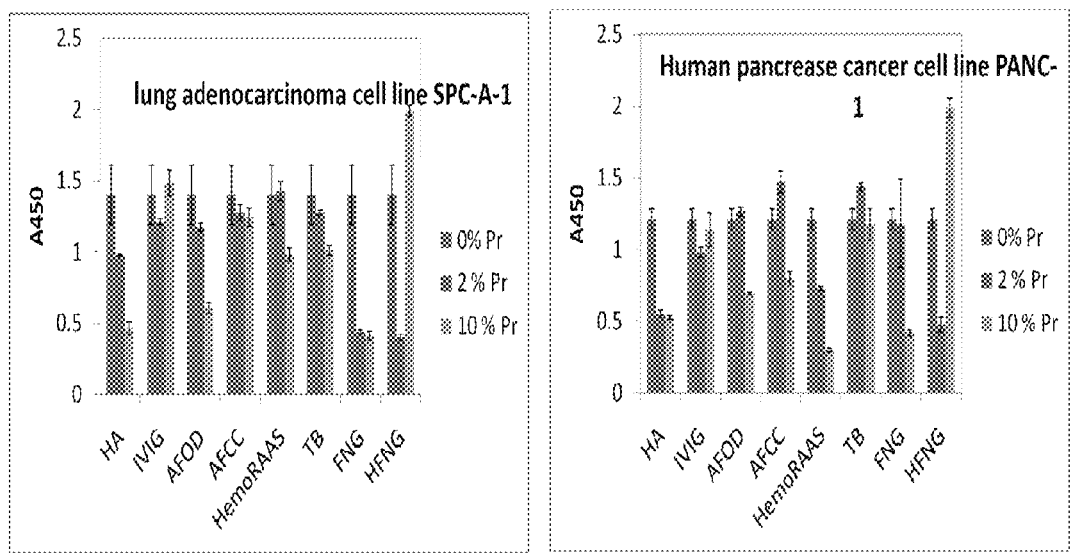

FIG. 59 is a graph showing the summary data for the proliferation of Lung Cancer Cells (Lung Adenocarcinoma Cell Line SPC-A-1) in the presence of a variety of solutions, listed on the x-axis, at 0%, 2%, and 10% concentrations of protein, respectively.

FIG. 60 is a graph showing the summary data for the proliferation of Pancreas Cancer Cells (Human Pancreas Cancer Cell Line PANC-) in the presence of a variety of solutions, listed on the x-axis, at 0%, 2%, and 10% concentrations of protein, respectively.

Figure 61:
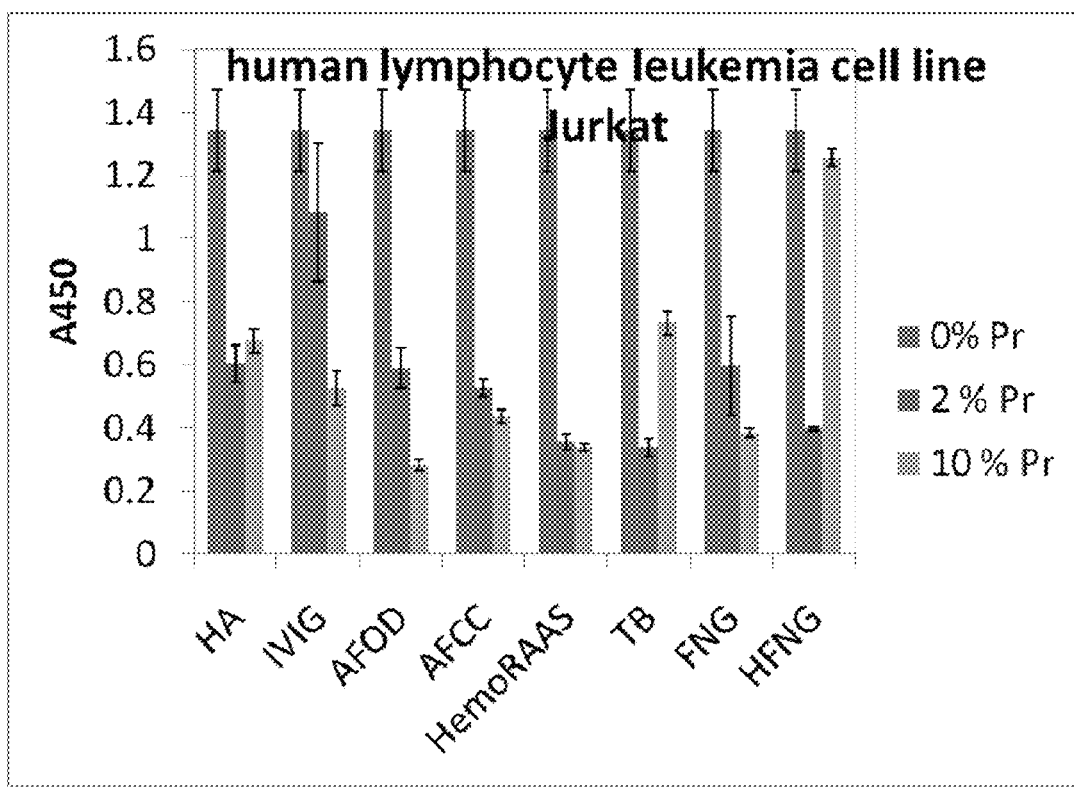

FIG. 61 is a graph showing the summary data for the proliferation of Leukemia Cells (Human Lymphocyte Leukemia Cell Line Jurkat) in the presence of a variety of solutions, listed on the x-axis, at 0%, 2%, and 10% concentrations of protein, respectively.

Figure 62:
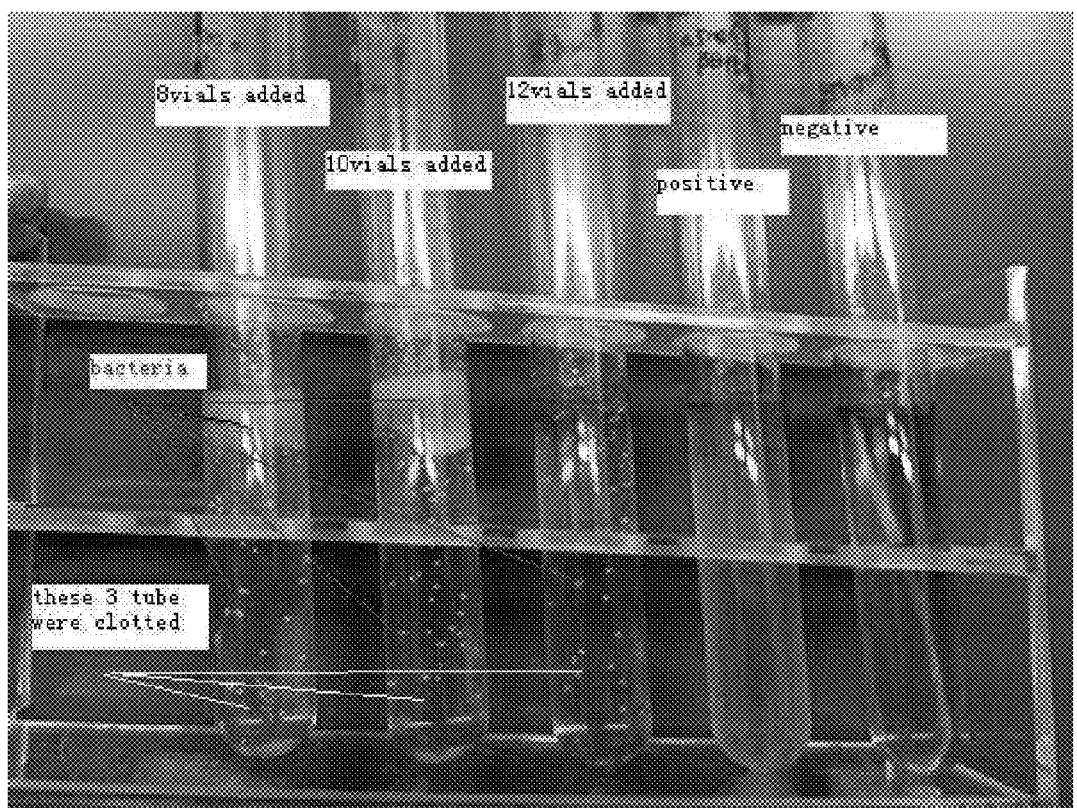

FIG. 62 is a photograph of five sample vials of bacteria during a microbe test with AFOD RAAS 1 on *Staphylococcus aureus*, from left to right, having 8 mL AFOD added, having 10 mL AFOD added, having 12 mL AFOD added, a positive control, and a negative control.

Figure 63:
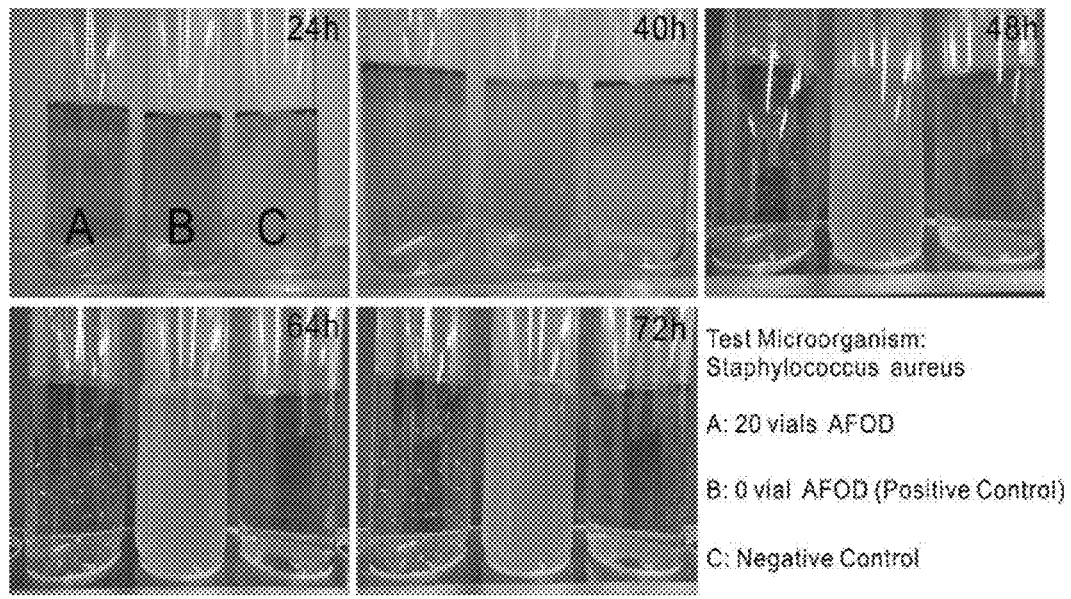

FIG. 63 is a series of photographs of three sample vials of bacteria, taken at different times during a microbe test of AFOD on *Staphylococcus aureus*.

Figure 64:
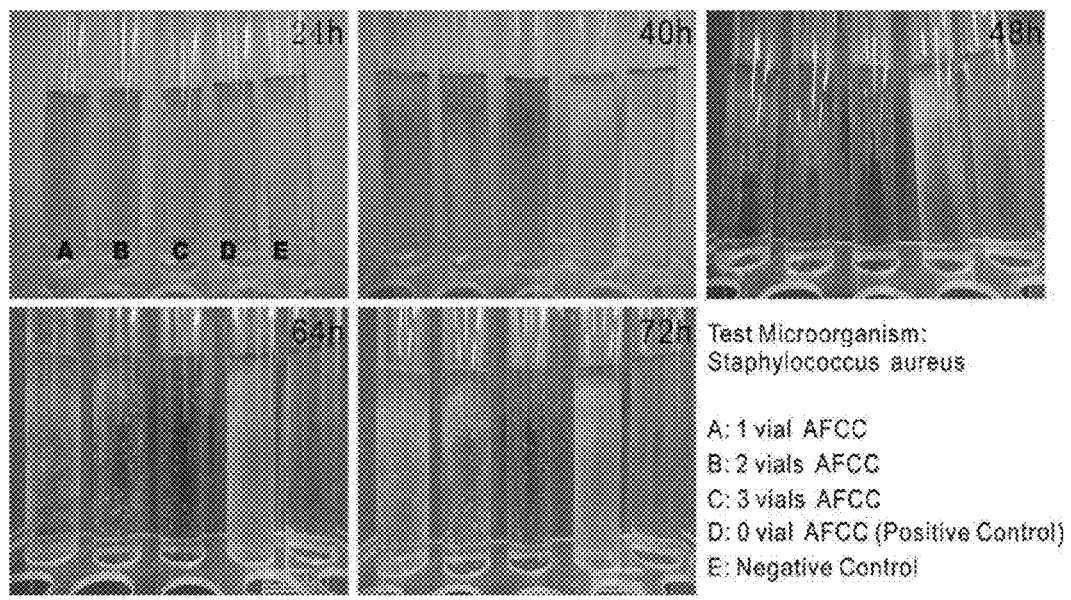

FIG. 64 is a series of photographs of five sample vials of bacteria, taken at different times during a microbe test of AFCC on *Staphylococcus aureus*.

Figure 65:
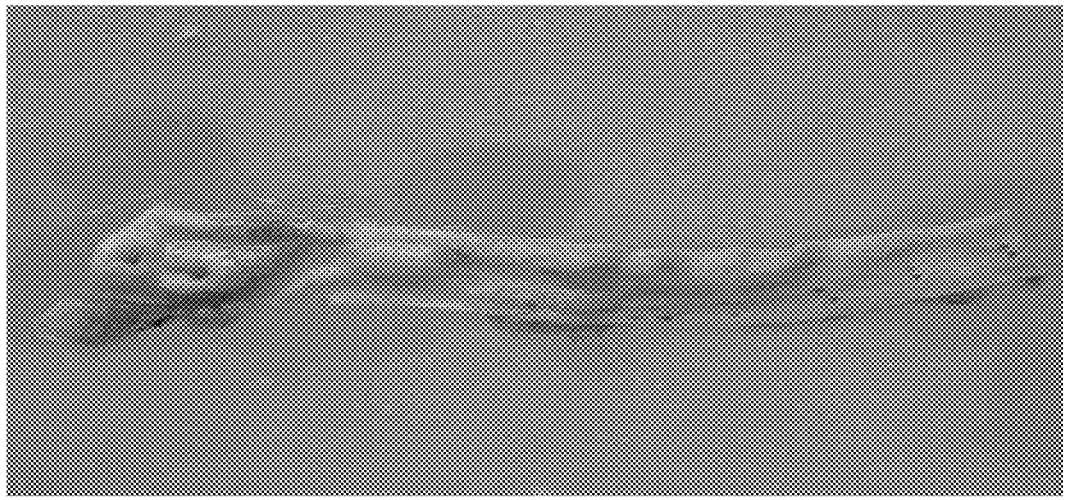

FIG. 65 is a photograph showing the aorta of a lab animal given a high fat diet after 10 weeks, with a plaque area of 24.3%.

Figure 66:
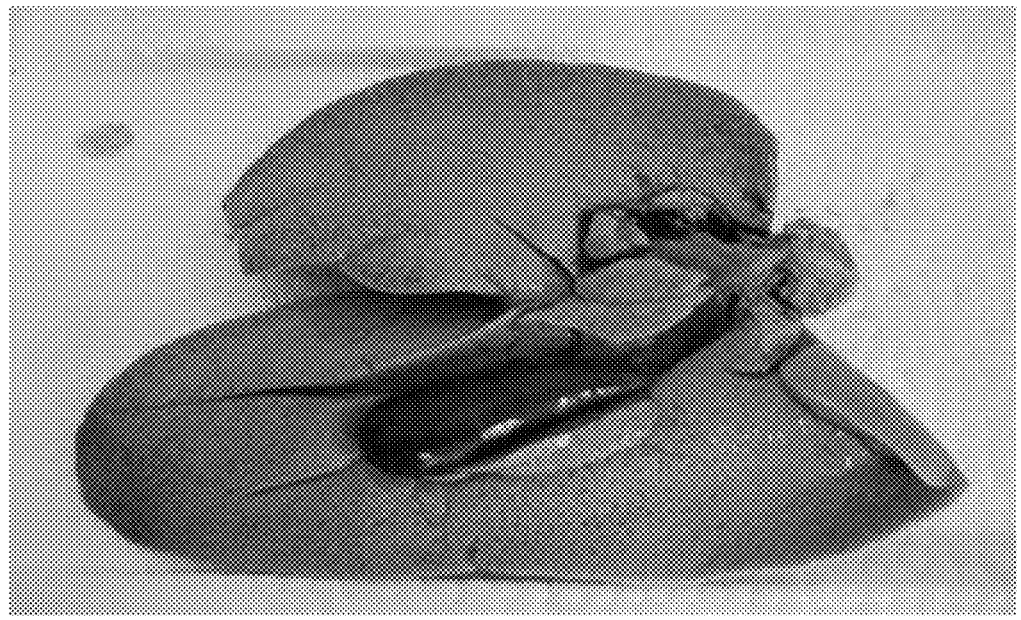

FIG. 66 is a photograph showing the liver tissue (with fat deposits) of a lab animal after 10 weeks of a high fat diet.

Figure 67:
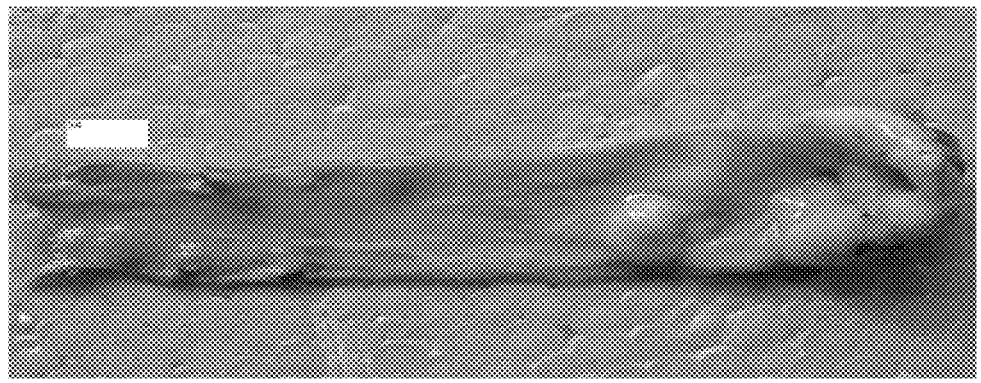

FIG. 67 is a photograph showing the aorta of a lab animal without AFOD RAAS 1 and then a normal diet for 4 weeks, with a plaque area of 45.3%.

Figure 68:
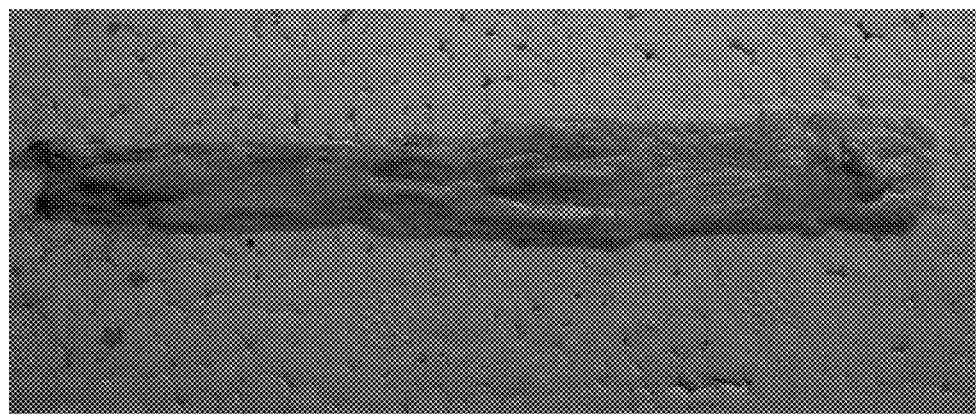

FIG. 68 is a photograph showing the aorta of a lab animal without AFOD RAAS 1 and then a normal diet for 8 weeks, with a plaque area of 98.5%.

Figure 69:
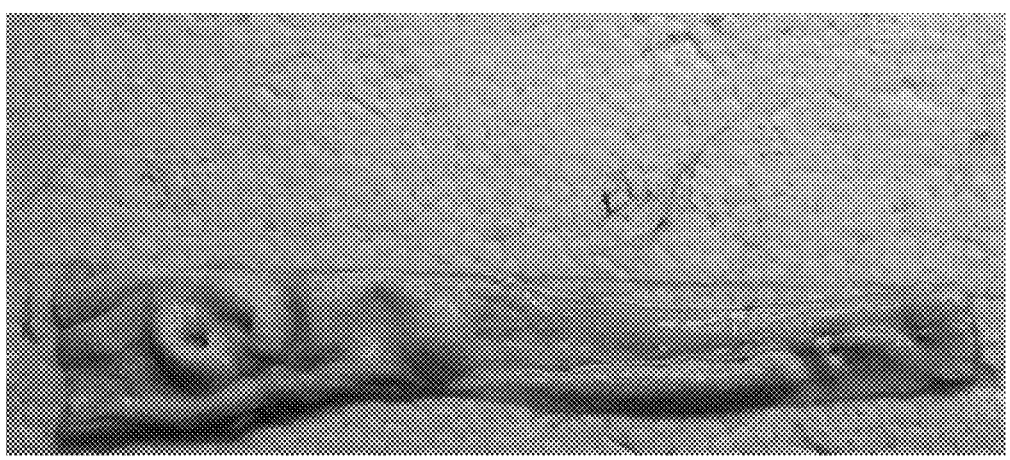
Figure 70:
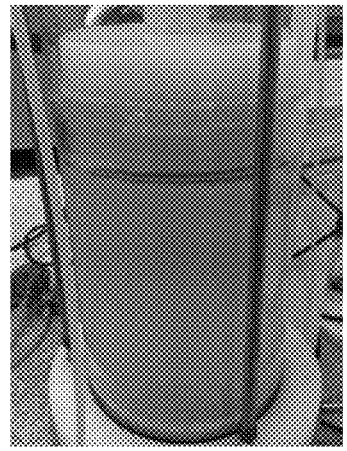
Figure 71:
Figure 72:
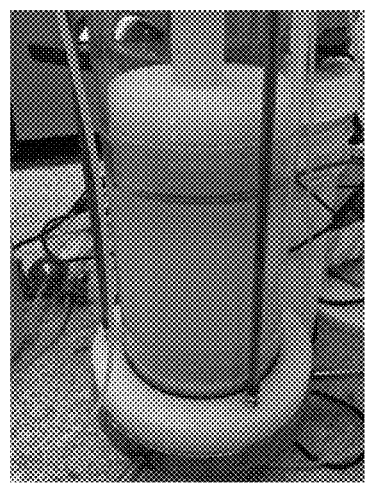
Figure 73:
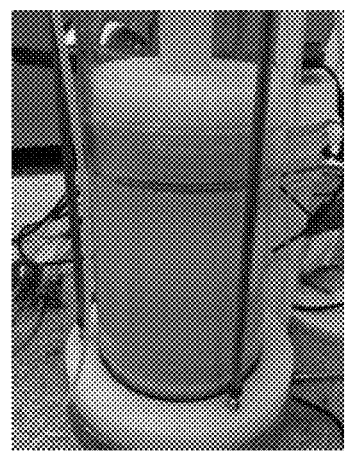
Figure 74:
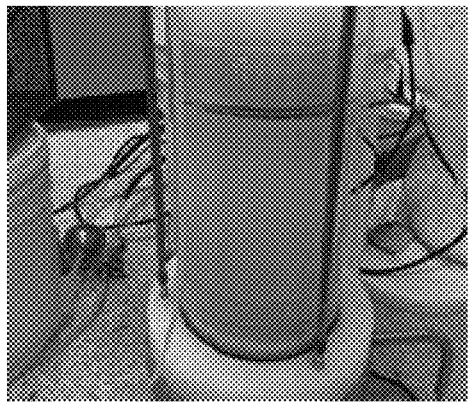
Figure 75:
Figure 76:

FIG. 69 is a photograph showing the aorta of a lab animal without AFOD RAAS 1 and then a normal diet for 8 weeks, with a plaque area of 78.94%.

Each of FIGS. 70-76 is a photograph of a container having a mixture of a product with a yellow color and a product with a blue that, unlike yellow and blue chemicals, will not turn green.

Figure 77:
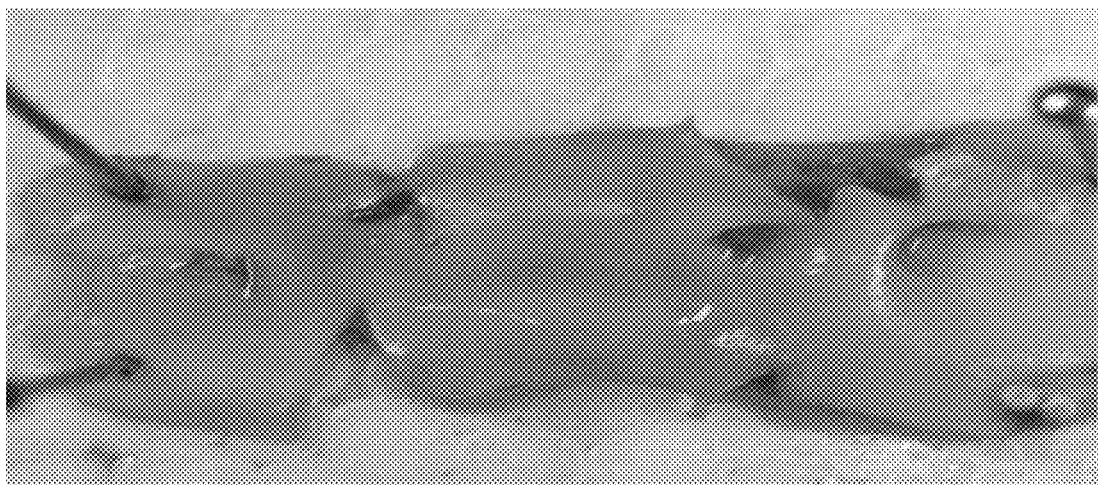

FIG. 77 is a photograph showing an artery of a lab animal is given a normal diet for 8 weeks.

Figure 78:
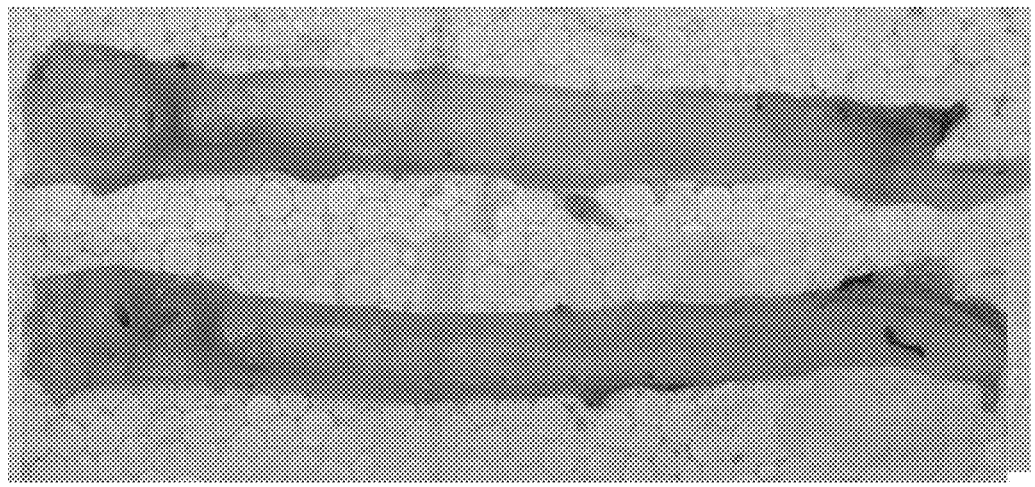

FIG. 78 is a photograph showing the aortas of two lab animals tested by AFOD RAAS 1, the aortas having a plaque area of 0.

Figure 79:
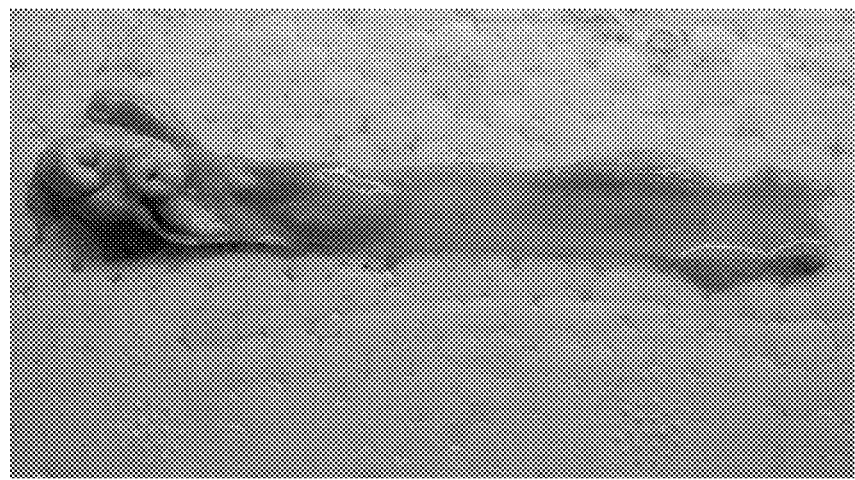

FIG. 79 is a photograph showing the buildup of plaque to a plaque area of 13.29% in the aorta of a lab animal with AFOD RAAS 1-A1 for 8 weeks.

Figure 80:
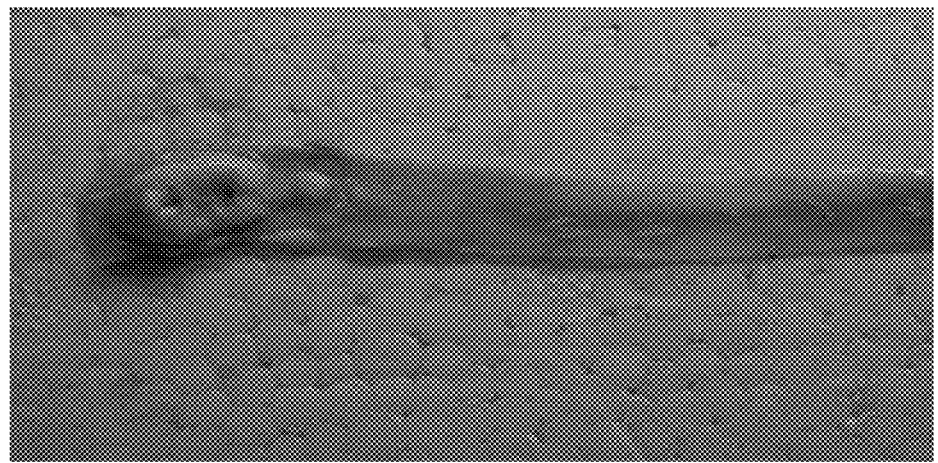

FIG. 80 is a photograph showing the buildup of plaque to a plaque area of 20.5% in the aorta of a lab animal with AFOD RAAS 1-A1 for 8 weeks.

Figure 81:
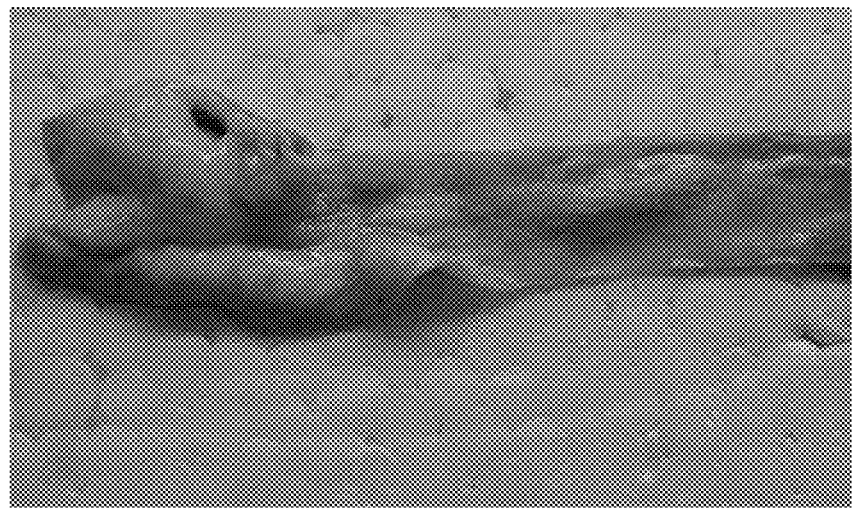

FIG. 81 is a photograph showing the buildup of plaque to a plaque area of 58.4% in the aorta of a lab animal with AFOD RAAS 1.

Figure 82:
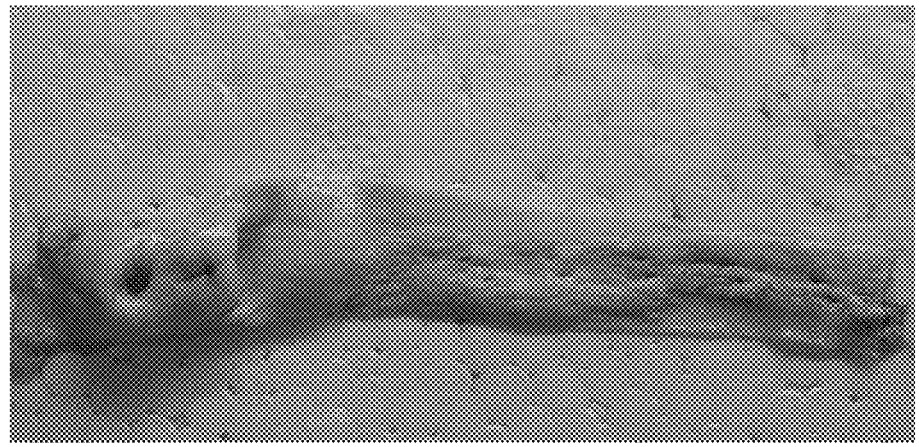

FIG. 82 is a photograph showing the buildup of plaque to a plaque area of 82.17% in the aorta of a lab animal with AFOD RAAS 1.

Figure 83:
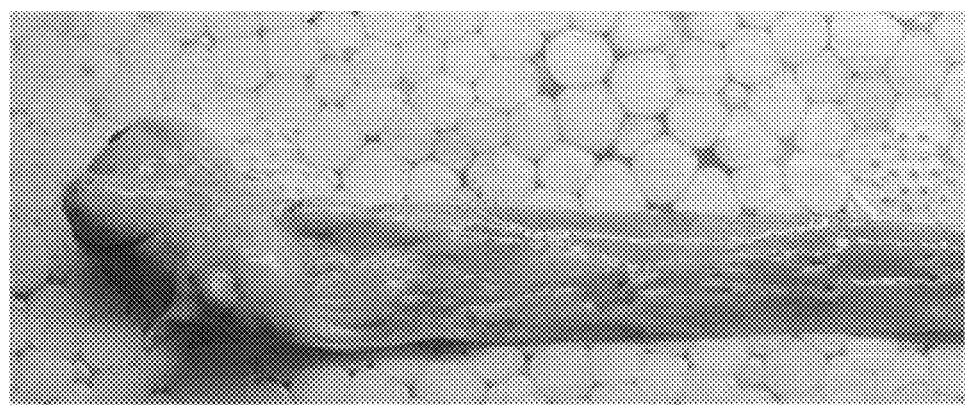

FIG. 83 is a photograph showing the buildup of plaque to a plaque area of 47.27% in the aorta of a lab animal with AFOD RAAS 1 for 11 weeks.

Figure 84:
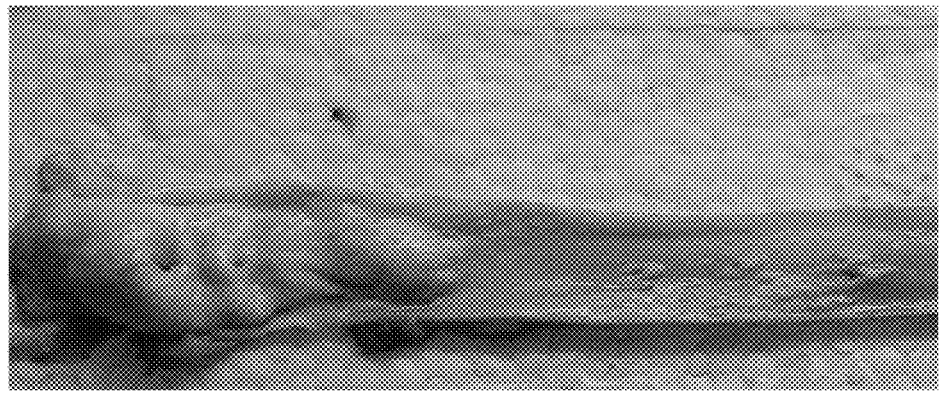

FIG. 84 is a photograph showing the buildup of plaque to a plaque area of 40.32% in the aorta of a lab animal with AFOD RAAS 1 for 11 weeks.

Figure 85:
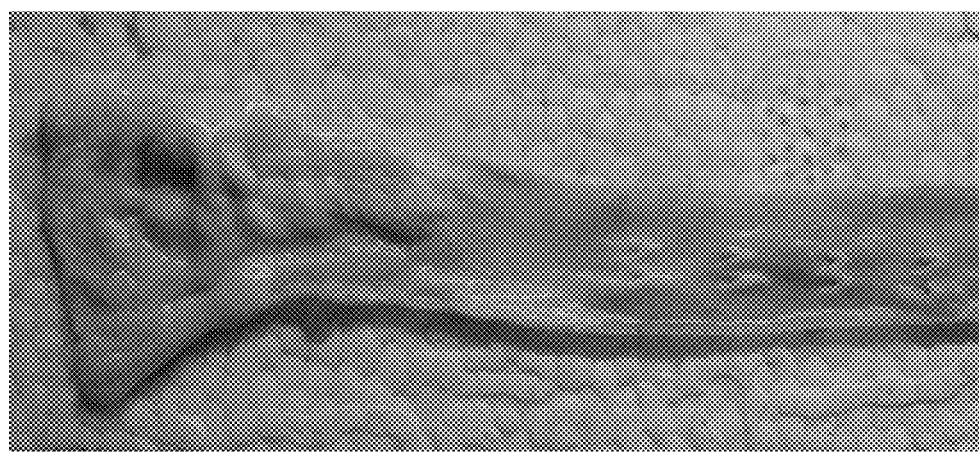

FIG. 85 is a photograph showing the buildup of plaque to a plaque area of 51.13% in the aorta of a lab animal with AFOD RAAS 1 for 11 weeks.

The $3^{rd}$ generation of APO purification.

Figure 1:
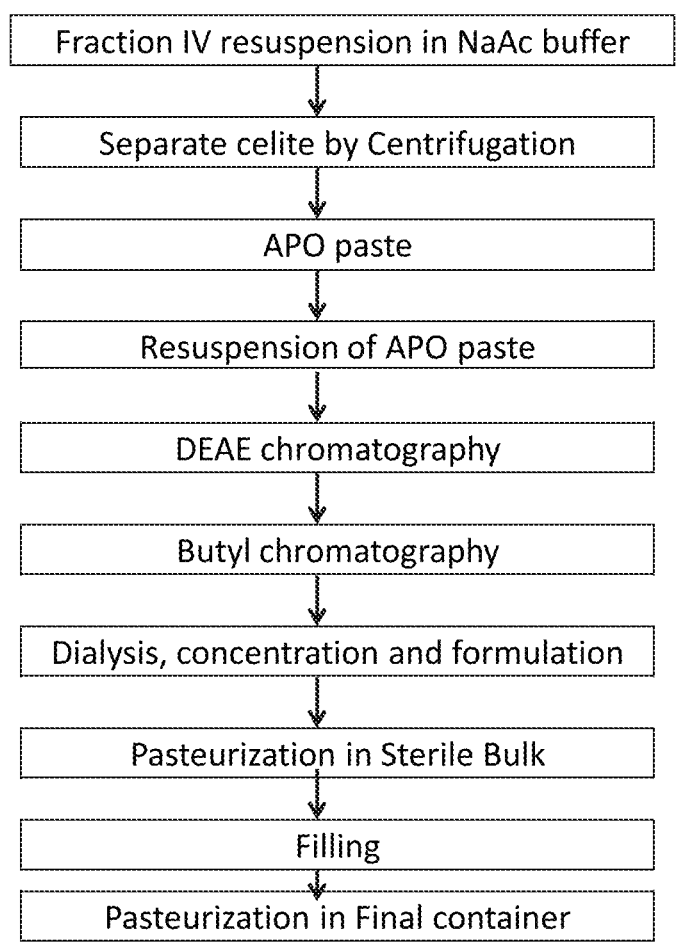
FIG. 1 is a flowchart of a process of purifying APO from plasma fraction IV according to the present invention.

The main difference is that urea is no longer required but need 2 steps of chromatography, as is shown in FIG. 1.

1. A method to purify APO from plasma fraction IV,
   1) Fraction IV is resuspended in a buffer with pH 3.00-10.00, and the celite and other impurities were separated by press filter or centrifugation, the resulted supernatant was then collected,
   2) The APO in the supernatant was then precipitated by adding NaCl and then was spin to collect the paste,
   3) The resulted APO was then resuspended and filtered,
   4) The resulted suspension was then underwent DEAE ion exchanging chromatography and butyl chromatography,
2. the fraction IV was resuspended in NaAc buffer with pH 3.00-10.00
3. the APO was precipitated by NaCl, pH 3.0-10.0, cool down to −1 to 1 C
4. the paste of APO can be resuspended in WFI or NaCl solution with pH 3.00-10.00 and 0-10 C
5. The resulted suspension is filtered with 0.45 um filter.
6. The chromatography in step 4 is Canion (DEAE) and butyl
7. The purification of APO by chromatography compromising,
   Canion chromatography, adjust pH of filtered APO suspension to 3.0-10.0 and ionic strength to 15-25 mM, load on DEAE chromatography, low salt wash the DEAE chromatography, and then high salt elute the DEAE chromatography, collect the resulted APO elute,
   Butyl chromatography, the resulted APO elute from DEAE chromatography is adjusted to pH 3.0-10.0 and low salt wash for impurities, WFI or alkaline buffer wash to collect APO enriched elute
8. The low salt buffer is a buffer containing Tris with pH 3.00-10.0, the high salt buffer is a buffer containing NaCl, the low salt elute buffer is a buffer containing Tris, the alkaline buffer is a buffer containing NaOH with pH 3.0-10.0
9. The resulted high purity of APO is then dialyzed and concentrated with virus inactivation, adding stabilizer and lyophilized.

Process Nr 4.

Figure 2:
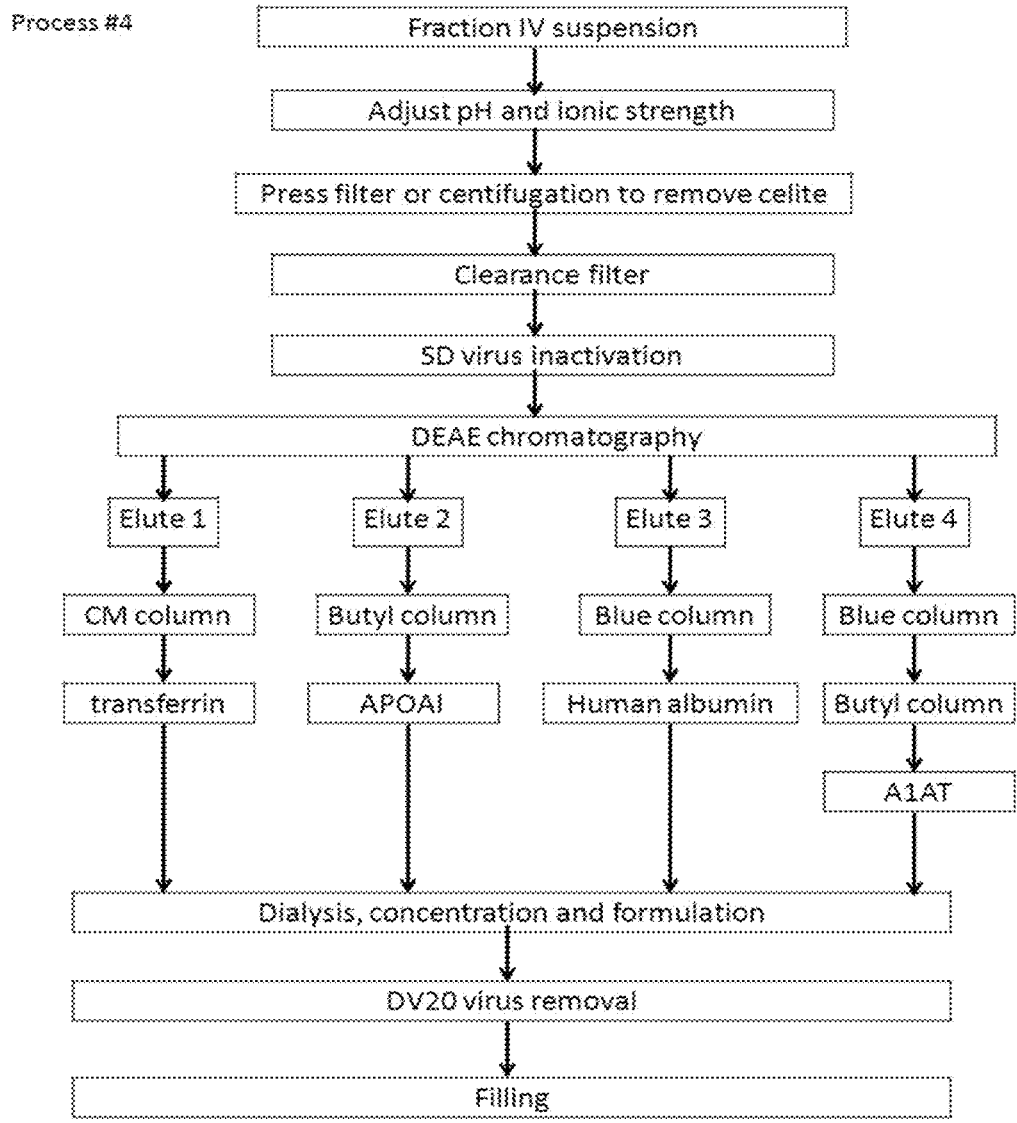
FIG. 2 is a flowchart of another process of purifying APO from plasma fraction IV according to the present invention.

A process that is separated the Fraction IV into 4 Proteins, as can be appreciated from FIG. 2:
1. Transferrin
2. Human Albumin
3. APO
4. Alpha 1 Antitrypsin (A1AT)
5. Transferrin+Human Albumin+APO+Immunoglobulin
6. Human Albumin+APO+Alpha 1 AntiStrepsin (A1AT)+Immunoglobulin
7. Human Albumin+APO+Immunoglobulin
8. Human Albumin+APO+Immunoglobulin+Transferrin+Antitrypsin Or all products from Nr 5 to Nr 8 can be processed separately and put together at the Non Sterile Final Bulk-Sterile Filtration-Filling-Final Products.

1. Re suspension of fraction IV and pretreatment
   1) Fraction IV is resuspended in a buffer with pH 3.00-10.00,
   2) The celite and other impurities were separated by press filter of centrifugation; the resulted suspension was then collected,
   3) The suspension was then treated with SD virus inactivation,
   4) The resulted suspension was then subject to a canion chromatography like DEAE,
   5) Proteins were eluted in different fractions,
   6) The different eluted fractions were then further purified,
2. The fraction IV was dissolved in low temperature buffer to achieve a in homogenous suspension,
3. The celite in resulted suspension can be removed by press filter or centrifugation,
4. the suspension was then cleared by depth filter
5. the resulted suspension was then treated with Tween-80 and TNBP for virus inactivation at 25 C for 6 hours,
6. The resulted suspension was adjusted pH and ionic strength and then subjected to a canion chromatography like DEAE. The targeted proteins were then binding to the canion chromatography resin, which are transferrin, human albumin, APO and A1AT. The $1^{st}$ elution was salt solution to elude the transferrin. The $2^{nd}$ elution was then eluded by a high concentration salt solution, which was APO. The $3^{rd}$ eluted fraction was human albumin by a low pH solution. Finally the $4^{th}$ elution was A1AT which was eluted by a high concentration salt solution.
7. The resulted various elution was then subjected to different chromatography for further purification to achieve a high purity. The $1^{st}$ elution fraction was subjected to a CM chromatography. The $2^{nd}$ elution fraction was subjected to a butyl chromatography. The $3^{rd}$ elution fraction was subjected to a blue chromatography. The $4^{th}$ elution fraction was subjected to a blue chromatography and a subsequent butyl chromatography.
8. The resulted protein fractions were then dialyzed and concentrated. The pH was adjusted and stabilizer was then added.
9. The resulted protein solutions were subjected to DV20 filtration for virus removal except human albumin.
10. The human albumin could be virus inactivated by Double pasteurization.
11. The resulted transferrin, APO, human albumin and A1AT can be filled.

AFCCRAAS 1: These processes of protein containing Healthy Good cells in Process 1 and Process 3 below are specially designed for Hemophilia A, B and WvB who have Been infected by HBV, HCV and specially HIV during the early of 1980 when effective process of inactivation of Enveloped viruses has not been introduced.

1. Process to separate Factor II, VII, IX, and X Transferrin, Human Albumin, APO and A1AT (ProthoRAAS®) from fraction III which also contain at least 20 additional proteins.
2. Process to separate Factor II, VII, IX, and X (ProthoRAAS®)+Human Albumin (AlbuRAAS®)+Immunoglobulin (GammaRAAS)
3. Process to separate Factor II, VII, IX and X from Cryopaste
4. Process to separate Factor II, VII, IX and X from Cryopaste+ATA1 APO+ Human Albumin (AlbuRAAS®) and Immunoglobulin (GammaRAAS)
5. Process to separate Thrombin (ThrombiRAAS®) from Fraction III
6. Process to combine all protein from Fraction III.

Figure 3:
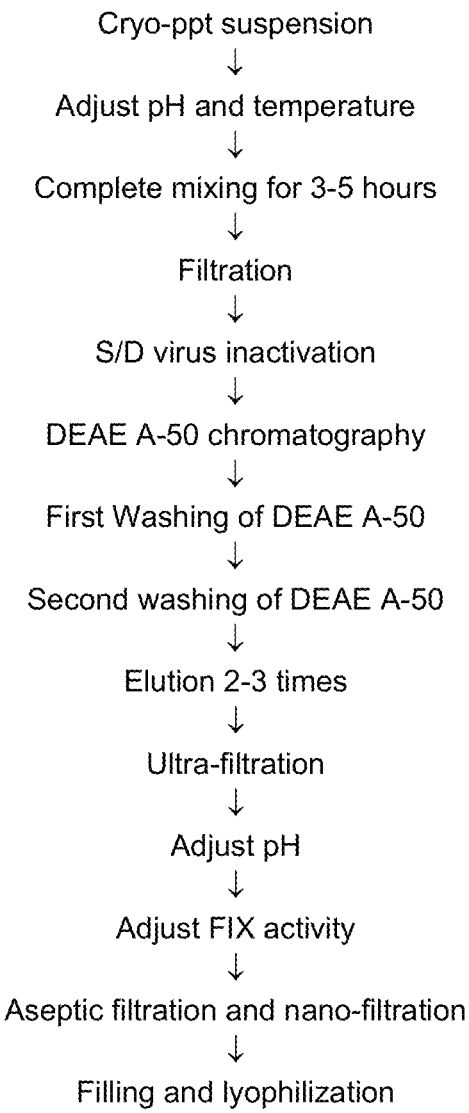
FIG. 3 is a flowchart of an AFCC process of purifying prothrombin complex from cryopaste in accordance with the present invention.
Figure 4:
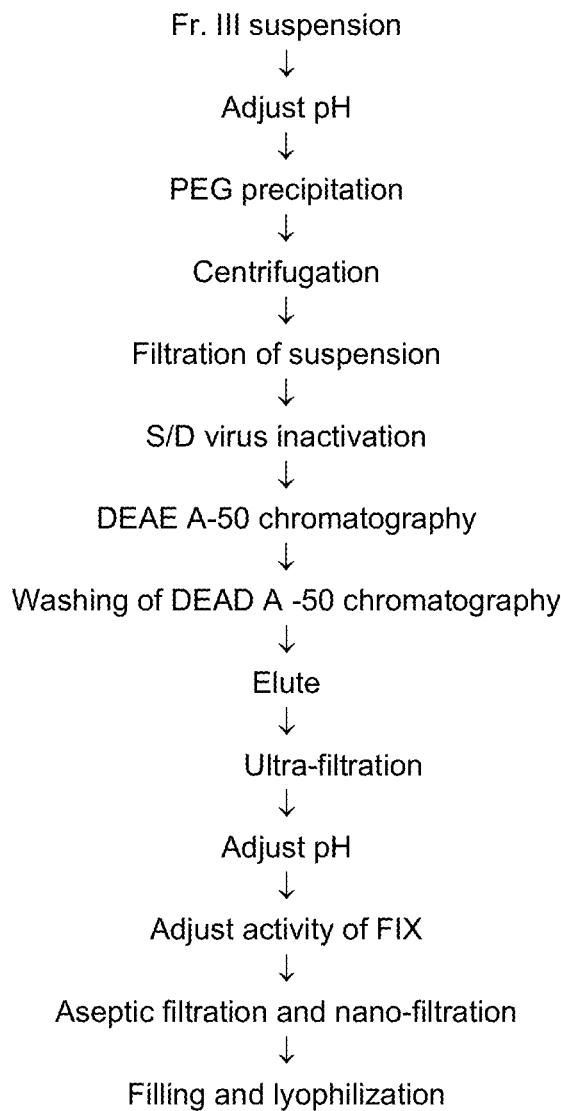
FIG. 4 is a flowchart of an AFCC process of purifying prothrombin complex from fraction III in accordance with the present invention.
Figure 5:
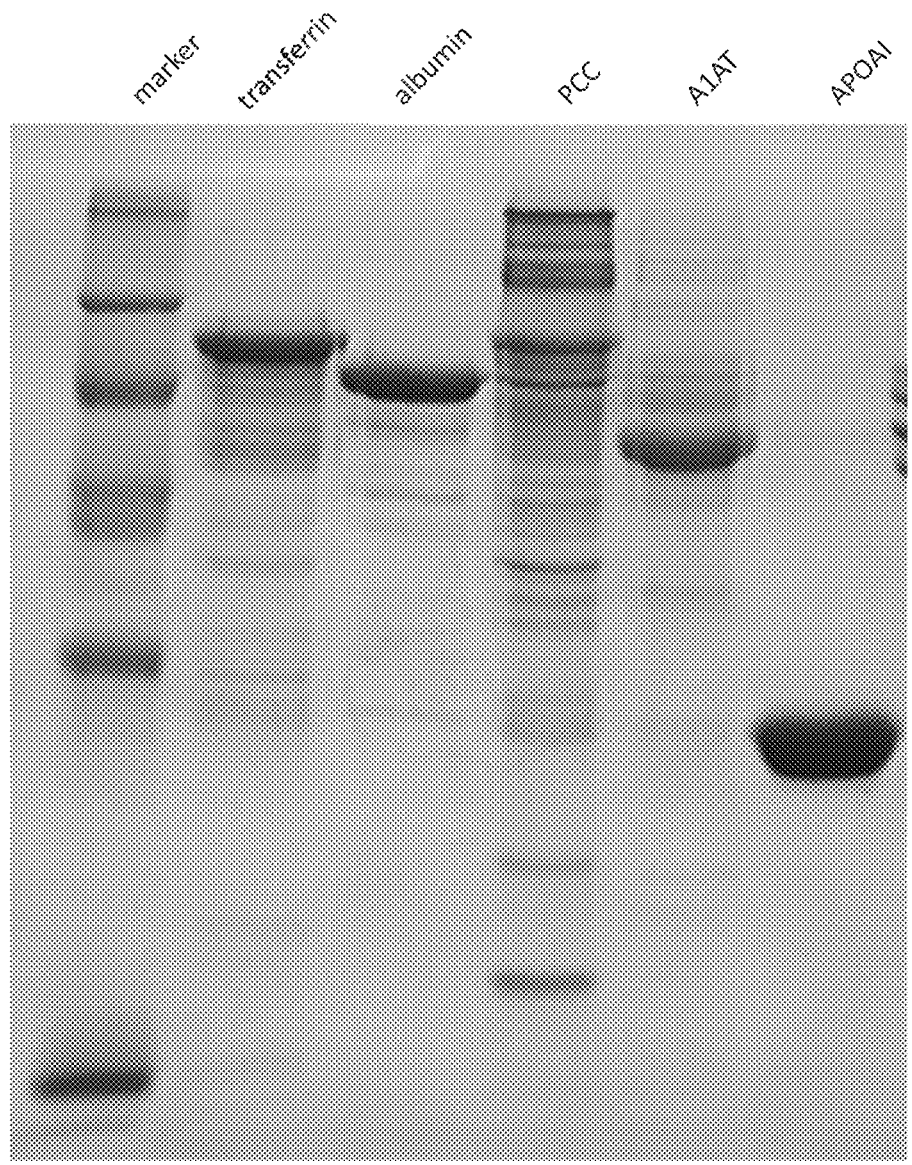
FIG. 5 shows the electrophoresis result of cation chromatography of proteins including transferrin, human albumin, APOA1, PCC and A1AT.
Figure 6:
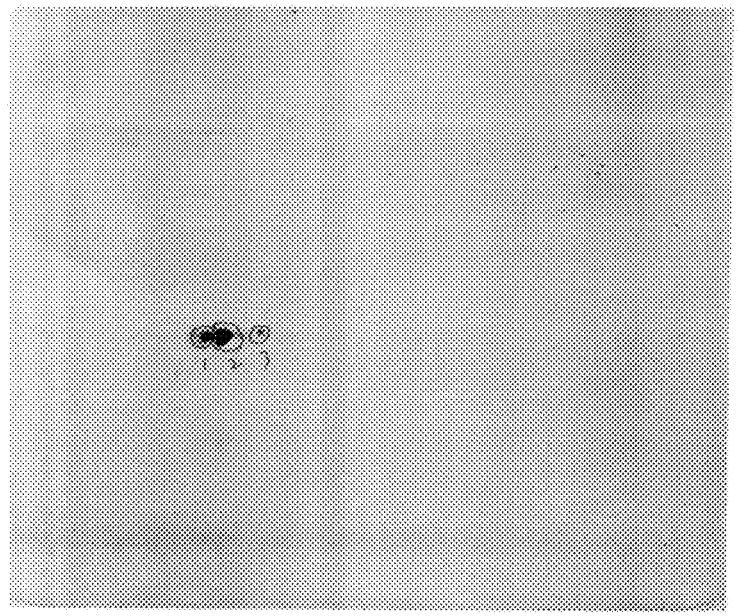
FIG. 6 shows the 2D electrophoresis results of AFOD.

Description
1. As can be seen in FIG. 3, this process describes a process to purify prothrombin complex from cryoprecipitaiton, which comprises,
   1) Re-constitute cryopaste in buffer containing 3,000 U/kg heparin,
   2) Adjust pH and temperature
   3) Complete mix at room temperature for 3 to 5 hours
   4) Filter the resulted suspension with 10CP+90SP filter
   5) Solvent detergent virus inactivation of resulted suspension
   6) weak anion exchange chromatography of SD virus inactivated suspension
   7) Twice washing of weak anion exchange chromatography
   8) Elute weak anion exchange chromatography 2 to 3 times
   9) Collect the result elution and ultra-filter with 10K membrane
   10) Adjust pH of resulted elution
   11) Adjust the activity of human FIX in the resulted elution
   12) Aseptic filtration and nano filtration for virus removal
   13) Filling and lyophilization Description
2. As can be seen in FIG. 4, this process describes a process to purify prothrombin complex from fraction III, which comprises,
   14) Re-constitute cryopaste in buffer,
   15) Adjust pH and temperature
   16) PEG precipitation of resulted fraction III suspension
   17) Centrifugation and collect the supernant
   18) Filter the resulted suspension with 10CP+90SP filter
   19) Solvent detergent virus inactivation of resulted suspension
   20) weak anion exchange chromatography of SD virus inactivated suspension
   21) Twice washing of weak anion exchange chromatography
   22) Elute weak anion exchange chromatography 2 to 3 times
   23) Collect the result elution and ultra-filter with 10K membrane
   24) Adjust pH of resulted elution
   25) Adjust the activity of human FIX in the resulted elution
   26) Aseptic filtration and nano filtration for virus removal
   27) Filling and lyophilization AFOD is High Density Lipoprotein (ApoA1):
Reference is made to FIGS. 5 and 6. The three dots in our analysis of AFOD are all ApoA1. The difference showed in 2D electropherosis of FIG. 6 might be due to different isoform of ApoA1 or Apo in the Apo family.

1. HDL (ApoA1): AFOD RAAS 1 (Trade mark) contains purified ApoA1 in the process described Nr 1 (China Patent granted 200610147503.7) Nr1&N2 (US 2009/0286960 A1) Nr 3,4 (U.S. 61/457,380) with a purity of 96% and the products must be free of all HIV1,2, HCV, HBV viruses and contain very good level of High Density Lipoprotein (HDL) which is GOOD CHOLESTEROL, No value or very low value of VLDL (Very low density Lipoprotein) and no value or very low value of LDL (Low Density Lipoprotein), both of which are BAD CHOLESTEROL. Potential applications: Cholesterol, Angina, hyperlipidemia, Clean plaque, fat on liver, Life span, Control of Obesity, Hypertension, Prevention of Heart attack, Prevention of Stroke, Prevention of Paralysis due to the stroke and other potential indications as described.
2. AFODRAAS 2 (Human Albumin+ApoA1) In addition to current clinical applications for AlbuRAAS® Potential applications for trauma management/Arthritis/Schizophrenia/Depression/Certain types of cancers Lung, Pancreas, Kidney, Liver, Prostate, Breast and other potential indications
3. AFODRAAS 3 (Intravenous Immuno Globulin+ApoA1) for current clinical applications for GammaRAAS® and for potential applications for all blood (liquid) cancers as described in abstract)
4. AFODRAAS 4 (Factor VIII+ApoA1) for the current clinical applications of HemoRAAS® and for potential applications for Hepatitis B, Hepatitis C and HIV 1,2, Bleeding complications/Bone Surgery in Patients with Hemophilia A (orthopedics, liver, pancreas, cancer of the gastrointestinal tube and eventually build up Coagulation so patients will no longer need to use Factor VIII for hemophilia A and all solid tumor and blood cancers/
5. AFODRAAS5 (Prothombin Complex Concentrate+ApoA1) for the current clinical applications of ProthoRAAS® and for potential applications for Hepatitis B, Cirrhosis, and other hepatic trouble like biliary tree obstruction Hepatitis C, HIV 1,2 Bleeding/Bone Complications and surgeries for Hemophilia B and Hemophilia A with inhibitor and eventually build up coagulation so patients will no longer need to use Factor IX or PCC and all solid tumor and blood cancers
6. AFODRAAS6 (Thrombin+ApoA1) for the current clinical applications of ThrombiRAAS® and for potential applications for Gastric and duodenal ulcer, ulcers and other problems of colon (large intestine)
7. AFODRAAS7 (Fibrinogen+ApoA1) for the current clinical applications of FibroRAAS® and for potential applications for Trauma Management and other potential indications as described
8. AFODRAAS8 (Fibrin Sealant+ApoA1) for the current clinical applications of FibrinGluRAAS® and potential TOPICAL APPLICATIONS for ALL SOLID TUMOR CANCERS which can be operated and cancers have not been spread to other parts of body.
9. AFODRAAS 9 (ApoA1+Human Albumin (AlbuRAAS)+Alpha 1 Antitrypsin (A1AT)+Transferrin for all potential indications as described
10. AFODRAAS 10 (ApoA1+Human Albumin+Alpha 1 Antitrypsin (A1AT) for all potential indications as described.
11. AFODRAAS 11 (ApoA1+Human Albumin+Transferrin) for all potential indications as described.
12. AFODRAAS 12 (ApoA1+Alpha 1 Antitrypsin ((A1AT)) for all potential indications as described.

13. AFODRAAS 13 (ApoA1+Transferrin for all potential indications as described.
14. AFODRAAS 14 (Alpha 1 Antitrypsin ((A1AT))+Transferrin) for all potential indications as described.
15. AFODRAAS 15 (Transferrin) for All potential indications as described.

Figure 7:
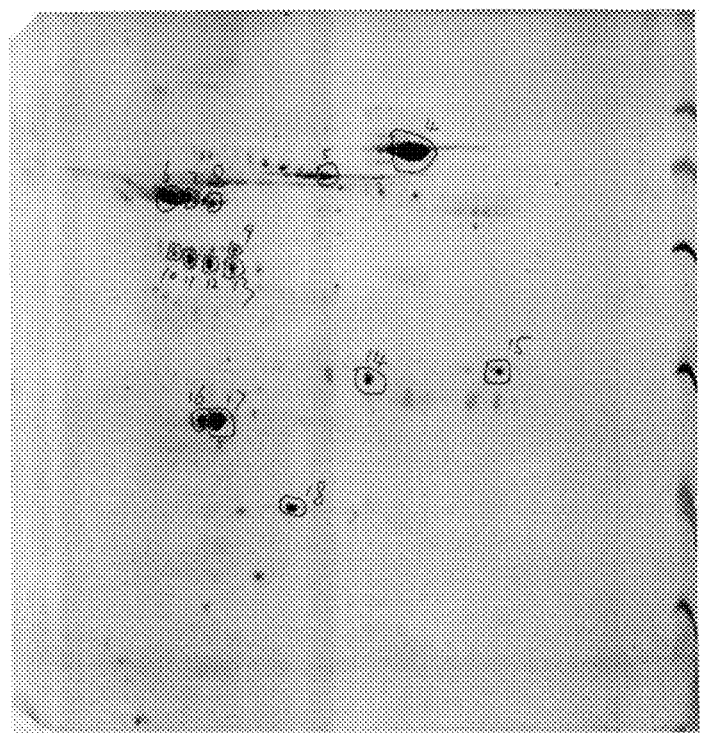
FIG. 7 shows an analysis of a Fraction IV suspension by 2D electrophoresis.

In our analysis of Fraction IV suspension by 2 D electropherosis, as shown in FIG. 7, the following proteins were found in the Fraction IV suspension:

The main proteins found in Fraction IV suspension are: Transferrin, Human Albumin, Alpha 1 AntiStrepsin, and ApoA1

The rest of the proteins are: SEMENOGELIN-1, HAPTOGLOBIN, VIMENTIN, NESPRIN-2, INTERFERON ALPHA 1/13, HP PROTEIN, VITAMIN D-BINDING, ALPHA-FETOPROTEIN, CASK, AMYLOID PRECURSOR, NEUREXINS AND SYNDECANS.

SEMENOGELIN-1: The protein encoded by this gene is the predominant protein in semen HAPTOGLOBIN: In Blood Plasma, Haptoglobin binds free hemoglobin (Hb) released from erythrocytes with high affinity and thereby inhibits its oxidative activity.

VIMENTIN is a member of the intermediate filament family of proteins that is especially found in connective tissue. They, along with microtubules and actin microfilaments, make up the cytoskeleton THE NESPRINS are a family of proteins that are found primarily in the outer nuclear membrane. Nesprin-1 and Nesprin-2 bind to actin filaments.

VITAMIN-D BINDING PROTEIN belongs to the albumin gene family, together with Human serum albumin and alpha-fetoprotein. It is a multifunctional protein found in plasma, ascetic fluid, cerebrospinal fluid and on the surface of many cell types. It binds to Vitamin D and its plasma metabolites and transport them to target tissues.

CASK PROTEIN Peripheral plasma membrane protein CASK is a protein that in humans is encoded by the CASK gene. This protein is a multi domain scaffolding protein with a role in synaptic transmembrane protein anchoring and ion channel trafficking. It interacts with the transcription factor TBR1 and binds to several cell-surface proteins including amyloid precursor protein, neurexins, and syndecans.

Figure 8:
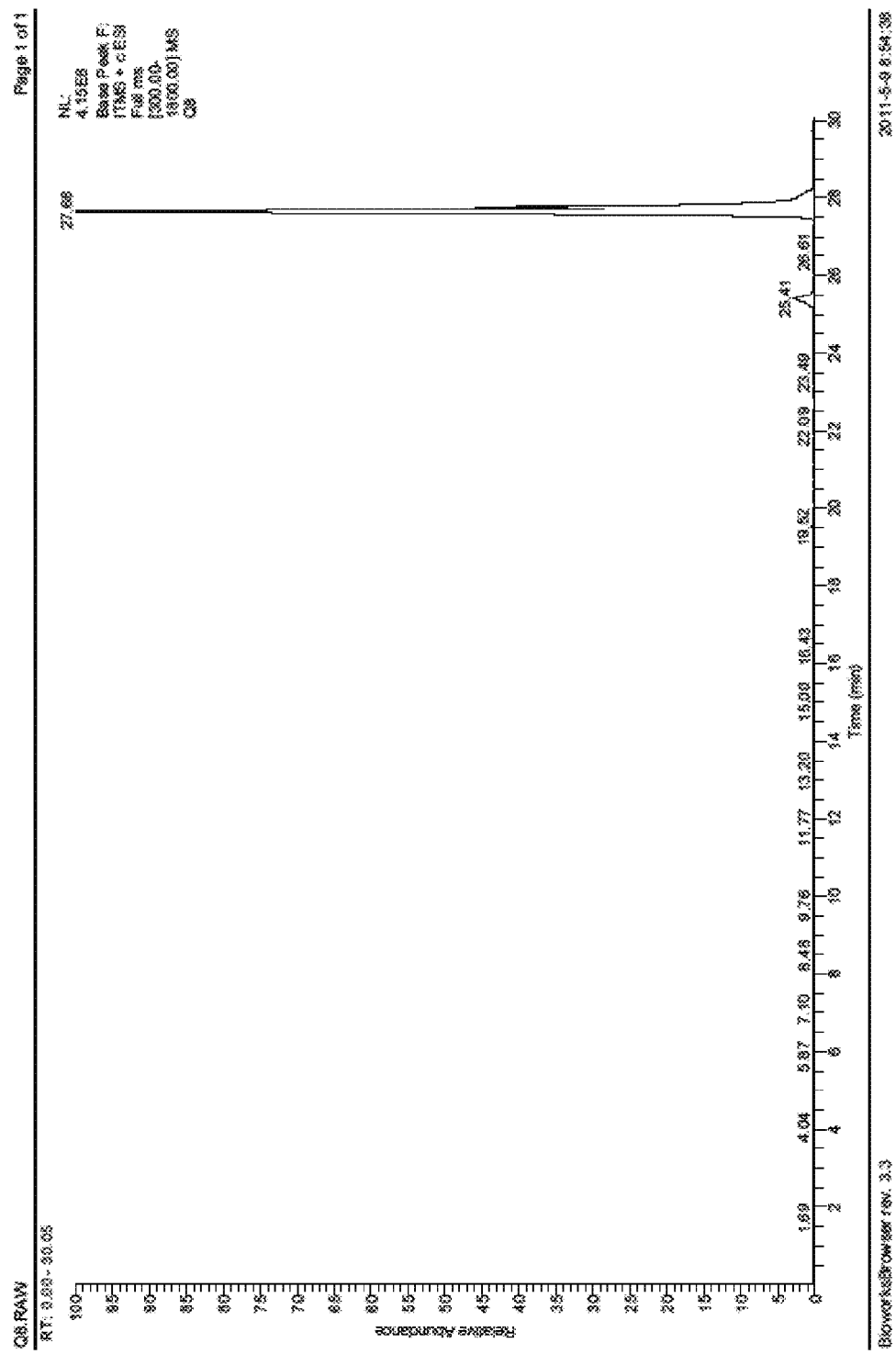
FIG. 8 is a graph showing the relative abundance over time of Q8 Gene Symbol=GC Vitamin D binding protein Precursor—Cask isoform 3 of Peripheral plasma membrane protein CASk—VIM Vimentin.
Figure 9:
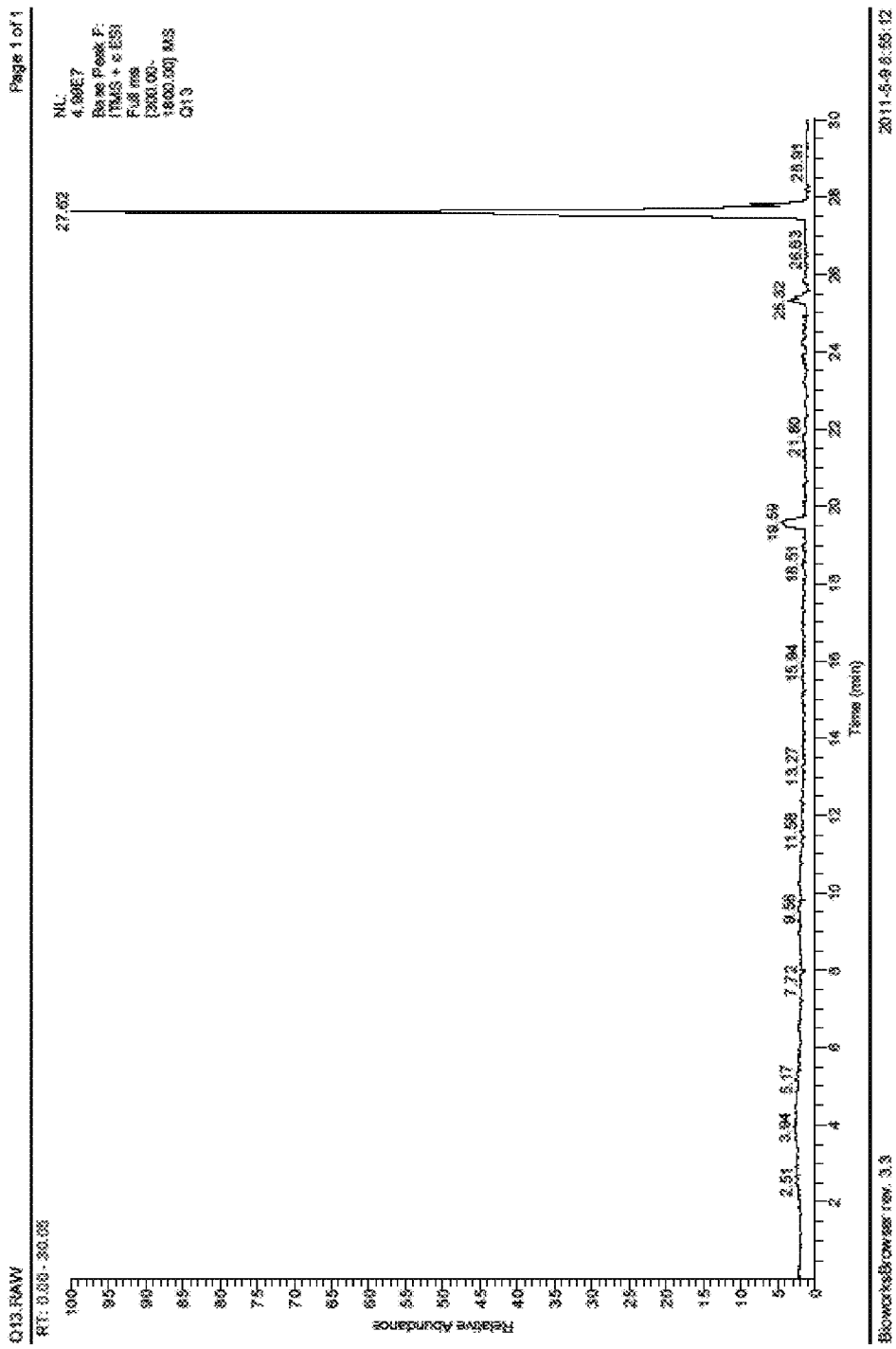
FIG. 9 is a graph showing the relative abundance over time of Q13 Gene Symbol=CASK Isoform 3 of Peripheral plasma membrane protein CASK—HP HP protein.
Figure 10:
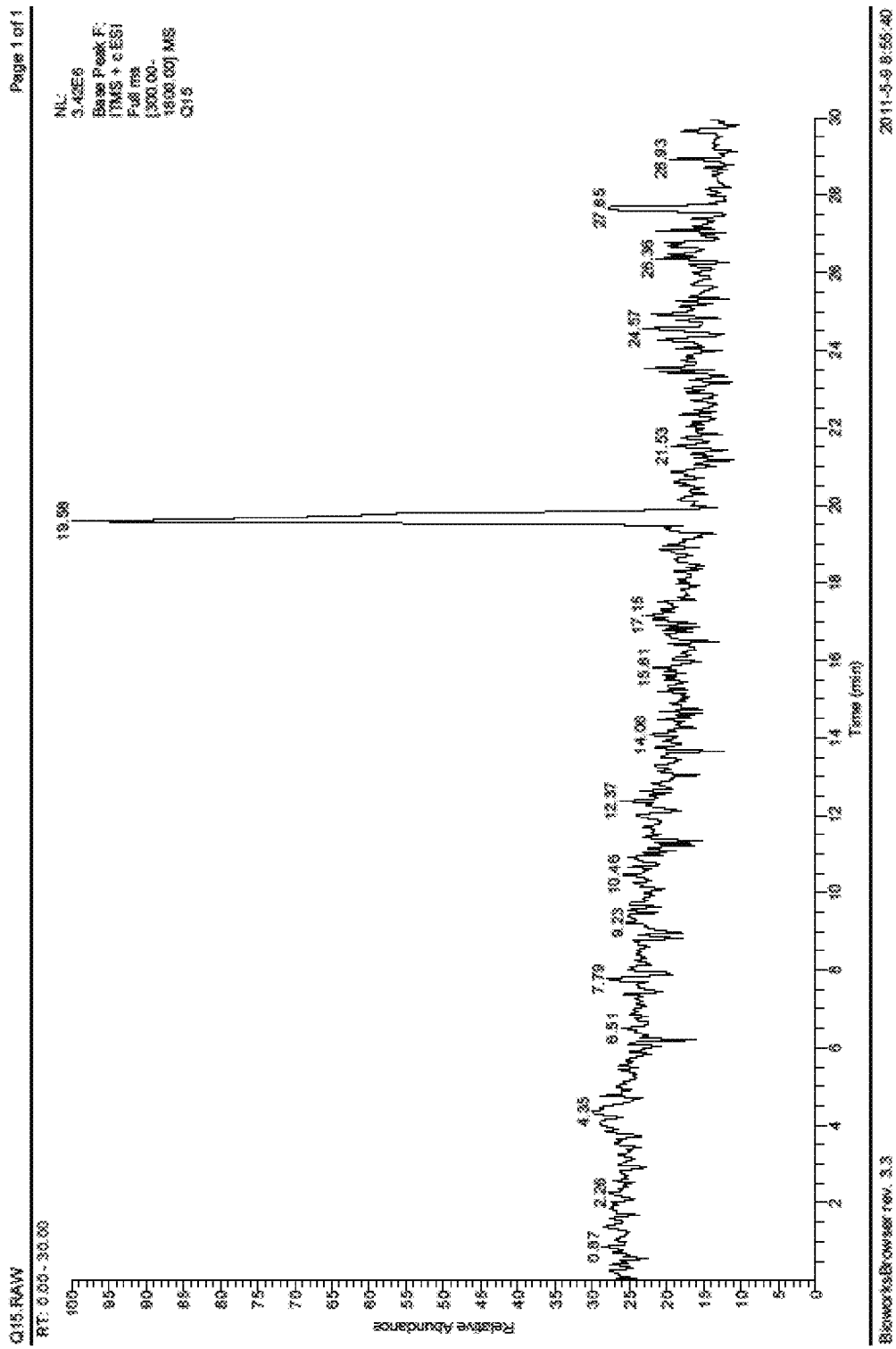
FIG. 10 is a graph showing the relative abundance over time of Q15 Gene Symbol—CASK Isoform 3 of Peripheral plasma membrane protein CASK—IFNA13 IFNA1 Interferon alpha-1/13.

FIG. 8 relates to Q8 Gene Symbol=GC Vitamin D binding protein Precursor—Cask isoform 3 of Peripheral plasma membrane protein CASk—VIM Vimentin FIG. 9 relates to Q13 Gene Symbol=CASK Isoform 3 of Peripheral plasma membrane protein CASK—HP HP protein FIG. 10 relates to Q15 Gene Symbol—CASK Isoform 3 of Peripheral plasma membrane protein CASK—IFNA13; IFNA1 Interferon alpha-1/13

AFCC is Prothombin Complex Concentrate (ProthoRAAS®) a combination of blood clotting factors II, VII, IX and X or Factor IX.

Factor IX is one of several factors made in the liver with similar structural properties.

Together with factors II (Prothombin), VII (proconvertin) and X (Stuart-Prower factor), factor IX (antihaemophilic factor B) comprises the so called prothombin complex group of factors, also known as PPSB factors.

Owing to their similarity, the proteins in this group are usually isolated together in fraction III in the Cohn alcohol fractionation process.

They are then purified to give preparations containing all four factors, Prothombin complex concentrates (PCC).

ProthoRAAS are indicated currently for:
Haemophilia B—Prophylaxis, Bleeding, Surgery
Haemophilia A—Inhibitor treatment
Liver disease—Acute and chronic—active hepatitis, cirrhosis
Vitamin K deficiency—Oral anticoagulants, Obstructive jaundice, Malabsorption, changes in intestinal flora (antibiotics, Morbus Crohn, ulcerative colitis)
DIC (Disseminated Intravascular Coagulation)—Infection, Liver disease, obstetrical emergencies, surgical complications.

16. AFCC RAAS1 (Trade mark) (ProthoRAAS®+ApoA1+AT-III) for the current indications as above together with all potential indications as described.
17. AFCC RAAS 2 (Trade mark) (Prothombin Complex Concentrate (ProthoRAAS®)+ApoA1+Human Albumin (AlbuRAAS®)), for the current indications as above together with all potential indications as described.
18. AFCC RAAS 3 (Trade mark) (Prothombin Complex Concentrate (ProthoRAAS®)+ApoA1+Intravenous Immuno Globulin (GammaRAAS®)), for the current indications as above together with all potential indications as described.
19. AFCC RAAS 4 (Trade mark) (Prothombin Complex Concentrate (ProthoRAAS®)+ApoA1+Intravenous Immuno Globulin (GammaRAAS®), +Human Albumin (AlbuRAAS®)), for the current indications as above together with all potential indications as described.
20. AFCC RAAS 5 (Trade mark) (Prothombin Complex Concentrate (ProthoRAAS®)+ApoA1+Intravenous Immuno Globulin (GammaRAAS®), +Human Albumin (AlbuRAAS®) and Fibrinogen (FibroRAAS®)), for the current indications as above together with all potential indications as described.
21. AFCC RAAS 6 (Trade mark) (Prothombin Complex Concentrate (ProthoRAAS®)+ApoA1+Fibrinogen (FibroRAAS®)), for the current indications as above together with all potential indications as described.

Figure 11:
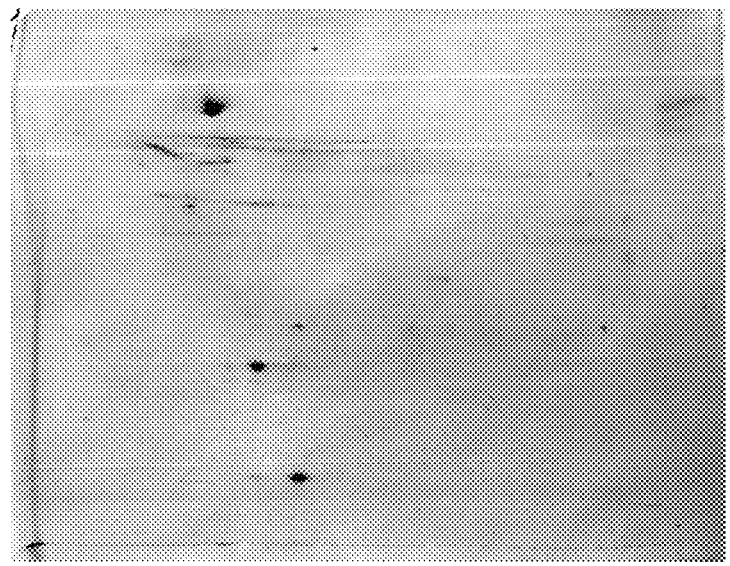
FIG. 11 shows the results of a 2D electrophoresis of prothrombin complex concentrate.

2D Electropherosis of PCC:
Results of 2D eletropherosis of PCC not only the above four factors proteins but also show a lot more proteins (Dots) that are being identified, as can be seen in FIG. 11.

Figure 12:
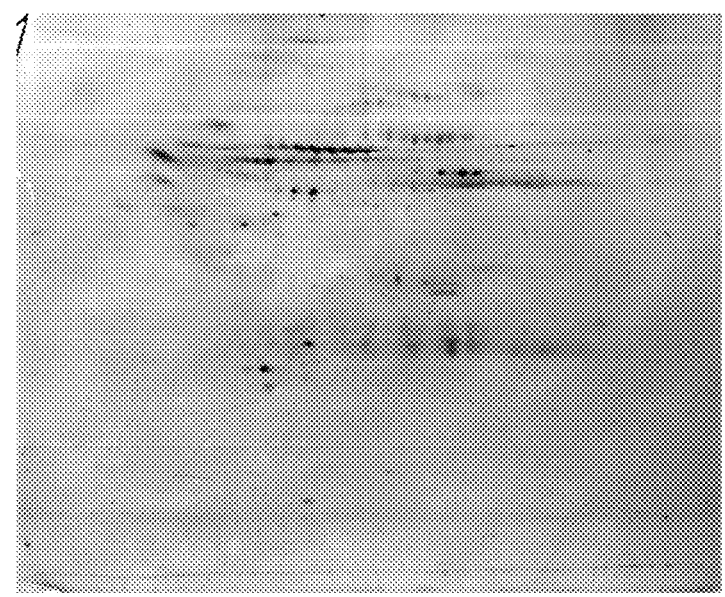
FIG. 12 shows the results of a 2D electrophoresis of Fraction III.

2D Electropherosis of Fr. III:
2D electropherosis of Fraction III like Fraction IV contains a lot more of proteins other than Thrombin, Prothombin Complex, as can be seen in FIG. 12. All these proteins are also being identified.

Figure 13:
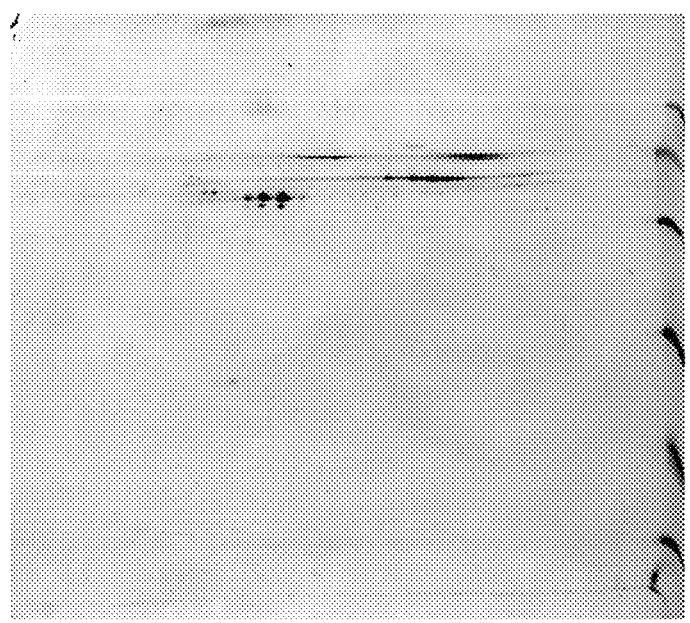
FIG. 13 shows the results of a 2D electrophoresis of cryopaste.

2D Electropherosis of Cryopaste:
2 D electropherosis of Cryopaste results also show some other proteins which are being identified Beside Fibrinogen and Factor VIII, as can be seen in FIG. 13.

In Vitro/Vivo Studies
$1^{st}$ Production of 10 Batches totaling 200 grams for use in vivo study of Rabbits at Fudan University, Shanghai, China.

Figure 14:
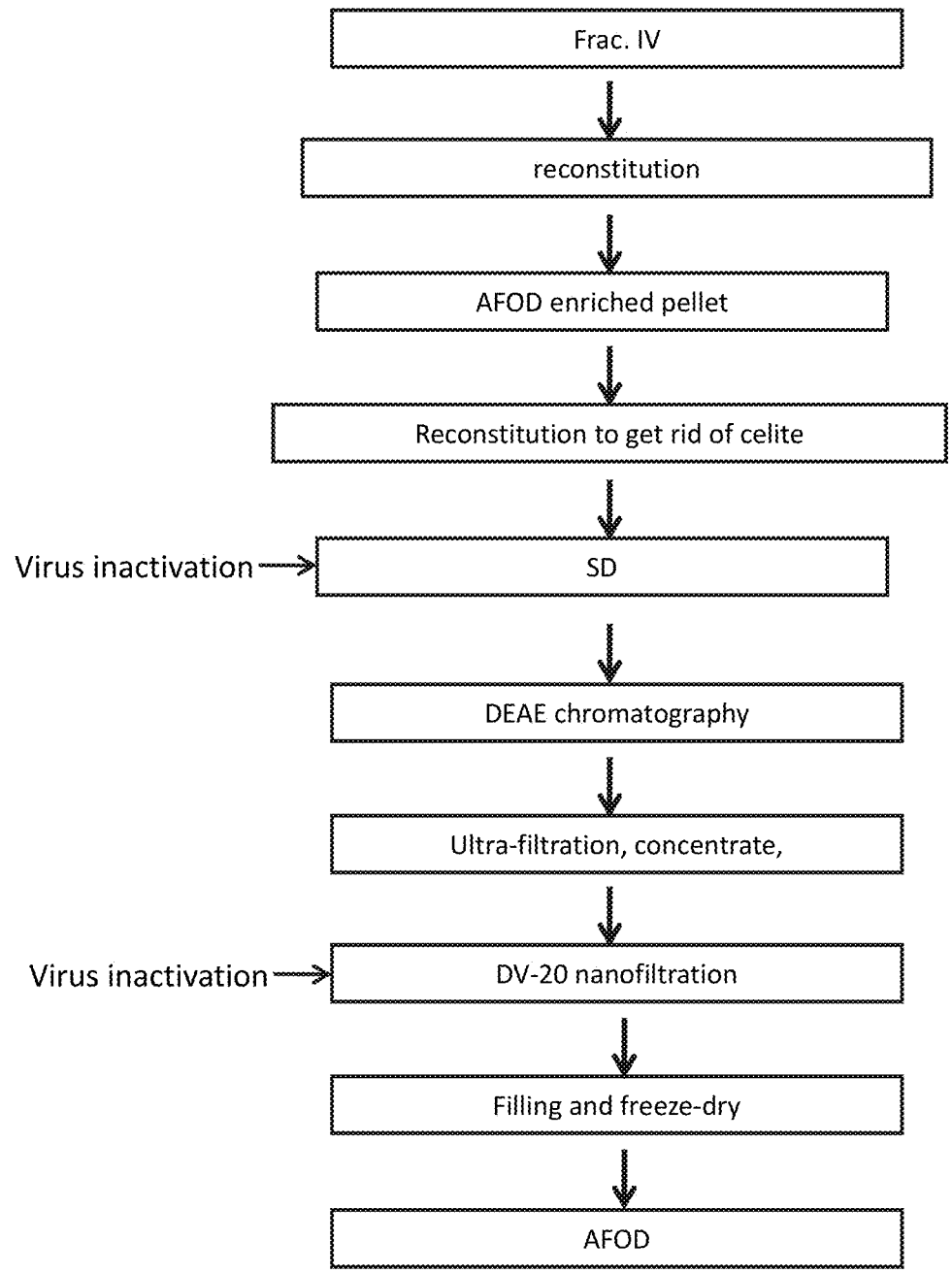
FIG. 14 is a flowchart of a process for purifying AFOD.
Figure 15:
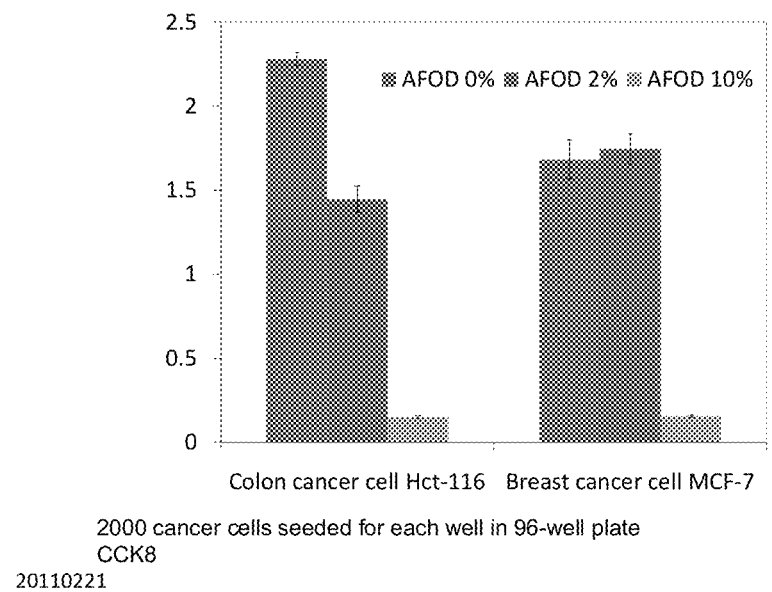
FIG. 15 is a graph showing cancer cell proliferation during a 3-day in vitro study of colon and breast cancer cell lines in the presence of varying concentrations of AFOD solution.
Figure 16:
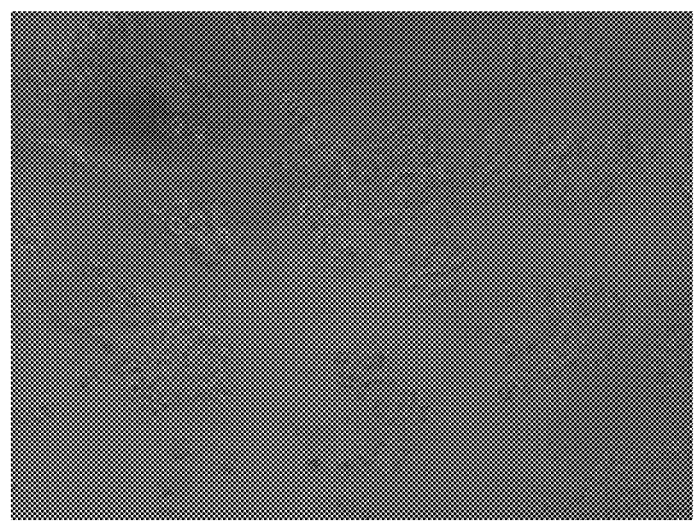
FIG. 16 is an image taken on Day 3 after treatment showing the proliferation of Colon cancer cells HCT 116 in 0% AFOD solution.
Figure 17:
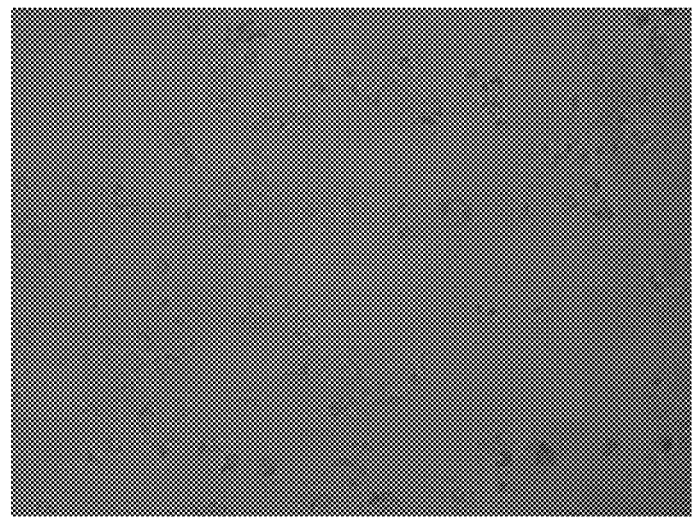
FIG. 17 is an image taken on Day 3 after treatment showing the proliferation of Colon cancer cells HCT 116 in 2% AFOD solution.
Figure 18:
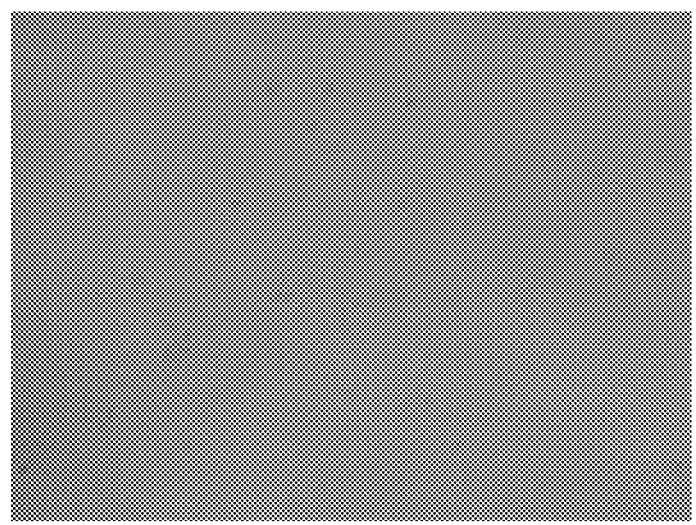
FIG. 18 is an image taken on Day 3 after treatment showing the proliferation of Colon cancer cells HCT 116 in 10% AFOD solution.
Figure 19:
FIG. 19 is an image taken on Day 3 after treatment showing the proliferation of Breast cancer cells MCF-7 in 0% AFOD solution.
Figure 20:
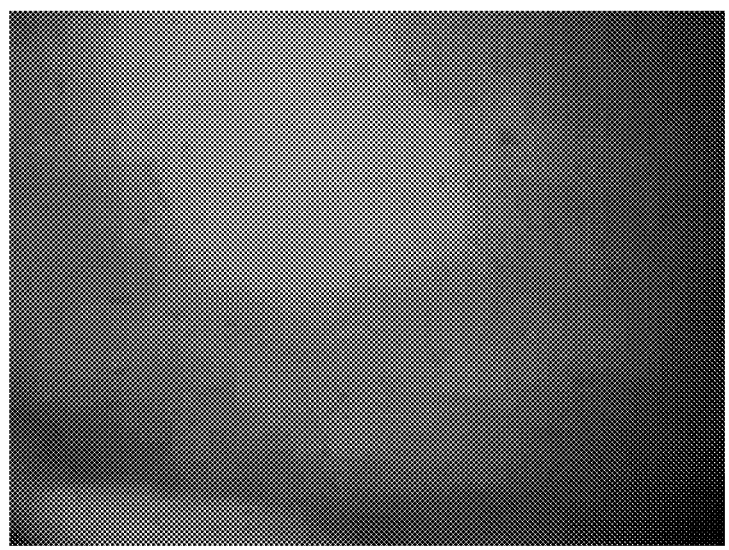
FIG. 20 is an image taken on Day 3 after treatment showing the proliferation of Breast cancer cells MCF-7 in 2% AFOD solution.
Figure 21:
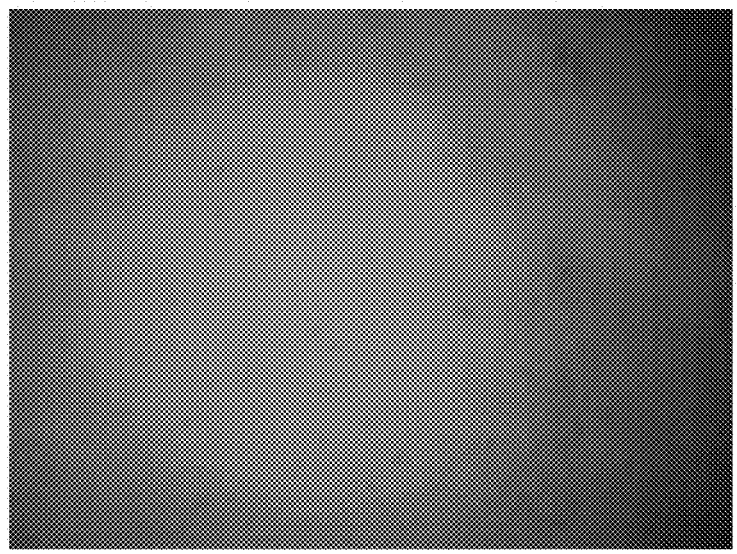
FIG. 21 is an image taken on Day 3 after treatment showing the proliferation of Breast cancer cells MCF-7 in 10% AFOD solution.
Figure 22:
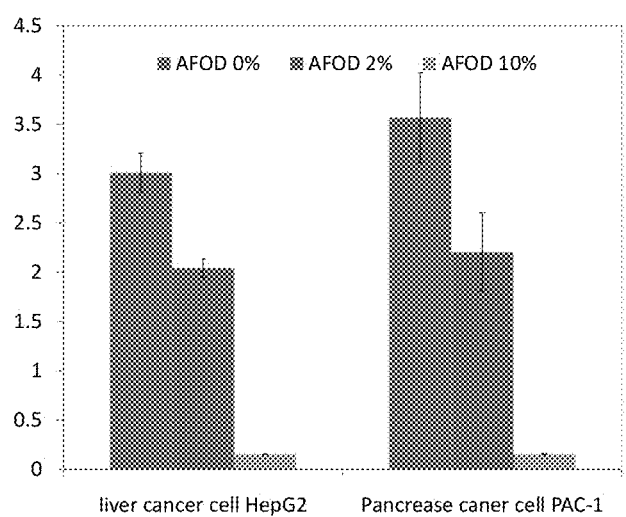
FIG. 22 is a graph showing cancer cell proliferation during a 3-day in vitro study of liver and pancreas cancer cell lines in the presence of varying concentrations of AFOD solution.
Figure 23:
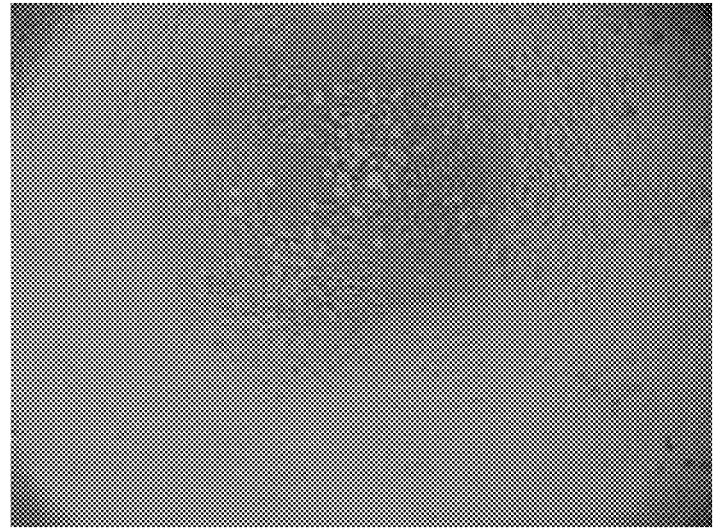
FIG. 23 is an image taken on Day 3 after treatment showing the proliferation of liver cancer cells HepG2 in 0% AFOD solution.
Figure 24:
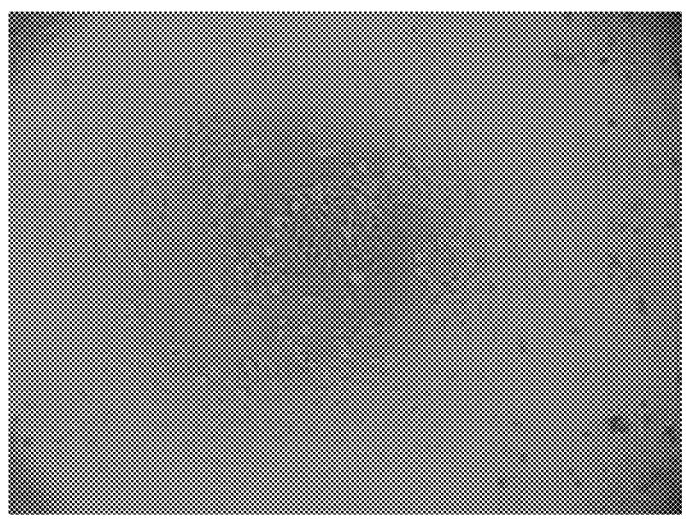
FIG. 24 is an image taken on Day 3 after treatment showing the proliferation of liver cancer cells HepG2 in 2% AFOD solution.
Figure 25:
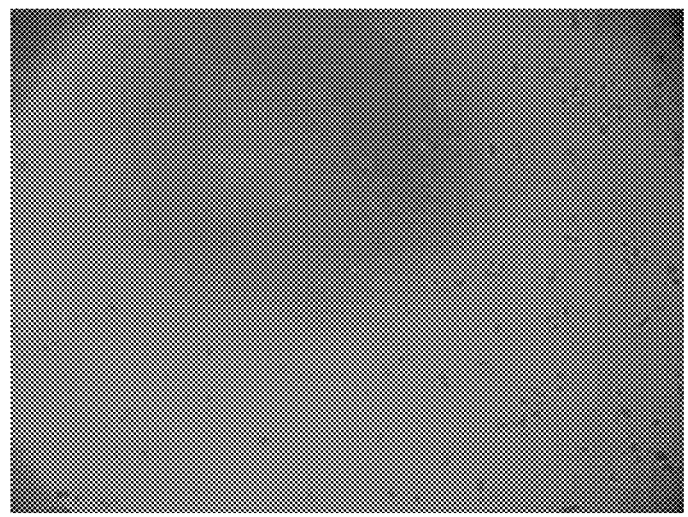
FIG. 25 is an image taken on Day 3 after treatment showing the proliferation of liver cancer cells HepG2 in 10% AFOD solution.
Figure 26:
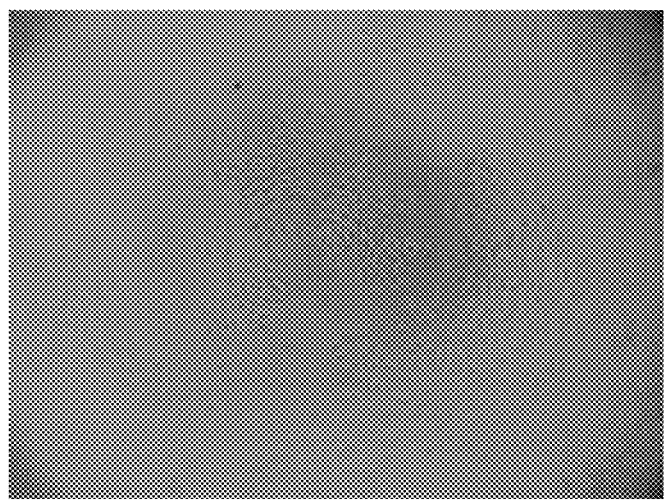
FIG. 26 is an image taken on Day 3 after treatment showing the proliferation of pancreas cancer cells PAC-1 in 0% AFOD solution.
Figure 27:
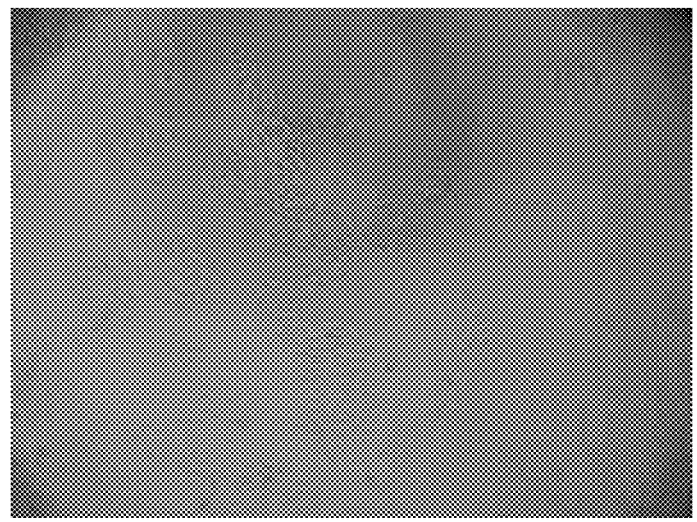
FIG. 27 is an image taken on Day 3 after treatment showing the proliferation of pancreas cancer cells PAC-1 in 2% AFOD solution.
Figure 28:
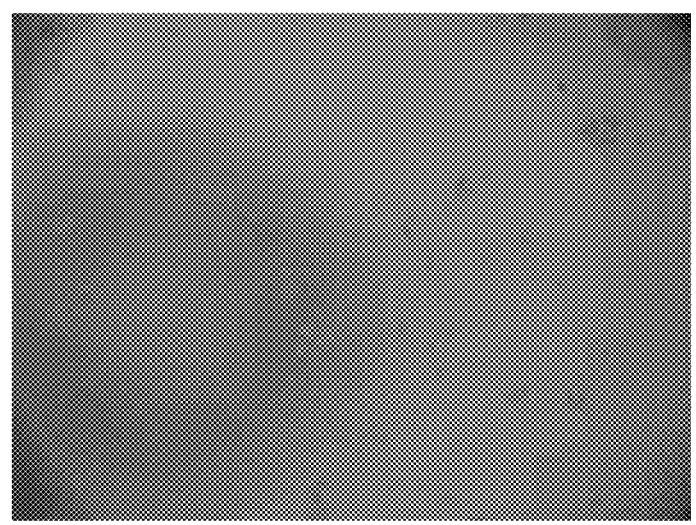
FIG. 28 is an image taken on Day 3 after treatment showing the proliferation of pancreas cancer cells PAC-1 in 10% AFOD solution.

The $1^{st}$ 200 g AFOD was purified in East China University of Science and Technology using Process No. 1, a flow chart for which is presented in FIG. 14. The pilot production capability of that lab is about 5 kg per time. The purification process was modified according to their equipment on site but the flow was same as we have done in this December The major differences are as following 1) The input of production was 5 kg of Fraction IV paste and yield was about 25 g AFOD each time. Dr. Li Chun Zhou produced 10 lots there to get 200 g AFOD;

2) The column used for AFOD purification was about 5 L DEAE chromatography;
3) The centrifugation for collecting AFOD enriched pellet was swing basket rotor centrifuge
4) Standing precipitation was used to get rid of celite;
5) For filling, manual filling was adopted;
6) No virus inactivation was used in the whole process.

The resulted AFOD was about 200 g for total 10 lots and all of AFOD were lyophilized.

The stabilizer used was mannitol and this product has been used to perform clinical studies on 52 rabbits in summer of 2008.

$2^{nd}$ Pilot Production of 3 Lots at Shanghai RAAS Blood Products Co Ltd 2000 vials of AFOD RAAS (about 200 g) have been used in the following in vitro studies:
1. Studies of 5 cancer cells line at RuiJin Hospital Shanghai China.
2. Studies of 3 cancer cells line at R/D Lab Shanghai RAAS.
3. Studies of Bacteria at Microbiology Lab, Shanghai RAAS
4. Studies of Viruses HIV1,2 at NAT Lab, Shanghai RAAS In the most recent pilot production, which was conducted in last December at our Plant, we totally conducted 3 lots of production. It was 25 kg Fraction IV for the $1^{st}$ lot, 50 kg for the rest of 2 lots. The total yield was about 2000 vials of AFOD (about 200 g). There were about 440 bottles of lyophilized, 660 vials of liquid with human albumin for stabilizer and another 880 bottles of liquid with mannitol for stabilizer.
1) We use continuous tube centrifugation to collect the AFOD enriched pellet;
2) Using Filtration to get rid of celite;
3) A 15 L DEAD chromatography for AFOD purification;
4) Virus inactivation including SD and DV 20;
5) Automatic filling.

AFCC RAAS 1: A current product of Shanghai RAAS Blood products Co Ltd approved for Sales in China and has been exported to a certain country around the globe. Product has been manufactured at large industrial scale.

Product has been used in the VITRO studies at Shanghai RAAS Blood Products Co Ltd
1. 3 Cancer Cell lines at R/D Lab
2. Bacteria at Microbiology Lab
3. HIV 1+2 Testing at NAT Lab In Vitro Studies of Cancer Cell Lines:
Procedures to test Cancer cells at RuiJin Hospital in Shanghai, China.

Cell Proliferation Assay by Using CCK 8 Test Kit

Check all Reagents at Least 3 Days Before Assay

Reagents:
1. Cancer cell line: Human colon cancer cell line (HCT-116), Human Breast cancer cell line (MCF-7), Human liver cancer cell line (HepG2), Human pancreatic cancer cell line (PAC-1)
2. CCK 8 (cell counting kit-8): Dojindo molecular technologies, Inc. (Maryland, US), product code # CK04-11
3. Cell culture medium:

| DMEM - high glucose 4.5 gm/L | Gibco (invitorgen) | 11965084 |
| ANTIBIOTIC ANTIMYCOTIC | Invitrogen | 15240062 |
| FBS | Hyclone | SH30071.03 |

4. AFOD: lyophilized formulation
Procedures:
Day −3 Before Treatment
1. Pre-Warm up cell culture medium to 37 C (DMEM/10% FBS/antibiotics)
2. Seed cells to a 15-cm dish and let cells grow 2-3 days to reach $2*10^8$ Day −1 Before Treatment
1. Pre-Warm up cell culture medium to 37 C (DMEM/2% FBS/antibiotics)
2. Seed cell at density of 2000/well in a 96-well plate. Triplicate every treatment condition.
    1) 0% AFOD
    2) 2% AFOD
    3) 10% AFOD
3. Leave cells for overnight growth Day 0 of Treatment
1. Pre-Warm up cell culture medium to 37 C (DMEM/2% FBS/antibiotics)
2. Change fresh medium in each for cells as following
    1) 0% AFOD: Cancer cell+fresh DMEM/2% FBS/antibiotics
    2) 2% AFOD: Cancer cell+1-4 diluted 10% AFOD with fresh DMEM/2% FBS/antibiotics
    3) 10% AFOD: Cancer cell+lyophilized AFOD dissolved in fresh DMEM/2% FBS/antibiotics
    4) Negative control: lyophilized AFOD dissolved in fresh DMEM/2% FBS/antibiotics only
3. Incubate cells for 2-3 days and observe cell growth everyday Day 1-2 after Treatment
Observation the proliferation of cells under microscopy
Day 3 after Treatment
1. Discard cell culture medium
2. Take picture of cell
3. Conduct the CCK8 assay according to manufacturer's instruction The antibiotics added in cell culture medium is basically to prevent the potential bacterial or fugal contamination during the culture. The antibiotics they added contains penicillin, streptomycin, and amphotericin B. Basically it won't kill cell and it is a routine recipe in animal cell culture. And they also include a control in which cells are cultured with DMEM/FBS/antibiotics only.

Reference is made to FIGS. 15-28.

The AFOD Anti-Tumor In Vitro Test Result

Procedures of Testing of cancer cells LS 174T (Colon), AGS (Gastric), and 45 (Gastric cancer cells at Shanghai RAAS R/D Lab procedures for both product AFODRAAS 1 and AFCCRAAS 1

Figure 29:
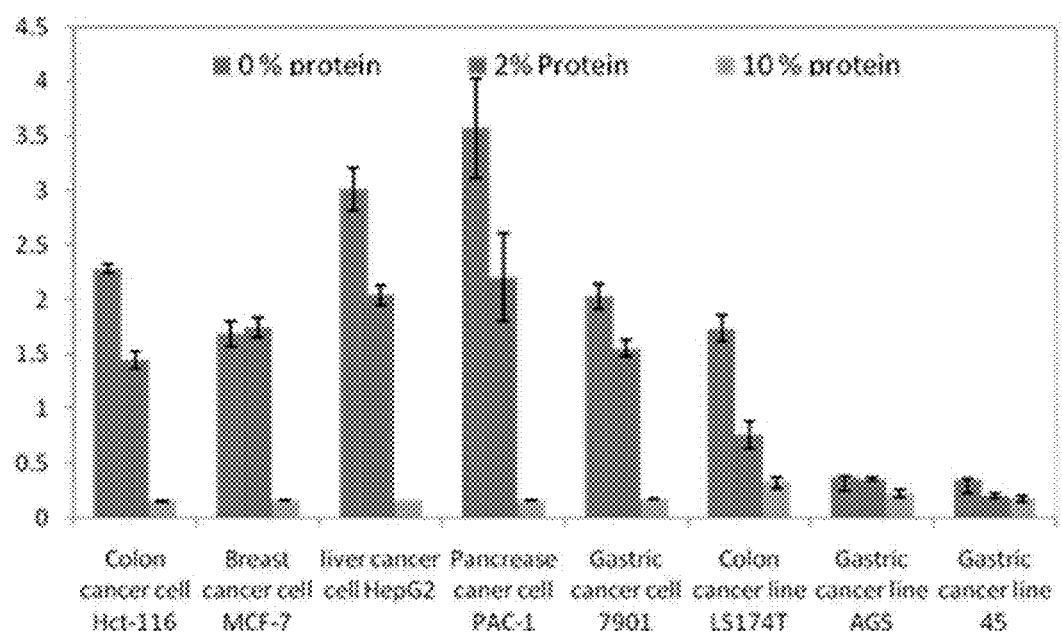
FIG. 29 is a graph showing the proliferation of a variety of cancer cells over a 3-day trial period in the presence of varying concentrations of AFOD.

The dose dependent cell killing effect of AFOD by CCK8 assay is shown in FIG. 29.

Figure 30:
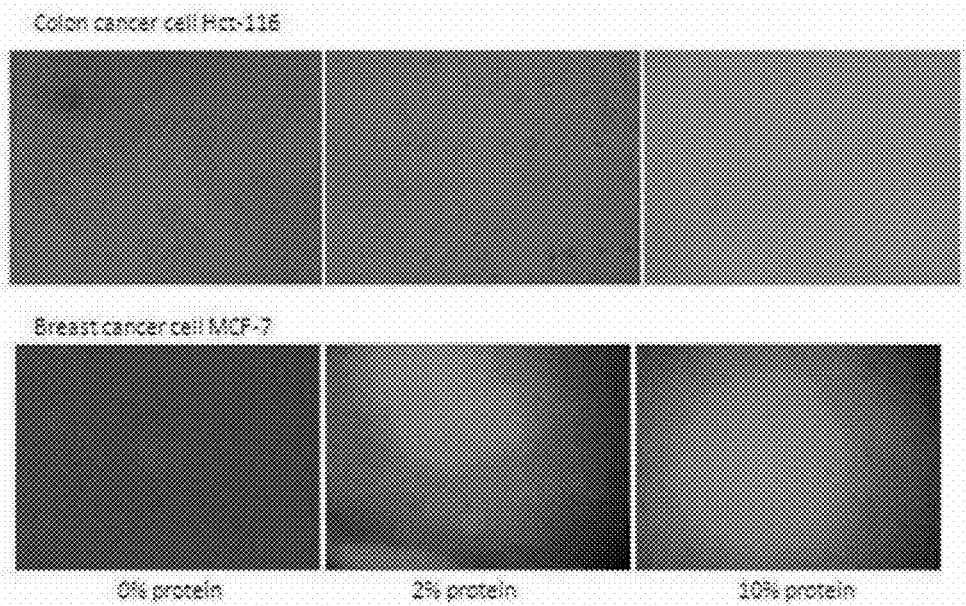
FIG. 30 shows the images of FIGS. 16-21 next to one another for comparison.
Figure 31:
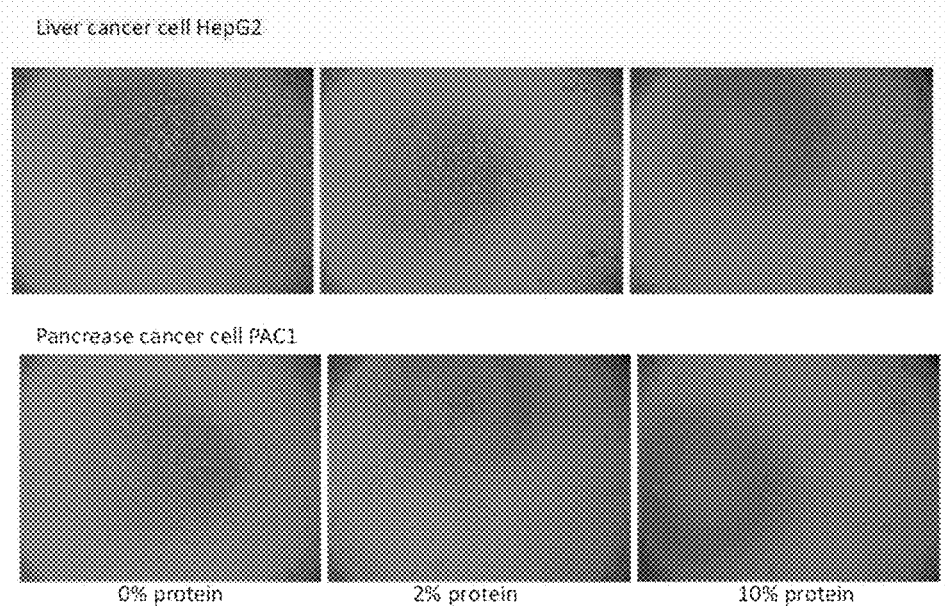
FIG. 31 shows the images of FIGS. 23-28 next to one another for comparison.
Figure 32:
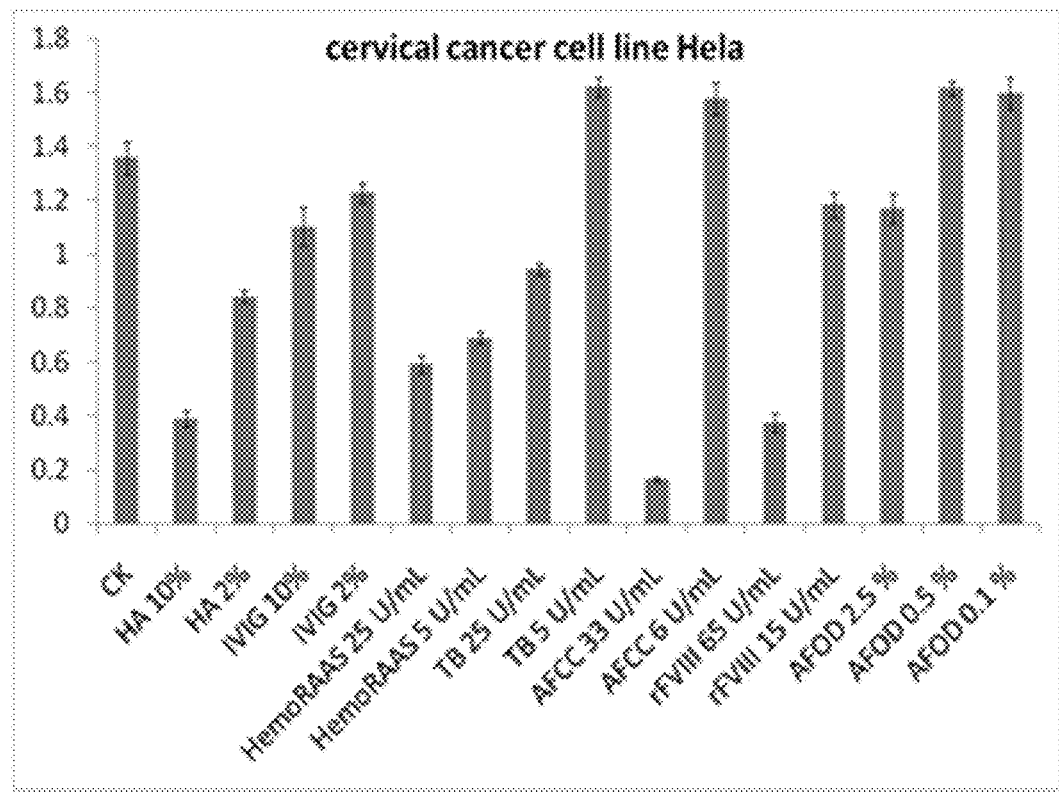
FIG. 32 is a graph showing cell proliferation during a 3-day in vitro study of cervical cancer cell line Hela in the presence of 16 distinct solutions, listed on the x axis. The solutions are CK, HA 10%, HA 2%, IVIG 10%, IVIG 2%, HemoRAAS 25 U/mL, HemoRAAS 5 U/mL, TB 25 U/mL, TB 5 U/mL, AFCC 33 U/mL, AFCC 6 U/mL, rFVIII 65 U/mL, rFVIII 15 U/mL, AFOD 2.5%, AFOD 0.5%. and AFOD 0.1%.

Pictures of the cancer cells are shown in FIGS. 30 and 31.

Method and materials used at Shanghai RAAS Blood Products Co Ltd R/D Dept.

Reagents:
1. Cancer cell line: Human colon cancer cell line (HCT-116), Human Breast cancer cell line (MCF-7), Human liver cancer cell line (HepG2), Human pancreatic cancer cell line (PAC-1)
2. CCK 8 (cell counting kit-8): Dojindo molecular technologies, Inc. (Maryland, US), product code # CK04-11

3. Cell culture medium:

| | | |
|---|---|---|
| DMEM - high glucose 4.5 gm/L | Gibco (invitorgen) | 11965084 |
| ANTIBIOTIC ANTIMYCOTIC | Invitrogen | 15240062 |
| FBS | Hyclone | SH30071.03 |

4. AFOD: lyophilized formulation
Procedures:
Day −3 Before Treatment
5. Pre-Warm up cell culture medium to 37 C (DMEM/10% FBS/antibiotics)
6. Seed cells to a 15-cm dish and let cells grow 2-3 days to reach $2*10^8$
Day −1 Before Treatment
4. Pre-Warm up cell culture medium to 37 C (DMEM/2% FBS/antibiotics)
5. Seed cell at density of 2000/well in a 96-well plate. Triplicate every treatment condition.
    4) 0% AFOD
    5) 2% AFOD
    6) 10% AFOD
6. Leave cells for overnight growth
Day 0 of Treatment
4. Pre-Warm up cell culture medium to 37 C (DMEM/2% FBS/antibiotics)
5. Change fresh medium in each for cells as following
7. 0% AFOD: Cancer cell+fresh DMEM/2% FBS/antibiotics
8. 2% AFOD: Cancer cell+1-4 diluted 10% AFOD with fresh DMEM/2% FBS/antibiotics
9. 10% AFOD: Cancer cell+lyophilized AFOD dissolved in fresh DMEM/2% FBS/antibiotics
10. Negative control: lyophilized AFOD dissolved in fresh DMEM/2% FBS/antibiotics only
6. Incubate cells for 2-3 days and observe cell growth everyday
    Day 1-2 after Treatment
    Observation the proliferation of cells under microscopy
    Day 3 after Treatment
11. Discard cell culture medium
12. Take picture of cell
13. Conduct the CCK8 assay according to manufacturer's instruction Further in vitro studies of more cancer cell lines are shown in FIGS. 32-61.

In vitro studies of bacteria performed at Shanghai RAAS Microbiology Lab Due to the large dosage to kill bacteria while product available are limited and saved for animal study of other diseases and cancers, this study does not completely kill all bacteria.

We performed bacteria experiments on AFOD RAAS 1 by both increasing the dosage of AFOD RAAS 1 and decreasing the density of testing bacteria. The current results will be listed in the following tables:

The amount of "+" in the following tables doesn't represent the accurate number of the testing bacteria remained in the medium after incubation; it represents the relative amount of them.

1. The microbe test with AFOD RAAS 1 on *Staphylococcus aureus* (a kind of aerobes)

| AFOD added (ml) | 16 hours | 24 hours | 40 hours | 72 hours |
|---|---|---|---|---|
| 0.5 ml *Staphylococcus aureus* + 0 ml AFOD | None | ++ | ++++ | ++++++++ |
| 0.5 ml *Staphylococcus aureus* + 8 ml AFOD | None | ++ | ++++ | ++++ |
| 0.5 ml *Staphylococcus aureus* + 10 ml AFOD | None | ++ | ++++ | ++++ |
| 0.5 ml *Staphylococcus aureus* + 12 ml AFOD | None | None | ++++ | ++++ |

In this experiment, we increased the dosage of AFOD (8 ml; 10 ml; 12 ml) to the medium. We found that the liquid culture medium converted to solid medium when we added 8 ml or more AFOD to the liquid medium and incubated for 24 hours. I think the main reason is the concentration of AFOD we added was too high. So maybe it's a little difficult to increase the dosage of AFOD anymore (such as 14 ml; 16 ml) even if the testing Staphylococcus aureus can still grow up when we added 12 ml AFOD to the medium.

2. The microbe test with AFOD RAAS 1 on *Micrococcus luteus* (a kind of aerobes)

| AFOD added (ml) | 16 hours | 24 hours | 40 hours | 72 hours |
|---|---|---|---|---|
| 0.5 ml *Micrococcus luteus* + 0 ml AFOD | None | None | ++++ | ++++++++ |
| 0.5 ml *Micrococcus luteus* + 8 ml AFOD | None | None | ++ | ++++++++ |
| 0.5 ml *Micrococcus luteus* + 10 ml AFOD | None | None | ++ | ++++++++ |
| 0.5 ml *Micrococcus luteus* + 12 ml AFOD | None | None | ++ | ++++++++ |

3. The microbe test with AFOD RAAS 1 on *Candida albicans* (a kind of fungus)

| AFOD added (ml) | 48 hours | 72 hours | 96 hours | 120 hours |
|---|---|---|---|---|
| 0.5 ml *Candida albicans* + 0 ml AFOD | ++ | ++++ | ++++++++ | ++++++++ |
| 0.5 ml *Candida albicans* + 4 ml AFOD | ++ | ++++ | ++++++++ | ++++++++ |
| 0.5 ml *Candida albicans* + 8 ml AFOD | ++ | ++++ | ++++++++ | ++++++++ |

4. The microbe test with AFOD RAAS 1 on *Aspergillus niger* (a kind of fungus)

| AFOD added (ml) | 48 hours | 72 hours | 96 hours | 120 hours |
|---|---|---|---|---|
| 0.5 ml *Aspergillus niger* + 0 ml AFOD | ++ | ++++ | ++++++++ | ++++++++ |
| 0.5 ml *Aspergillus niger* + 4 ml AFOD | ++++ | ++++++++ | ++++++++ | ++++++++ |
| 0.5 ml *Aspergillus niger* + 8 ml AFOD | ++++ | ++++++++ | ++++++++ | ++++++++ |

Reference is made to FIGS. 62-64.
HIV NAT Testing of AFODRAAS 1 and AFCC RAAS 1

| years | Total samples | HCV positive | % | positive | Percentage | positive | Percentage | positive | Percentage | positive | Percentage | positive | Percentage |
|---|---|---|---|---|---|---|---|---|---|---|---|---|---|
| 2006 | 633480 | 78 | 0.0123% | 162 | 0.0256% | 160 | 0.0253% | 5 | 0.0008% | 2 | 0.0003% | 7 | 0.0011% |
| 2007 | 345620 | 70 | 0.0203% | 50 | 0.0145% | 93 | 0.0269% | 0 | 0.0000% | 5 | 0.0014% | 6 | 0.0017% |
| 2008 | 428422 | 23 | 0.0054% | 43 | 0.0100% | 108 | 0.0252% | 0 | 0.0000% | 1 | 0.0002% | 18 | 0.0042% |
| 2009 | 524299 | 17 | 0.0032% | 45 | 0.0086% | 110 | 0.0210% | 0 | 0.0000% | 3 | 0.0006% | 0 | 0.0000% |
| 2010 | 554297 | 53 | 0.0096% | 31 | 0.0056% | 131 | 0.0236% | 0 | 0.0000% | 5 | 0.0009% | 0 | 0.0000% |
| 2006~2010 | 2486118 | 241 | 0.0097% | 331 | 0.0133% | 602 | 0.0242% | 5 | 0.0002% | 16 | 0.0006% | 31 | 0.0012% |

The above table show HCV, HIV1,2 and HBsAg on the left are Elisa testing HCV-RNA HIVRNA, HBV DNA are results of NAT Testing at Shanghai RAAS NAT Laboratory for A total of units of plasma 2,486,188 during five years period from 2006 to 2010. Out of these number of units, there were 241 tested positive HCV by Elisa, confirmed HCV positive by NAT is only 5 units so a total of 236 units are false positive by Elisa Method. From 2007 to 2010 there is no HCV positive from our donor population therefore we have No Hepatitis B Virus to test for our study. Further study will be done when receiving samples from Infectious disease hospital in Shanghai which will also carry out animal study for all HIV, HCV and HBV.

For HIV 1,2 by Elisa had 331 positive and confirmed by NAT is only 16 so false positive is 315 units. Luckily our R/D still had 1 sample of positive HIV1,2 to conduct this study. For HBV we had a total of 602 positive by Elisa and 31 confirmed by NAT total false positive by Elisa is 571 samples. In 2009 and 2010 we had no positive sample confirmed by NAT.

To avoid the large dosage of limited AFODRAAS and AFCCRAAS, NAT Lab has diluted the positive plasma sample to weaken the presence of HVI1,2 virus to the level of 1:3200 and the first test result is as below for the HIV Positive Plasma to use as A CONTROL.
HIV positive plasma (60051215) 5.9E+6 IU/ml
the plasma (1:100) 3E+5 IU/ml
the plasma (1:200) 1.1E+5 IU/ml
the plasma (1:400) 5.4E+4 IU/ml
the plasma (1:800) 2.9E+4 IU/ml
the plasma (1:1600) 1.4E+4 IU/ml
the plasma (1:3200) 5.7E+3 IU/ml
Sample incubation at room temperature until Day 3 Concentration
20 ml of the plasma (1:800)+2 bottles of AFODRAAS1 2.3E+4 IU/ml
20 ml of the plasma (1:1600)+2 bottles of AFODRAAS 1 5.9E+3 IU/ml
20 ml of the plasma (1:3200)+2 bottles of AFODRAAS1 1.9E+3 IU/ml
20 ml of the plasma (1:800)+2 bottles of AFCCRAAS 1 1.3E+4 IU/ml
20 ml of the plasma (1:1600)+2 bottles of AFCC RAAS 1 2.9E+3 IU/ml
20 ml of the plasma (1:3200)+2 bottles of AFCC RAAS 1 56 IU/ml As shown in the table above, we have observed HIV1,2 Positive Sample mixed With AFODRAAS 1 and AFCC RAAS 1 have reduced Number of IU/MI The second test results show as below there is a significant drop from 29000 IU/ml of Positive Plasma Control down to 4500 IU/ml due to the decade of HIV1,2 Virus in the plasma; Thus we conduct further test to assure by using NON DILUTED SAMPLES even though we have to increase dosage of AFOD RAAS1 and AFCCRAAS 1 to cope with high concentration of HIV1,2 virus. However it is an experimental test that needs further STUDIES.

| Sample | Initial concentration | Day 3 Concentration |
|---|---|---|
| the positive plasma(1:800) | 29000 IU/ml | 4500 IU/ml |
| the positive plasma(1:1600) | 14000 IU/ml | 2100 IU/ml |
| the positive plasma(1:3200) | 5700 IU/ml | 670 IU/ml |
| 20 ml of the positive plasma(1:800) + 2 bottles of AFODRAAS 1 | 29000 IU/ml | 13000 IU/ml |
| 20 ml of the positive plasma(1:1600) + 2 bottles of AFODRAAS 1 | 14000 IU/ml | 6300 IU/ml |
| 20 ml of the positive plasma(1:3200) + 2 bottles of AFODRAAS1 | 5700 IU/ml | 2500 IU/ml |
| 20 ml of the positive plasma(1:800) + 2 bottles of AFCC RAAS1 | 29000 IU/ml | 4600 IU/ml |
| 20 ml of the positive plasma(1:1600) + 2 bottles of AFCC RAAS 1 | 14000 IU/ml | 620 IU/ml |
| 20 ml of the positive plasma(1:3200) + 2 bottles of AFCC RAAS1 | 5700 IU/ml | 130 IU/ml |
| 20 ml of the positive plasma(1:800) + 1 bottle of AFODRAAS + 1 bottle of AFCC | 29000 IU/ml | 22000 IU/ml |
| 20 ml of the positive plasma(1:1600) + 1 bottle of AFODRAAS + 1 bottle of AFCC | 14000 IU/ml | 2800 IU/ml |
| 20 ml of the positive plasma(1:3200) + 1 bottle of AFODRAAS + 1 bottle of AFCC | 5700 IU/ml | 110 IU/ml |

In Vivo Study

Experimental Design and Results of Pilot Scale

Pre-clinical Animal Test of AFOD RAAS 1

For the Antiatherogenic and Cholesterol-Lowing Properties

1. Purpose of the Experiments:
1.1 To test the effects of AFOD RAAS 1 for the suppression of fatty streak lesions.
1.2. To test the efficiency of making animal models for atherosclerosis
1.3 To test the efficacy and dosage for AFOD RAAS 1 in the suppression of fatty streak lesions and cholesterol-related plasma indicators
2. Experimental Design
2.1 Experimental Animals.

Male New Zealand white-ear or other strain healthy rabbits (2.0 kg body weight, 4 in each group)$^{were}$ used in the experiment.
2.2 Experimental Model Construction The rabbits were fed with normal diet under regular lab conditions for 5-10 days. The rabbits were fasted for 12 hrs before the beginning of the experiments. Blood parameters were then tested as the normal level of plasma indicators. The animals were then randomly grouped for the experiment.
2.3 Treatments After grouping of the experimental animals, they were switched to high-fat diet. Body weight and plasma parameters were tested and recorded once every two weeks until indicators shown to have lipid metabolism disorders and the formation of obvious fatty streak lesions in blood vessels. The animals were switched from high-fat diet to normal diet. These are the grouping of the experimental animals: (1) positive control group, (2) AFOD RAAS 1-Al treatment group was further divided into high, medium and low three dose sub-groups. During the first 4 weeks of the AFOD RAAS 1-treatment, plasma parameters and animal general conditions were carefully monitors and recorded. At the end of the experiments, the lab animals were sacrificed for pathological and anatomical analysis.
2.4 Parameters Tested:
1) blood cholesterol-related parameters:
   TC: total cholesterol
   TG: tri-glyceride
   LDL-C: low density lipoprotein—LDL
   VLDL-C: very low density lipoprotein—VLDL
   HDL-C: high density lipoprotein—HDL
   TC/HDL-C or (LDL-C+VLDL-C)/HDL-C: ratio
2) pathological tests
   pathology in aorta (main artery)
3) Liver index
3. Experimental Process A total of 52 rabbits were purchased at different time, four of them were used as normal control and fed with normal diet the whole time during the experiments. There rest of the animals was switched to high fat diet.

Some of the lab animals showed stomach symptoms after switched to high-fat diet and died within 4 weeks. From week 7 to week 10, 6 more lab animals died for the same reason. At week 10 and 11, two animals were sacrificed as animal model control. These two animals were dissected to obtain aorta, heart and liver tissue samples. Observation: the appearance of the aorta and liver were observed and recorded. The inside surface of aorta has obvious fatty streak deposit and lesion. The liver tissue has white fatty tissue deposit. Taken together, the construction of the animal models was successful. Two lab animals from the normal control group were also sacrificed and dissected. No abnormality of aorta and liver tissues were observed.

The rest 34 rabbits were then switched to normal diet and grouped into animal-model group, positive control group and low, medium and high dosage AFOD RAAS 1-Al treatment groups.

Animal-model group (no AFOD RAAS 1 and normal diet): 4

Positive control: 5

AFOD RAAS 1-Al treatment group:

High dosage group (100 mg/each), average body weight 2.8 kg: 11

Medium dosage group (50 mg/each): 8

Low dosage group (25 mg/each): 6

After 4 weeks of treatment, two lab animals from the high-dosage group were sacrificed and dissected. No significant changes of fatty streak lesions were observed. Based on this observation, all of the lab animals from the experimental groups were switched to high-dosage AFOD RAAS 1 treatment, which is 100 mg/each.
4. Experimental Results
4.1 Duration of the Animal Model Construction After feeding of the lab animals with high-fat diet (1.5% cholesterol, 3% lard, and normal feed) for four weeks, all cholesterol-related plasma parameters were increased significantly (see attached data sheet). At week 4, one of the lab animals were sacrificed and showed limited amount of fatty streak lesions. At week 10 and week 11, five lab animals were sacrifices and dissected. Obvious fatty streak lesions can be observed on the inside surface of the aorta. Fat deposit can also be observed on the liver tissues.

Conclusion: At week 10-11, fatty streak lesions were formed.
4.2 Successful Rate for Model Construction During the animal model construction, 7 animals died during the first 4 weeks of high-fat diet due to stomach symptoms. Between week 7-10, 6 more lab animals died because of high-fat. The mortality rate is 16.7%. These lab animals were also dissected and 90% of them the aorta tissue showed fatty streak lesions occupied 20% of the total area.

Conclusion: the successful rate of model construction is 60%.

Models (high fat diet, execute at 10 weeks, the picture of the aorta, with a Plaque area=24.3%) is shown in FIG. 65. Reference is also made to FIG. 66.

Control group (build up the animal models, without AFOD RAAS 1, then normal diet for 4 weeks) Plaque area=45.3%, as can be appreciated from FIG. 67.

Control groups (build up the animal models, without AFOD RAAS 1, then normal diet for 8 weeks). FIG. 68 shows a Plaque area=98.5%, and FIG. 69 shows a plaque area=78.94%.
4.3 Plasma Parameters 1) First 8 weeks of treatment (n=7, for the first 4 weeks, AFOD RAAS 1 was administered once a week and 100 mg/each; in the following 4 weeks, 50 mg/each were administered twice a week)

|  | Weight | TG | TCH | VLDL-C | HDL-C | LDL-C | TC/HDL-C |
|---|---|---|---|---|---|---|---|
| Start | 2.164 | 0.967 | 1.152 | 0.870 | 0.748 | 0.282 | 1.938 |
| Before | 2.7 | 5.191 | 36.153 | 14.996 | 8.261 | 21.157 | 6.560 |
| After | 2.79 | 1.17 | 3.69 | 1.09 | 1.46 | 2.60 | 3.000 |

2) At week 11 of the experiment (n=7, for the first 4 weeks, AFOD RAAS 1 was administered once a week and 100 mg/each; in the following 4 weeks, 50 mg/each were administered twice a week, for the last 3 weeks, 100 mg/each were administered once a week)

|  | Weight | TG | TCH | VLDL-C | HDL-C | LDL-C | TC/HDL-C |
|---|---|---|---|---|---|---|---|
| Start | 2.2 | 0.93 | 1.430 | 0.958 | 0.432 | 0.472 | 4.185 |
| Before | 2.45 | 4.507 | 34.683 | 15.443 | 10.168 | 19.24 | 3.667 |
| After | 2.65 | 1.94 | 3.322 | 1.14 | 1.17 | 2.19 | 3.844 |

3) Positive control (Crestor, administered 4 weeks)

|  | Weight | TG | TCH | VLDL-C | HDL-C | LDL-C | TC/HDL-C |
|---|---|---|---|---|---|---|---|
| Start | 2.25 | 0.450 | 0.946 | 0.509 | 0.539 | 0.437 | 1.844 |
| Before | 2.85 | 9.122 | 20.339 | 9.710 | 8.404 | 10.911 | 4.511 |
| After | 3.1 | 0.474 | 8.535 | 3.675 | 1.25 | 4.86 | 6.811 |

4) control (statin) (n=4)

|  | Weight | TG | TCH | VLDL-C | HDL-C | LDL-C | TC/HDL-C |
|---|---|---|---|---|---|---|---|
| Start | 2.113 | 0.843 | 1.444 | 0.885 | 0.684 | 0.559 | 2.108 |
| Before | 2.742 | 2.666 | 32.42 | 7.467 | 5.657 | 24.953 | 9.459 |
| End | 3.1 | 1.207 | 5.277 | 1.961 | 0.759 | 3.316 | 6.458 |

5) Summary of plasma parameter data

|  | Weight | TG | TCH | VLDL-C | HDL-C | LDL-C | TC/HDL-C |
|---|---|---|---|---|---|---|---|
| Model Group Week 8 | | | | | | | |
|  | −0.050 | −0.343 | −31.114 | −9.225 | −8.484 | −21.889 | 2.003 |
|  | −0.020 | −1.995 | −21.839 | −4.053 | −5.763 | −17.786 | 0.345 |
|  | −0.020 | −1.632 | −26.320 | −0.570 | −4.698 | −25.750 | 2.918 |
|  | 0.250 | −1.866 | −29.300 | −8.175 | −4.648 | −21.125 | 0.303 |
| Sum | 0.160 | −5.836 | −108.573 | −22.023 | −23.593 | −86.550 | 5.568 |
| Ave | 0.023 | −0.834 | −15.510 | −3.146 | −3.370 | −12.364 | 0.795 |
| AFOD RAAS 1 Group Week 8 | | | | | | | |
|  | 0.200 | −19.259 | −28.873 | −5.730 | −17.483 | −23.143 | 1.863 |
|  | 0.250 | −4.061 | −25.631 | −12.718 | −9.323 | −12.913 | −0.034 |
|  | 0.200 | −0.487 | −26.677 | −14.607 | −5.932 | −12.070 | −2.164 |
|  | −0.100 | 0.677 | −31.438 | −13.629 | −4.971 | −17.809 | −2.739 |
|  | −0.100 | −0.211 | −39.804 | −15.867 | −3.983 | −23.937 | −6.655 |
|  | 0.200 | −3.394 | −41.059 | −23.550 | −1.933 | −17.509 | −13.858 |
|  | 0.000 | −1.432 | −33.792 | −11.265 | −3.955 | −22.527 | −4.051 |
| Sum | 0.650 | −28.167 | −227.274 | −97.366 | −47.580 | −129.908 | −27.638 |
| Ave | 0.093 | −4.024 | −32.468 | −13.909 | −6.797 | −18.558 | −3.948 |
| ApoAI (n = 5) | 0.0500 ± 0.1658 | −1.1028 ± 1.8167 | −31.4684 ± 5.7427 | −13.6172 ± 1.7595 | −5.6328 ± 2.2182 | −17.8512 ± 5.4016 | −3.1286 ± 2.4466 |
| Model group | 0.0400 ± 0.1407 | −1.4590 ± 0.7590 | −27.1432 ± 4.0510 | −5.5058 ± 3.9762 | −5.8982 ± 1.7989 | −21.6375 ± 3.2697 | 1.3920 ± 1.2890 |
| P value | 0.926 | 0.727 | 0.246 | 0.004 | 0.852 | 0.26 | 0.013 |

Conclusion: After 8 weeks of AFOD RAAS 1 treatment, all cholesterol-related plasma parameters decreased. There is also a decrease in the model control group. Significant changes can only be observed in VLDL-C and TC/HDL-C ($p<0.05$). There is no significant change for the rest of the parameters.

| AFOD RAAS 1 group Week 11 | | | | | | | |
|---|---|---|---|---|---|---|---|
|  | Weight | TG | TCH | VLDL-C | HDL-C | LDL-C | TC/HDL-C |
|  | 0.200 | −4.241 | −30.064 | −8.388 | −10.183 | −21.676 | 1.294 |
|  | 0.300 | −3.740 | −31.052 | −7.169 | −8.799 | −23.883 | −2.282 |
|  | 0.000 | 0.092 | −29.618 | −19.679 | −11.844 | −9.939 | −0.164 |
|  | 0.300 | −2.374 | −34.708 | −21.989 | −5.151 | −12.719 | −1.978 |
| Sum | 0.800 | −10.263 | −125.442 | −57.225 | −35.977 | −68.217 | −3.129 |
| Ave | 0.200 | −2.566 | −31.361 | −14.306 | −8.994 | −17.054 | −0.782 |

| | AFOD RAAS 1 group Week 11 | | | | | | |
|---|---|---|---|---|---|---|---|
| | Weight | TG | TCH | VLDL-C | HDL-C | LDL-C | TC/HDL-C |
| Model | 0.0400 ± 0.1407 | −1.4590 ± 0.7590 | −27.1432 ± 4.0510 | −5.5058 ± 3.9762 | −5.8982 ± 1.7989 | −21.6375 ± 3.2697 | 1.3920 ± 1.2890 |
| AFOD RAAS 1 11 wk | 0.2000 ± 0.1414 | −2.5658 ± 1.9396 | −31.3605 ± 2.3107 | −14.3062 ± 7.6126 | −8.9942 ± 2.8486 | −17.0542 ± 6.7679 | −0.7824 ± 1.6706 |
| P value | 0.689 | 0.99 | 0.532 | 0.11 | 0.658 | 0.583 | 0.795 |

Conclusion: All cholesterol-related parameters showed significant decrease. But compared with the control group, there is no statistical significance.

6) Changes of HDL-C:

| | normal | AFOD RAAS 1 treatment | increase | Fold increase |
|---|---|---|---|---|
| 8 wks | 0.748 | 1.464 | 0.716 | 1.436 |
| 11 wks | 0.432 | 1.423 | 0.992 | 3.078 |
| control | 0.684 | 0.759 | 0.074 | 0.102 |

Compare the HDL-C values before and after the treatment, it indicated that HDL-C is elevated after AFOD RAAS 1-Al treatment Conclusion, iv infusion of AFOD RAAS 1 could lower blood cholesterol through the formation of HDL.

The invention reveals that all healthy good cells have eaten all fats (BAD CELLS and damaged cells as described in the function of the liver not through the formation of HDL. In this preliminary and small study, The Inventor has found that even with the longer And higher dosage of AFOD RAAS 1 Group 2, the formation of HDL has been reduced to 54.15% from 92.36% of AFODRAAS 1 Group 1 and the Total of TC/HDL-C is −53.55% much higher than to compare with AFODRAAS 1 Group 2 which has TC/HDL-C −40.48% To prove it, Atorvastatin® was also used in this study when comparing with control group, it has significantly reduced TG −60.73% and increased HDL to 64.69% however

| | Weight | TG | TCH | VLDL-C | HDL-C | LDL-C | TC/HDL-C |
|---|---|---|---|---|---|---|---|
| control | 3.1 | 1.207 | 5.277 | 1.961 | 0.759 | 3.316 | 6.458 |
| AFOD 1 | 2.79 | 1.17 | 3.69 | 1.09 | 1.46 | 2.6 | 3 |
| compare to control | −10.00% | −3.07% | −30.07% | −44.42% | 92.36% | −21.59% | −53.55% |
| AFOD 2 | 2.65 | 1.94 | 3.322 | 1.14 | 1.17 | 2.19 | 3.844 |
| compare to control | −14.52% | 60.73% | −37.05% | −41.87% | 54.15% | −33.96% | −40.48% |
| Atorvastatin | 3.1 | 0.474 | 8.535 | 3.675 | 1.25 | 4.86 | 6.811 |
| compare to control | 0.00% | −60.73% | 61.74% | 87.40% | 64.69% | 46.56% | 5.47% |

TCH have increased to 61.74%, VLDL-C increased 87.40% LDL-C increased 46.56% and TC/HDL-C is 5.47%. In conclusion it can reduces TG and increases HDL but will NOT LOWER Bad Cholesterol VLDL-C, LDL-C, TCH and TC/DHL-C Drugs like Atorvastatin® cannot remove FATS from PLAQUE whereas AFODRAAS1 and AFCCRAAS1 CAN REMOVE FATS from PLAQUE, CLEAN the arteries.

In the first year of high school, we began to learn that when the YELLOW COLOR Mixed with BLUE, it turns GREEN. In a drug if you have to have a YELLOW COLOR and BLUE COLOR for your final product, It is IMPOSSIBLE as the final product will turn GREEN. This is the reason why Chemicals REACT that is why most of drugs from Chemicals have SIDE EFFECTS.

There is only ONE MANUFACTURER, MODERATOR, REGULATOR and DISTRIBUTOR which can produce the product which maintains the YELLOW COLOR and BLUE COLOR is THE LIVER producing PILE approximately 0.5-0.9 liter of PILE per day. PILE is a LIQUID which has YELLOW COLOR and BLUE COLOR.

Reference is made to FIGS. 70-76.

Therefore in this case, ATORVASTATIN® is one among thousands of drugs available can be combined with AFODRAAS1-85 or AFCC RAAS1-85 to enhance the EFFICACY of the drugs. Before this invention, Drugs like ATORVASTATIN® and LIPITOR® have helped a lot of people with HIGH CHOLESTEROL.

Liver

1) Liver surface: When the animal models were first made, the liver surface of the lab animals from the animal-model group showed abnormal white colored spots. Histological analysis showed that it is???. The surface of the liver feels harder than normal tissue. The liver samples taken from the —Al treated group has fewer???. The surface is not as tough as when the animal model was first made. The un-treated group also showed relief in the??? and softened. The probable reason is that because the high cholesterol and atherosclerosis model is made in a short period of time, the switch to normal diet also helped to relief the symptoms.

2) Liver index

| | weight (g) | Liver index |
|---|---|---|
| ApoAI 8 weeks | 0.09 | 0.033 |
| ApoAI 11 weeks | 0.117 | 0.044 |
| model control | 0.111 | 0.036 |

The liver index did not show any changes after the AFOD RAAS 1 treatment. 6 fatty streak lesions

|  | Area | Compare to control | Increase % | Compare to model control | Decrease % |
|---|---|---|---|---|---|
| AFOD RAAS 1 8 wk | 43.84 | 19.03 | 77 | −27.36 | 38.43 |
| AFOD RAAS 1 11 wk | 50.51 | 25.71 | 104 | −20.69 | 29.05 |
| Model control | 71.20 | 46.39 | 187 |  |  |
| Model first made | 24.81 |  |  |  |  |

1) Fatty streak lesion appearance: the tissue from the non-AFOD RAAS 1-group (model control) has bumps on the surface. The tissue feels tender and hard as touched with bare hand. Dissection of the blood vessels showed fat deposit in the cross-section of the tissue. The fatty streak lesion decreases as the aorta descends. Compare with the model control group, the AFOD RAAS 1-group do not have bumps in the blood vessel surface. The tissue feels soft as touched with bare hand.

2) Area measurement of the fatty streak lesion: Compare with the model-control group, the surface area of the fatty streak lesion increased 77% and 104%, and the non-AFOD RAAS 1-treated group increased by 187%. Compare with the non-AFOD RAAS 1-Al treated group, the fatty streak lesion of the AFOD RAAS 1-group decreased by 38.43% at week 8 and decreased by 29.05% at week 11.

Conclusion: Administration of AFOD RAAS 1 to the lab animals with atherosclerosis obviously suppresses the further development of fatty streak lesion.

Drugs like Atorvastatin® cannot remove FATS from PLAQUE whereas AFODRAAS1-85 and AFCCRAAS1-85 CAN REMOVE FATS from PLAQUE, CLEAN the arteries. FIG. 77 shows Normal (normal diet 8 weeks) and FIG. 78 shows Plaque area=0. FIGS. 79 and 80 show build up the animal models, with AFOD RAAS 1-Al 8 weeks. FIG. 79 shows Plaque area=13.29%, and FIG. 80 shows Plaque area=20.5%. FIGS. 81 and 82 show build up the animal models, with AFOD RAAS 1 8 weeks (another rabbit). FIG. 81 shows Plaque area=58.4%, and FIG. 82 shows Plaque area=82.17%.

FIGS. 83-85 show Group with AFOD RAAS 1 11 weeks. FIG. 83 shows Plaque area=47.27%, FIG. 84 shows Plaque area=40.32%, and FIG. 85 shows Plaque area=51.13%.

3) Analysis of lipid content at dissected aorta

|  | lipid con. (umol/mg) | sig |  |
|---|---|---|---|
| 8 weeks (n = 7) | 0.025 ± 0.0095 | 0.006 | p < 0.01 |
| 11 weeks (n = 4 | 0.0267 ± 0.0054 | 0.015 | p < 0.05 |
| positive control (n = 4) | 0.0274 ± 0.006 | 0.046 | p < 0.05 |
| Control (n = 4) | 0.0736 ± 0.014 |  |  |

Conclusion: Comparing with the model control group, the triglyceride content at dissected aorta of the AFOD RAAS 1 treated group is significantly lowered. The decrease is significant statistically. ($p<0.05$).

5. Experimental Summary

The purpose of this pilot-scale preclinical animal test of AFOD RAAS 1 is the successful rate and time estimate of making animal model of atherosclerosis, dose and effects human AFOD RAAS 1-Al administration on the blood cholesterol-related levels and the suppression of development of fatty streak lesion.

Based on data collected from the experiment, successful making of a high cholesterol rabbit model need 4-5 weeks. The formation of atherosclerosis fatty streak lesion need more than 10 weeks of high-fat diet (at week 10-11, the average surface area of fatty streak lesion is 24%). The successful rate for model making is 60%. After intravenous infusion of human AFOD RAAS 1 at 100 mg/wk for 8-11 weeks, the hypercholesterolemia and liver lesion improved dramatically, but the does not stop the formation of fatty streak lesion at aorta. Thus, the hypercholesterolemia and liver lesion can slowly regress after switch to low fat diet, but the atherosclerosis fatty streak lesion progresses and need to be treated.

The experiment shows that the administration of AFOD RAAS 1 to hypercholesterolemia lab animals reduces the surface area of fatty streak lesion at aorta and decreases the triglyceride content in the lesion tissue, thus; AFOD RAAS 1 has the potential to be developed to be an antiatherogenic and cholesterol-lowering medicine.

Table 1. The Change of Plasma Lipid Parameter

1. Wk0, wk10 and wk18 mean the actual value of each parameter.
2. Wk18−wk0 (or wk21−wk0) means the change calculated by comparing the value of wk 18 (or wk21) to the value of wk 0. This means the overall results during the whole process, which means (high fat diet+switch to normal diet+different treatment). It is calculated by % of change=(value of wk18−value of wk 0)/value of wk 0.
3. Wk18−wk10 (or wk21−wk10) means the change calculated by comparing the value of wk 18 (or wk21) to the value of wk 10. This represents the results during the second half process, which means (switch to normal diet+different treatment). It is calculated by % of change=(value of wk18−value of wk 10)/value of wk 10.
4. Please refer to table 2 for the experiment design

|  | Weight | TG | TCH | VLDL-C | HDL-C | LDL-C | TC/HDL-C |
|---|---|---|---|---|---|---|---|
| AFODRAAS 1 treatment for 8 weeks ||||||||
| wk 0 | 2.164 | 0.967 | 1.152 | 0.87 | 0.748 | 0.282 | 1.938 |
| wk 10 | 2.7 | 5.191 | 36.153 | 14.996 | 8.261 | 21.157 | 6.56 |
| wk 18 | 2.79 | 1.17 | 3.69 | 1.09 | 1.46 | 2.6 | 3 |
| wk 18−wk 0 | 28.93% | 20.99% | 220.31% | 25.29% | 95.19% | 821.99% | 54.80% |
| wk 18−wk 10 | 3.33% | −77.46% | −89.79% | −92.73% | −82.33% | −87.71% | −54.27% |

-continued

|  | Weight | TG | TCH | VLDL-C | HDL-C | LDL-C | TC/HDL-C |
|---|---|---|---|---|---|---|---|
| AFODRAAS 1 treatment for 11 weeks | | | | | | | |
| Wk 0 | 2.2 | 0.93 | 1.43 | 0.958 | 0.432 | 0.472 | 4.185 |
| Wk 10 | 2.45 | 4.507 | 34.683 | 15.443 | 10.168 | 19.24 | 3.667 |
| Wk 21 | 2.65 | 1.94 | 3.322 | 1.14 | 1.17 | 2.19 | 3.844 |
| wk 21-wk 0 | 20.45% | 108.60% | 132.31% | 19.00% | 170.83% | 363.98% | −8.15% |
| wk 21-wk 10 | 8.16% | −56.96% | −90.42% | −92.62% | −88.49% | −88.62% | 4.83e% |
| Atorvastatin Atorvastatin for 4 weeks | | | | | | | |
| Wk 0 | 2.25 | 0.45 | 0.946 | 0.509 | 0.539 | 0.437 | 1.844 |
| Wk 10 | 2.85 | 9.122 | 20.339 | 9.71 | 8.404 | 10.911 | 4.511 |
| Wk 18 | 3.1 | 0.474 | 8.535 | 3.675 | 1.25 | 4.86 | 6.811 |
| wk 18-wk 0 | 37.78% | 5.33% | 802.22% | 622.00% | 131.91% | 1012.13% | 269.36% |
| wk 18-wk 10 | 8.77% | −94.80% | −58.04% | −62.15% | −85.13% | −55.46% | 50.99% |
| control | | | | | | | |
| Wk 0 | 2.113 | 0.843 | 1.444 | 0.885 | 0.684 | 0.559 | 2.108 |
| Wk 10 | 2.742 | 2.666 | 32.42 | 7.467 | 5.657 | 24.953 | 9.459 |
| Wk 18 | 3.1 | 1.207 | 5.277 | 1.961 | 0.759 | 3.316 | 6.458 |
| wk 18-wk 0 | 46.71% | 43.18% | 265.44% | 121.58% | 10.96% | 493.20% | 206.36% |
| wk 18-wk 10 | 13.06% | −54.73% | −83.72% | −73.74% | −86.58% | −86.71% | −31.73% |

TABLE 2

The experiment design

|  | Wk 0 | Wk 10 | Wk 14 | Wk 18 | Wk 21 |
|---|---|---|---|---|---|
| Control group | Establish animal model with high fat diet | Normal diet without APOAI | | | |
| APOAI group 1 | Establish animal model with high fat diet | APOAI 100 mg/animal once a week | APOAI 50 mg/animal twice a week | No APOAI | |
| APOAI group 2 | Establish animal model with high fat diet | APOAI 100 mg/animal once a week | APOAI 50 mg/animal once a week | APOAI 100 mg/animal once a week | |
| Atorvastatin group | Establish animal model with high fat diet | Atorvastatin | | | |

TABLE 3 change of fatty streak lesions

|  | Time point | Fatty streak lesions area (%) | Compare to wk 10 of control group Increase % | Compare to wk 18 of control group Decrease % |
|---|---|---|---|---|
| AFODRAAS 1 Group 1 | Wk 18 | 43.84 | 19.03 | 77 | −27.36 | 38.43 |
| AFODRAAS 1 Group 2 | Wk 21 | 50.51 | 25.71 | 104 | −20.69 | 29.05 |
| Atrovastatin | Wk 18 | 71.20 | 46.39 | 187 | | |
| Control group | Wk 10 | 24.81 | | | | |

TABLE 4

Analysis of lipid content at dissected aorta

|  | Lipid con. (umol/mg) | P value (compared to control group) |
|---|---|---|
| AFODRAAS 1 Group 1 (n = 7) | 0.025 ± 0.0095 | 0.006 |
| AFODRAAS 1 Group 2 (n = 4) | 0.0267 ± 0.0054 | 0.015 |
| Atorvastatin group (n = 4) | 0.0274 ± 0.006 | 0.046 |
| Control group (n = 4) | 0.0736 ± 0.014 | |

|  | Weight | TG | TCH | VLDL-C | HDL-C | LDL-C | TC/HDL-C |
|---|---|---|---|---|---|---|---|
| control | 3.1 | 1.207 | 5.277 | 1.961 | 0.759 | 3.316 | 6.458 |
| AFOD 1 | 2.79 | 1.17 | 3.69 | 1.09 | 1.46 | 2.6 | 3 |
| compare to control | −10.00% | −3.07% | −30.07% | −44.42% | 92.36% | −21.59% | −53.55% |
| AFOD 2 | 2.65 | 1.94 | 3.322 | 1.14 | 1.17 | 2.19 | 3.844 |
| compare to control | −14.52% | 60.73% | −37.05% | −41.87% | 54.15% | −33.96% | −40.48% |
| Atorvastatin | 3.1 | 0.474 | 8.535 | 3.675 | 1.25 | 4.86 | 6.811 |
| compare to control | 0.00% | −60.73% | 61.74% | 87.40% | 64.69% | 46.56% | 5.47% |

The invention claimed is:

1. A method of purifying aplipooprotein A-I (APOA1) from plasma fraction IV comprising:
    suspending plasma fraction IV in a buffer to obtain a resulting supernatant, wherein the buffer has a pH level in the range of 3.0 to 10.0, and wherein the resulting supernatant contains APOA1;
    collecting the resulting supernatant;
    adding a sodium chloride solution to the resulting supernatant and obtaining an APOA1 precipitate solution;
    centrifuging the APOA1 precipitate solution and collecting a resulting APOA1 paste;
    suspending the resulting APOA1 paste and obtaining a resulting APOA1 suspension;
    filtering the resulting APOA1 suspension and obtaining a resulting filtered APOA1 suspension; and
    subjecting the resulting filtered APOA1 suspension to a chromatography process.

2. The method according to claim 1, wherein the buffer is a sodium acetate solution.

3. The method according to claim 1, wherein the sodium chloride solution has a pH level in the range of 3.0 to 10.0, and wherein the APOA1 precipitate solution is cooled to a temperature range of −1° C. to 1° C.

4. The method according to claim 1, wherein the APOA1 paste is resuspended in a water for injection (WFI) or sodium chloride solution having a pH level in the range of 3.0 to 10.0 and a temperature in the range of 0° C. to 10° C.

5. The method according to claim 1, wherein the resulting APOA1 suspension is filtered with a 0.45 μm filter.

6. The method according to claim 1, wherein the chromatography process is diethylaminoethanol (DEAE) ion exchange chromatography and butyl chromatography.

7. The method according to claim 6, further comprising:
    adjusting the filtered APOA1 suspension to a pH level in the range of 3.0 to 10.0 and the ionic strength in the range of 15 mM to 25 mM;
    loading the resulting filtered APOA1 suspension into a DEAE chromatography column;
    washing the DEAE chromatography column in a low salt buffer and a high salt buffer;
    obtaining an APOA1 elute;
    adjusting the APOA1 elute to a pH level in the range of 3.0 to 10.0;
    washing the APOA1 elute in a low salt elute buffer and obtaining a purified APOA1 elute; and
    washing the purified APOA1 elute in a WFI buffer or an alkaline buffer and collecting a resulting APOA1 enriched elute.

8. The method according to claim 7, wherein the low salt buffer contains Tris having a pH level in the range of 3.0 to 10.0, the high salt buffer contains sodium chloride, the low salt elute buffer contains Tris, and the alkaline buffer contains sodium hydroxide having a pH level in the range of 3.0 to 10.0.

9. The method according to claim 7, further comprising:
    dialyzing the APOA1 enriched elute;
    concentrating the APOA1 enriched elute with virus inactivation;
    adding a stabilizer to the APOA1 enriched elute and obtaining a stabilized high purity APOA1; and
    lyophilizing the stabilized high purity APOA1.

10. A method of purifying at least one protein from a plasma fraction IV comprising:
    suspending plasma fraction IV in a buffer to obtain a suspended fraction IV;
    subjecting the suspended fraction IV to press filtering or centrifugation to remove celite and other impurities and collecting a purified fraction IV suspension;
    treating the purified fraction IV suspension with solvent/detergent (SD) virus inactivation and obtaining a virus inactivated fraction IV suspension;
    subjecting the virus inactivated fraction IV suspension to cation chromatography and obtaining a chromatographed suspension;
    eluting at least one protein from the chromatographed suspension with an eluting agent and obtaining at least one eluted fraction wherein the at least one protein comprises transferrin, human albumin, apolipoprotein A-I (APOA1), or alpha-1 antitrypsin ((A1AT)); and
    purifying the at least one protein from the eluted plasma fraction.

11. A method according to claim 10, wherein fraction IV is dissolved in a low temperature buffer.

12. A method according to claim 10, wherein suspended fraction IV is cleared by a depth filter.

13. A method according to claim 10, wherein the purified fraction IV suspension is treated with polysorbate 80 and tri(n-butyl)phosphate (TNBP) for virus inactivation at 25° C. for 6 hours.

14. A method according to claim 10, further comprising:
    dialyzing the at least one eluted fraction;
    concentrating the at least one eluted fraction;
    adjusting the pH level of the at least one eluted fraction; and
    adding a stabilizing agent to the at least one eluted fraction.

15. A method according to claim 10, further comprising subjecting the chromatographed suspension to 20 nm direct flow virus filtration for virus removal.

16. A method according to claim 10, further comprising pasteurizing the chromatographed suspension for virus removal.

17. A method according to claim 10, wherein purifying the at least one eluted fraction further comprises subjecting the at least one eluted fraction to carboxymethyl chromatography.

18. A method according to claim 10, wherein purifying the at least one eluted fraction further comprises subjecting the at least one eluted fraction to butyl chromatography.

19. A method according to claim 10, wherein purifying the at least one eluted fraction further comprises subjecting the at least one eluted fraction to blue chromatography.

20. A method according to claim 10, wherein purifying the at least one eluted fraction further comprises subjecting the at least one eluted fraction to blue chromatography and butyl chromatography.

* * * * *